US008937052B2

(12) United States Patent
Brown

(10) Patent No.: US 8,937,052 B2
(45) Date of Patent: Jan. 20, 2015

(54) THERAPEUTIC PROTOCOLS USING HYALURONAN

(75) Inventor: Tracey J. Brown, Flemington (AU)

(73) Assignee: Alchemia Oncology Pty Limited, Eight Mile Plains (AU)

( * ) Notice: Subject to any disclaimer, the term of this patent is extended or adjusted under 35 U.S.C. 154(b) by 1703 days.

(21) Appl. No.: 11/996,733

(22) PCT Filed: Jul. 27, 2006

(86) PCT No.: PCT/AU2006/001059
§ 371 (c)(1),
(2), (4) Date: Jun. 19, 2008

(87) PCT Pub. No.: WO2007/012133
PCT Pub. Date: Feb. 1, 2007

(65) Prior Publication Data
US 2009/0054537 A1     Feb. 26, 2009

Related U.S. Application Data

(60) Provisional application No. 60/703,148, filed on Jul. 27, 2005.

(51) Int. Cl.
| | | |
|---|---|---|
| A01N 43/04 | (2006.01) | |
| A61K 31/70 | (2006.01) | |
| A61K 31/715 | (2006.01) | |
| A61K 31/727 | (2006.01) | |
| A61K 45/00 | (2006.01) | |
| A61K 31/728 | (2006.01) | |
| A61K 45/06 | (2006.01) | |

(52) U.S. Cl.
CPC .............. *A61K 31/70* (2013.01); *A61K 45/00* (2013.01); *A61K 31/728* (2013.01); *A61K 45/06* (2013.01)
USPC ................................ 514/62; 514/54; 514/56

(58) Field of Classification Search
CPC ..... A61K 31/728; A61K 45/05; A61K 31/70; A61K 2300/00; A61K 45/00
USPC ............................................. 514/62, 54, 56
See application file for complete search history.

(56) References Cited

U.S. PATENT DOCUMENTS

| | | |
|---|---|---|
| 4,141,973 A | 2/1979 | Balazs |
| 4,160,452 A | 7/1979 | Theeuwes |
| 4,256,108 A | 3/1981 | Theeuwes |
| 4,265,874 A | 5/1981 | Bonsen et al. |
| 4,522,811 A | 6/1985 | Eppstein et al. |
| 4,665,107 A | 5/1987 | Micale |
| 4,736,024 A | 4/1988 | Della Valle et al. |
| 4,851,521 A | 7/1989 | della Valle et al. |
| 4,965,353 A | 10/1990 | della Valle et al. |
| 5,095,037 A | 3/1992 | Iwamitsu et al. |
| 5,128,450 A | 7/1992 | Urdal et al. |
| 5,202,431 A | 4/1993 | della Valle et al. |
| 5,208,020 A | 5/1993 | Chari et al. |
| 5,284,656 A | 2/1994 | Platz et al. |
| 5,416,071 A | 5/1995 | Igari et al. |
| 5,442,053 A | 8/1995 | Della Valle et al. |
| 5,475,092 A | 12/1995 | Chari et al. |
| 5,585,499 A | 12/1996 | Chari et al. |
| 5,662,895 A | 9/1997 | Welte et al. |
| 5,676,964 A | 10/1997 | della Valle et al. |
| 5,733,891 A | 3/1998 | Akima et al. |
| 5,744,155 A | 4/1998 | Friedman et al. |
| 5,756,475 A | 5/1998 | Inomata et al. |
| 5,756,537 A | 5/1998 | Gill |
| 5,776,925 A | 7/1998 | Young et al. |
| 5,827,834 A | 10/1998 | Falk et al. |
| 5,830,882 A | 11/1998 | Falk et al. |
| 5,840,673 A | 11/1998 | Buckbinder et al. |
| 5,846,545 A | 12/1998 | Chari et al. |
| 5,847,002 A | 12/1998 | Willoughby et al. |
| 5,852,002 A | 12/1998 | Falk et al. |
| 5,968,972 A | 10/1999 | Broder et al. |
| 5,977,088 A | 11/1999 | Harper et al. |
| 5,985,850 A | 11/1999 | Falk et al. |
| 5,985,851 A | 11/1999 | Falk et al. |
| 6,027,741 A | 2/2000 | Cialdi et al. |
| 6,069,135 A | 5/2000 | Falk et al. |
| 6,087,350 A | 7/2000 | Johnson et al. |

(Continued)

FOREIGN PATENT DOCUMENTS

| | | |
|---|---|---|
| CA | 612307 A | 1/1961 |
| CA | 1227427 A1 | 9/1987 |

(Continued)

OTHER PUBLICATIONS

Mürdter, T.E., Sperker, B., Kivistö, K.T., McClellan, M., Fritz, P., Friedel, G., Linder, A., Bosslet, K., Toomes, H., Dierkesmann, R., Kroemer, H.K. (1997) Enhanced Uptake of Doxorubicin into Bronchial Carcinoma: β-Glucuronidase Mediates Release of Doxorubicin from a Glucuronide Prodrug at the Tumor Site. Cancer Research, vol. 57, p. 2440-2445.*
Ghatak, S., Misra, S., Toole, B.P. (2002) Hyaluronan Oligosaccharides Inhibit Anchorage-independent Growth of Tumor Cells by Suppressing the Phosphoinositide 3-Kinase/Akt Cell Survival Pathway. The Journal of Biological Chemistry, vol. 277, No. 41, p. 38013-38020.*
"Combination Chemotherapy" [online] Published Apr. 22, 2003. [Retrieved on May 6, 2014] Retrieved from the internet <www.rnceus.com/chem/combo.html>.*
Frei III, E., Eder, J.P. (2003) "Combination Chemotherapy" in Holland-Frei Cancer Medicine. 6th Edition. Edited by Kufe, D.W., Pollack, R.E. Weichselbaum, R.R. et al. Published by BC Decker.*
Noble, S., Goa, K.L. (1997) Gemcitabine. A Review of its Pharmacology and Clinical Potential in Non-Small Cell Lung Cancer and Pancreatic Cancer. Drugs, vol. 54, No. 3, p. 447-472.*

(Continued)

*Primary Examiner* — Scarlett Goon
(74) *Attorney, Agent, or Firm* — Morrison & Foerster LLP

(57) ABSTRACT

The present invention relates generally to the field of therapeutics and in particular, chemotherapy. Even more particularly, the present invention provides therapeutic strategies which reduce the toxicity or enhance the efficacy of chemotherapeutic agents. Compositions and methods of treatment and prophylaxis are also contemplated by the present invention.

8 Claims, 17 Drawing Sheets

(56) References Cited

U.S. PATENT DOCUMENTS

| | | |
|---|---|---|
| 6,214,860 B1 | 4/2001 | Sola et al. |
| 6,232,301 B1 | 5/2001 | Takahashi et al. |
| 6,242,457 B1 | 6/2001 | Penco et al. |
| 6,299,900 B1 | 10/2001 | Reed et al. |
| 6,475,795 B1 | 11/2002 | Turley et al. |
| 6,552,184 B1 | 4/2003 | Pallado et al. |
| 6,579,978 B1 | 6/2003 | Renier et al. |
| 6,620,927 B2 | 9/2003 | Bulpitt et al. |
| 6,831,172 B1 | 12/2004 | Barbucci et al. |
| 7,420,033 B2 | 9/2008 | Varadhachary et al. |
| 8,287,894 B2 * | 10/2012 | Brown et al. ............ 424/422 |
| 8,388,993 B2 * | 3/2013 | Brown ............ 424/422 |
| 8,623,354 B2 | 1/2014 | Brown et al. |
| 8,741,970 B2 | 6/2014 | Brown |
| 2002/0015724 A1 | 2/2002 | Yang et al. |
| 2003/0087877 A1 | 5/2003 | Calias et al. |
| 2003/0180382 A1 | 9/2003 | Brown et al. |
| 2005/0042303 A1 | 2/2005 | Brown et al. |
| 2005/0267069 A1 | 12/2005 | Brown et al. |
| 2006/0178342 A1 | 8/2006 | Brown et al. |
| 2006/0263395 A1 | 11/2006 | Brown et al. |
| 2007/0148734 A1 | 6/2007 | Chaudhuri et al. |
| 2008/0063727 A1 | 3/2008 | Kim et al. |
| 2009/0220497 A1 | 9/2009 | Brown et al. |
| 2009/0306012 A1 | 12/2009 | Brown et al. |
| 2013/0197103 A1 | 8/2013 | Brown |

FOREIGN PATENT DOCUMENTS

| | | |
|---|---|---|
| CA | 2089621 A1 | 8/1994 |
| CA | 2122519 A1 | 10/1995 |
| CA | 2208924 A | 1/1999 |
| CA | 2370003 A1 | 7/2000 |
| CA | 2387058 A1 | 4/2001 |
| CA | 2387058 C | 4/2001 |
| EP | 0 138 572 A2 | 4/1985 |
| EP | 0 138 572 A3 | 4/1985 |
| EP | 0 138 572 B1 | 4/1985 |
| EP | 0 216 453 A2 | 4/1987 |
| EP | 0 216 453 A3 | 4/1987 |
| EP | 0 216 453 B1 | 4/1987 |
| EP | 0 265 116 B1 | 4/1988 |
| EP | 0 341 745 A1 | 11/1989 |
| EP | 0 341 745 B1 | 11/1989 |
| EP | 0 433 817 B1 | 6/1991 |
| EP | 0 626 863 B1 | 12/1994 |
| EP | 1 598 371 A1 | 11/2005 |
| JP | 61-000017 A | 1/1986 |
| JP | 4-504579 A | 8/1992 |
| JP | 2002-534484 A | 10/2002 |
| JP | 2003-518510 A | 6/2003 |
| WO | WO-91/04058 A2 | 4/1991 |
| WO | WO-93/16733 A1 | 9/1993 |
| WO | WO-94/15640 A1 | 7/1994 |
| WO | WO-94/23725 A1 | 10/1994 |
| WO | WO-95/30423 A2 | 11/1995 |
| WO | WO-95/30423 A3 | 11/1995 |
| WO | WO-95/30439 A2 | 11/1995 |
| WO | WO-95/30439 A3 | 11/1995 |
| WO | WO-96/06622 A1 | 3/1996 |
| WO | WO-97/20564 A1 | 6/1997 |
| WO | WO-97/40841 A1 | 11/1997 |
| WO | WO-98/17320 A1 | 4/1998 |
| WO | WO-98/23648 A1 | 6/1998 |
| WO | WO-99/02151 A1 | 1/1999 |
| WO | WO-00/20642 A1 | 4/2000 |
| WO | WO-00/41730 A1 | 7/2000 |
| WO | WO-01/36656 A2 | 5/2001 |
| WO | WO-01/47561 A1 | 7/2001 |
| WO | WO-02/05852 A1 | 1/2002 |
| WO | WO-02/090390 A1 | 11/2002 |
| WO | WO-03/018062 A1 | 3/2003 |
| WO | WO-2004/076491 A1 | 9/2004 |
| WO | WO-2006/107124 A1 | 10/2006 |
| WO | WO-2007/012133 A1 | 2/2007 |
| WO | WO-2007/028196 A1 | 3/2007 |

OTHER PUBLICATIONS

Brown, T.J., Vaghela, K., Pho, M., Falzon, J.L., Gibbs, P., Fox, R., Thomas, N., Brownlee, G.R. (2006) The effect of hyaluronic acid on the activity of intra-tumoral and intestinal β-glucuronidases—a potential mechanism for increasing the therapeutic index of irinotecan. Proceedings of the American Association of Cancer Research, vol. 47.*

Bucci, L.R. et al. (2004). "Will the Real Hyaluronan Please Stand Up?" *Journal of Applied Nutrition* 54(1):10-33.

Final Office Action mailed Mar. 12, 2010, for U.S. Appl. No. 11/198,663, filed Aug. 5, 2005, 14 pages.

Non-Final Office Action mailed Mar. 25, 2010, for U.S. Appl. No. 09/889,203, filed Jan. 6, 2000, 11 pages.

Final Office Action mailed Apr. 30, 2010, for U.S. Appl. No. 11/415,612, filed May 1, 2006, 13 pages.

Final Office Action mailed Jun. 30, 2010, for U.S. Appl. No. 11/198,663, filed Aug. 5, 2005, 10 pages.

Zhen, Y. et al. (eds). (Nov. 2002). *Modern Biotechnological Pharmaceutics Series*, Antibody Engineering Pharmaceutics, Chemical Industry Press et al., Beijing, China, pp. 303-302, with Certified English Translation, for a total of 10 pages.

Anonymous. (1957). "British Standard Methods for the Determination of the Viscosity of Liquids in C.G.S. Units," *British Standards Institution*, British Standards House, London, 4 pages.

Barrow, G.M. (1979). *Physical Chemistry, Fourth Edition*, Jackson, D.C. eds., McGraw-Hill Kogakusha, Ltd., Tokyo, Japan, pp. 764-765.

Wikipedia. (download on Sep. 13, 2010). "Intrinsic Viscosity," located at <http://en.wikipedia.org/wiki/Intrinsic_viscosity>, 3 pages.

Wikipedia. (download on Sep. 13, 2010). "Mark-Houwink Equation," located at <http://en.wikipedia.org/wiki/Mark%E2%80%093Houwink_equation>, 2 pages.

Wikipedia. (downloaded on Sep. 13, 2010). "Viscosity," located at <http://en.wikipedia.org/wiki/Viscosity>, 18 pages.

U.S. Appl. No. 09/889,203, filed Jan. 6, 2000, by Brown.

U.S. Appl. No. 12/482,870, filed Jun. 11, 2009, by Brown et al.

International Search Report mailed Sep. 22, 2006, for PCT Application No. PCT/AU2006/001059, filed Jul. 27, 2006, eight pages.

Rosenthal, M.A. et al. (2005, e-pub. May 9, 2005). "Phase I and Pharmacokinetic Evaluation of Intravenous Hyaluronic Acid in Combination with Doxorubicin or 5-Fluorouracil," *Chemotherapy* 51:132-141.

Takasuna, K. et al. (Aug. 15, 1996). "Involvement of β-Glucuronidase in Intestinal Microflora in the Intestinal Toxicity of the Antitumor Camptothecin Derivative Irinotecan Hydrocholoride (CPT-11) in Rats," *Cancer Research* 56:3752-3757.

Avis, K.E. (1975). "Parenteral Preparations," Chapter 84 in *Remington's Pharmaceutical Sciences*, 15th Edition, Easton: Mack Publishing Company, pp. 1461-1487.

Japanese Office Action mailed Jul. 7, 2009, for JP Application No. 2003-522577, with English translation, five pages.

Maucher, A. et al. (1994). "Antitumor Activity of Coumarin and 7-Hydroxycoumarin Against 7,12-dimethylbenz[a]anthracene-Induced Rat Mammary Carcinomas," *J. Cancer Res. Clin. Oncol.* 120:502-504.

Reynolds, J.E.F. ed. (1993). *Martindale: The Extra Pharmacopoeia*, 30th Edition, The Pharmaceutical Press: London, England, pp. 480-482.

Rivory, L.P. et al. (1996). "Conversion of Irinotecan (CPT-11) to Its Active Metabolite, 7-Ethyl-10-hydroxycamptothecin (SN-38), by Human Liver Carboxylesterase,"*Biochemical Pharmacology* 52:1103-1111.

Anonymous. (Jul. 2008). "Sodium Hyaluronate," *European Pharmacopoeia* 62:3835-3837.

Bernatchez, S.F. et al. (1994). "Sodium Hyaluronate as a Vehicle for an Improved Tolerance of 5-Fluorouracil Administered Subconjunctivally to Rabbits," *International Journal of Pharmaceutics* 106:161-166.

(56) References Cited

OTHER PUBLICATIONS

Canadian Office Action mailed Apr. 15, 2009, for CA Application No. 2,458,856, two pages.
Cunningham, D. et al. (Jul. 22, 2004). "Cetuximab Monotherapy and Cetuximab Plus Irinotecan in Irinotecan-Refractory Metastatic Colorectal Cancer," *New England Journal of Medicine* 351(4):337-345.
Deardorff, D.L. (1975). "Isotonic Solutions," Chapter 79 in *Remington's Pharmaceutical Sciences*, 15th Edition, Easton: Mack Publishing Company, pp. 1405-1412.
European Search Report mailed Sep. 26, 2005, for EP Application No. 01951219.3, four pages.
Final Office Action mailed Oct. 30, 2008, for U.S. Appl. No. 09/889,203, filed Mar. 13, 2002, 13 pages.
Final Office Action mailed May 11, 2009, for U.S. Appl. No. 11/191,407, filed Jul. 27, 2005, 12 pages.
Final Office Action mailed Nov. 29, 2010, for U.S. Appl. No. 09/889,203, filed Mar. 13, 2002, 9 pages.
Final Office Action mailed May 2, 2011, for U.S. Appl. No. 11/191,407, filed Jul. 27, 2005, 13 pages.
Final Office Action mailed May 10, 2011, for U.S. Appl. No. 12/065,945, filed Sep. 29, 2008, 10 pages.
Gustafson, S. et al. (1995). "Studies on Receptors for Hyaluronan and the Turnover of Radioactively-Labelled Hyaluronan in Mice and Rats," *Second International Workshop on Hyaluronan in Drug Delivery, Round Table Series*, Willoughby, D.A. ed., Ontario, Canada, May 1-3, 1994, 36:5-7.
Hokputsa, S. et al. (2003). "Hydrodynamic Characterisation of Chemically Degraded Hyaluronic Acid," *Carbohydrate Polymers* 52:111-117.
International Search Report dated Jul. 22, 1994, for PCT Application No. PCT/CA94/00207, filed Apr. 15, 1994, three pages.
International Search Report mailed Apr. 14, 2000, for PCT Application No. PCT/AU00/00004, filed Jan. 6, 2000, six pages.
International Search Report mailed Aug. 22, 2001, for PCT Application No. PCT/AU01/00849, filed Jul. 13, 2001, three pages.
International Search Report mailed Oct. 14, 2002, for PCT Application No. PCT/AU02/01160, filed Aug. 27, 2002, three pages.
International Search Report mailed Oct. 17, 2006, for PCT Application No. PCT/AU2006/001293, filed Sep. 4, 2006, three pages.
Izawa, O.N. et al. (May 11, 1992). "Hyaluronic Acid Derivative Synthesis and Properties (II)—Synthesis of Hyaluronic Acid Derivative with Thymine 5FU," 41st *Society of Polymer Science Japan Conference Proceedings, Polymer Preprints, Japan*, May 26-29, 1992, 42(3):479. (with English Translation, eight pages).
Japanese Office Action mailed Jul. 7, 2009, for JP Application No. 2003-522577, English Translation, five pages.
Klein, E.S. et al. (1994). "Effects of Hyaluronic Acid on Experimental Tumor Uptake of 5-Flurouracil," *Reg. Cancer Treat.* 7:163-164.
Langer, R. (Sep. 28, 1990). "New Methods of Drug Delivery," *Science* 249:1527-1533.
Luo, Y. et al. (1999, e-pub. Jul. 27, 1999). "Synthesis and Selective Cytotoxicity of Hyaluronic Acid-Antitumor Bioconjugate," *Bioconjugate Chemistry* 10:755-763.
Maucher, A. et al. (1994). "Antitumor Activity of Coumarin and 7-Hydroxycoumarin Against 7,12-dimethylbenz[α]anthracene-Induced Rat Mammary Carcinomas," *J. Cancer Res. Clin. Oncol.* 120:502-504.
Non-Final Office Action mailed May 14, 2009, for U.S. Appl. No. 11/415,612, filed May 1, 2006, four pages.
Non-Final Office Action mailed Jun. 11, 2009, for U.S. Appl. No. 11/198,663, filed Aug. 5, 2005, 14 pages.
Non-Final Office Action mailed Mar. 25, 2010, for U.S. Appl. No. 09/889,203, filed Mar. 13, 2002, 11 pages.
Non-Final Office Action mailed Oct. 8, 2010, for U.S. Appl. No. 12/065,945, filed Sep. 29, 2008, 13 pages.
Non-Final Office Action mailed, Nov. 15, 2010, for U.S. Appl. No. 11/191,407, filed Jul. 27, 2005, 11 pages.

Ouchi, T. et al. (1991). "Design of Polysaccharide-5-Fluorouracil Conjugates Exhibiting Antitumour Activities," Chapter 8 In *American Chemical Society Symposium Series*, 469(Polymeric Drugs and Drug Delivery Systems):71-83.
Reynolds, J.E.F. et al. ed. (1993). "Fluorouracil," *Martindale: The Extra Pharmacopoeia*, 30th Edition, The Pharmaceutical Press: London, England, pp. 480-482.
Rivory, L.P. et al. (1996). "Conversion of Irinotecan (CPT-11) to Its Active Metabolite, 7-Ethyl-10-hydroxycamptothecin (SN-38), by Human Liver Carboxylesterase," *Biochemical Pharmacology* 52:1103-1111.
Sakurai, K. et al. (1986). "Mucopolysaccharide-type Cancer-Metastasis Inhibitor," Japanese Kokai Patent Application No. Sho 61[1986]-17, with English Translation, 36 pages.
Stern, R. et al. (2006). "Hyaluronan Fragments: An Information-Rich System," *European Journal of Cell Biology* 85:699-715.
Taguchi, T. et al. (Jan. 1994). "An Early Phase II Study of CPT-11 (irinotecan hydrochloride) in Patients with Advanced Breast Cancer," *Gan To Kagaku Ryoho* 21(1):83-90. (Abstract Only) one page.
Tsatas, D. et al. (2002). "EGF Receptor Modifies Cellular Responses to Hyaluronan in Glioblastoma Cells Lines," *Journal of Clinical Neuroscience* 9(3):282-288.
Turley, E.A. (Mar. 1992). "Hyaluronan and Cell Locomotion," *Cancer and Metastasis Reviews* 11:21-30.
Yamamoto, O.H. et al. (May 11, 1992). "Synthesis of the Conjugate of Adriamycin with Oxidized Hyaluronic Acid," 42nd *Society of Polymer Science Japan Annual Conference Proceedings, Polymer Preprints, Japan*, May 31-Jun. 2, 1993, 42(3):898. (with English Translation, eight pages).
Yomota, C. (Jul. 3, 1997). "Research for Property Evaluation and Application of Hyaluronic Acid as a Biomedical Polymer," *1996 Human Science Fundamental Research Enterprise, Human Science Enterprise*, 16 pages (with English Translation, 28 pages).
Non-Final Office Action mailed on Jun. 30, 2011, for U.S. Appl. No. 12/482,870, filed Jun. 11, 2009, eleven pages.
Rugo, H. (2004). "Bevacizumab in the Treatment of Breast Cancer: Rationale and Current Data," *The Oncologist* 9, suppl. 1, pp. 43-49.
Brownlee, G.R. et al. (Apr. 2006). "Novel Formulations of Therapeutic Antibodies with Hyaluronic Acid (HA) in the Treatment of Colorectal Cancer: A Pre-clinical Evaluation," *Proceedings of the American Association for Cancer Research*, 97th *Annual Meeting*, Washington, DC, Apr. 1-5, 2006, 47:162, Abstract No. 682.
Declaration of Samuel Simon Asculai Under § 1.132 (1996) filed on Sep. 19, 1996 for U.S. Patent No. 6,069,135 (Issued on May 30, 2000), which Matured Out of U.S. Appl. No. 07/675,908, 239 Total Pages.
Declaration of Ian Constable Under § 1.132 (1996) filed on Sep. 20, 1996 for U.S. Patent No. 6,069,135 (Issued on May 30, 2000), which Matured Out of U.S. Appl. No. 07/675,908, 45 Total Pages.
Declaration of George A. Deveber Under § 1.132 (1996) filed on Mar. 4, 1997 for U.S. Patent No. 6,069,135 (Issued on May 30, 2000), which Matured Out of U.S. Appl. No. 07/675,908, 16 Total Pages.
Declaration of Joseph Robert Emmott Fraser Under § 1.132 (1996) filed on Mar. 4, 1997 for U.S. Patent No. 6,069,135 (Issued on May 30, 2000), which Matured Out of U.S. Appl. No. 07/675,908, 62 Total Pages.
Declaration of Joseph Robert Emmott Fraser Under § 1.132 (1997) filed on Aug. 7, 1997 for U.S. Patent No. 6,069,135 (Issued on May 30, 2000), which Matured Out of U.S. Appl. No. 07/675,908, 71 Total Pages.
Declaration of Joseph Robert Emmott Fraser Under § 1.132 (1997) for U.S. Patent No. 5,985,850 (Issued on Nov. 16, 1999), which Matured Out of U.S. Appl. No. 08/462,154, 67 Total Pages.
Declaration of Stefan Gustafson Under § 1.132 (1996) filed on Mar. 4, 1997 for U.S. Patent No. 6,069,135 (Issued on May 30, 2000), which Matured Out of U.S. Appl. No. 07/675,908, 126 Total Pages.
Declaration of Torvard C. Laurent Under § 1.132 (1996) filed on Dec. 18, 1996 for U.S. Patent No. 6,069,135 (Issued on May 30, 2000), which Matured Out of U.S. Appl. No. 07/675,908, 46 Total Pages.
Declaration of Dr. Adrian Richard Moore Under § 1.132 (1996) filed on Mar. 4, 1997 for U.S. Patent No. 6,069,135 (Issued on May 30, 2000), which Matured Out of U.S. Appl. No. 07/675,908, 27 Total Pages.

(56) References Cited

OTHER PUBLICATIONS

Declaration of Sanford H. Roth Under § 1.132 (1996) filed on Mar. 4, 1997 for U.S. Patent No. 6,069,135 (Issued on May 30, 2000), which Matured Out of U.S. Appl. No. 07/675,908, 53 Total Pages.

Declaration of Eva Turley Under § 1.132 (1996) filed on Mar. 4, 1997 for U.S. Patent No. 6,069,135 (Issued on May 30, 2000), which Matured Out of U.S. Appl. No. 07/675,908, 30 Total Pages.

Declaration of Eva Turley Under § 1.132 (1997) filed on Aug. 7, 1997 for U.S. Patent No. 6,069,135 (Issued on May 30, 2000), which Matured Out of U.S. Appl. No. 07/675,908, 60 Total Pages.

Declaration of Eva Turley Under § 1.132 (1997) filed on Apr. 14, 1999 for U.S. Patent No. 5,985,850 (Issued on Nov. 16, 1999), which Matured Out of U.S. Appl. No. 08/462,154, 68 Total Pages.

Declaration of Ian Constable Under § 1.132 (1997) filed on Mar. 4, 1997 for U.S. Patent No. 6,069,135 (Issued on May 30, 2000), which Matured Out of U.S. Appl. No. 07/675,908, 37 Total Pages.

Non-Final Office Action mailed, Jul. 6, 1994 for U.S. Patent No. 6,069,135 (Issued on May 30, 2000), which Matured Out of U.S. Appl. No. 07/675,908, 9 pages.

Non-Final Office Action mailed, Jun. 25, 1996 for U.S. Patent No. 5,985,850 (Issued on Nov. 16, 1999), which Matured Out of U.S. Appl. No. 08/462,154, 6 pages.

Non-Final Office Action mailed, Aug. 8, 2008, for U.S. Appl. No. 11/191,407, filed Jul. 27, 2005, eleven pages.

Non-Final Office Action mailed, Dec. 7, 2007, for U.S. Appl. No. 11/191,407, filed Jul. 27, 2005, seven pages.

Non-Final Office Action mailed on Aug. 30, 2013, for U.S. Appl. No. 13/325,842, filed Dec. 14, 2011, 10 pages.

Non-Final Office Action mailed Dec. 30, 2013, for U.S. Appl. No. 11/198,663, filed Aug. 5, 2005, ten pages.

Pályi-Krekk, Z. et al. (Nov. 1, 2007). "Hyaluronan-Induced Masking of ErbB2 and CD44-Enhanced Trastuzumab Internalisation in Trastuzumab Resistant Breast Cancer," *European Journal of Cancer* 43(16):2423-2433.

Response to Non-Final Office Action submitted to the USPTO Dec. 19, 1996 for U.S. Patent No. 5,985,850 (Issued on Nov. 16, 1999), which Matured Out of U.S. Appl. No. 08/462,154, 30 pages.

Response to Non-Final Office Action submitted to the USPTO Dec. 22, 1997 for U.S. Patent No. 5,985,850 (Issued on Nov. 16, 1999), which Matured Out of U.S. Appl. No. 08/462,154, 32 pages.

Response to Non-Final Office Action submitted to the USPTO Jan. 9, 1995 for U.S. Patent No. 6,069,135 (Issued on May 30, 2000), which Matured Out of U.S. Appl. No. 07/675,908, 52 pages.

Stedman (2005). *Stedman's Medical Dictionary for the Health Professions and Nursing*, Fifth Edition, Lippincott Williams & Wilkins: Baltimore, MD, pp. 766-767.

U.S. Appl. No. 14/097,029, filed Dec. 4, 2013, by Brown et al., 95 Total Pages.

Váradi, T. et al. (Aug. 2012; e-pub. May 4, 2012). "Binding of Trastuzumab to ErbB2 is Inhibited by a High Pericellular Density of Hyaluronan," *J. Histochem. Cytochem.* 60(8):567-575.

Wikipedia (Feb. 25, 2014). "Dispersity (redirected from Polydispersity Index)," located at <http://en.wikipedia.org/wiki/Polydispersity_index>, last visited on Feb. 25, 2014, three pages.

* cited by examiner

THERAPEUTIC PROTOCOLS USING HYALURONAN

CROSS-REFERENCE TO RELATED APPLICATIONS

This application is a National Phase application under 35 U.S.C. §371 of International Application No. PCT/AU2006/001059 filed Jul. 27, 2006 and claims the benefit of U.S. Provisional Application No. 60/703,148 filed Jul. 27, 2005, the disclosures of which are incorporated herein by reference in their entirety.

BACKGROUND OF THE INVENTION

1. Field of the Invention

The present invention relates generally to the field of therapeutics and in particular, chemotherapeutics and formulations useful for same. Even more particularly, the present invention provides therapeutic strategies which reduce the toxicity or enhance the efficacy of therapeutic agents. Compositions, methods of treatment and prophylaxis and therapeutic protocols are also contemplated by the present invention.

2. Description of the Prior Art

The reference to any prior art in this specification is not, and should not be taken as, an acknowledgment or any form of suggestion that that prior art forms part of the common general knowledge in any country.

Drug toxicity is a major limitation in the administration of therapeutic compounds. In order to achieve and maintain a therapeutic concentration of the active drug substance at and within the pathological site it is necessary to administer high doses of the chemotherapeutic agent. Systemic toxicity is frequently the end result, therefore in an attempt to alleviate systemic toxicity the clinician will administer sub-optimal doses of the therapeutic agent where there is an intricate balance between therapeutically active and non-toxic drug dosage. As a consequence of this compromised but balanced drug regimen, there is often sub-optimal therapeutic serum levels of a given therapeutic compound being available to a patient. Observed toxicity may result in limiting the frequency of dosing, the quantum of dosing or the number of cycles of dosing.

An example of one such therapeutic substance which is associated with significant toxicity is Irinotecan hydrochloride (CPT-11; Camptosar®. CPT-11) which is a water soluble derivative of camptothecin, a plant alkaloid with anti-tumor activity, originally isolated from *Camptotheca acuminata*. CPT-11 has a wide spectrum of anti-tumor activity and has been shown to be effective for the treatment of refractory colorectal cancer, for which CPT-11 chemotherapy has been approved worldwide.

During CPT-11 chemotherapy, the main dose limiting toxicities are delayed diarrhea and myelosuppression. Myelosuppression is a condition in which bone marrow activity is decreased. This condition leads to fewer red blood cells, white blood cells, and platelets which generally manifests as a lowered immune system and a greater prevalence to primary and secondary bacterial and/or fungal infections. The duration of myelosuppression can be partially controlled by the administration of granulocyte colony stimulating factor but this therapeutic approach is represents a high cost of treatment as well as an invasive and extended hospitalization period for the patient. Diarrhea affects the quality of life and when combined with myelosuppression can be life threatening.

CPT-11 is converted in vivo by hepatic carboxylesterase to form the active metabolite SN-38, a potent inhibitor of topoisomerase I, a nuclear enzyme critical in the process of DNA replication and transcription. In the liver, a portion of the SN-38 undergoes subsequent detoxification by glucuronidation by the UDP-glucuronysyltransferase system with the formation of inactive SN-38G. Biliary excretion represents the major elimination pathway for CPT-11 and its metabolites. Once in the intestine SN-38G can be deconjugated via bacterial or tissue beta-glucuronidase mediated cleavage to SN-38, resulting in local irritation and toxicity to the gut (Takasuna et al. *Cancer Res* 56:3752-3757, 1996). From the bowel CPT-11 and its metabolites may also be reabsorbed via intestinal cells and form an enterohepatic recirculation loop (Takasuna et al. 1996 supra).

Accordingly, although therapeutic agents are currently available which, if administered at optimal doses would be capable of treating diseases, such as cancer, infection by pathogens, the treatment of pain, gastrointestinal disorders and neurological conditions amongst many other conditions, there exists a need for compositions and therapeutic strategies which reduce debilitating side effects and/or which promote the generation of particularly efficacious forms of the therapeutic agents.

SUMMARY OF THE INVENTION

Throughout the specification, unless the context requires otherwise, the word "comprise", or variations such as "comprising" or "comprises", will be understood to imply the inclusion of the stated element or integer or group of elements or integers but not the exclusion of any other element or integer or group of elements or integers.

The present invention is predicated in part on the determination that hyaluronic acid, also referred to herein as hyaluronan or HA, or its chemically modified derivatives, modulates the levels or activities of enzymes which generate either toxic metabolites of therapeutic agents or their pro-drug forms or which generate more efficacious forms of the therapeutic agents. In addition, the proteins responsible for the re-absorption, transport and excretion of these drugs or their metabolites may be modulated by hyaluronan or HA, or its chemically modified derivatives. It is proposed, therefore, to co-administer simultaneously or sequentially in either order HA and a therapeutic agent.

The therapeutic agent may be an anti-cancer agent, an anti-pathogen agent or any agent exhibiting or conferring a beneficial therapeutic effect such as in the treatment of diabetes, neurological conditions, pain management and gastrointestinal disorders. A "beneficial therapeutic effect" includes amelioration of one or more symptoms of a disease or condition. The term "chemotherapeutic agent" should not be construed as limiting the agent to any particular type of agent (such as only an anti-cancer agent). It is to be broadly construed to cover any therapeutic agent of a chemical or proteinaceous nature. The terms "chemotherapeutic agent" and "therapeutic agent" are considered herein to be synonymous and are used interchangeably.

The present invention demonstrates surprisingly that including particularly lower molecular weight HA as a component of a formulation being used for the treatment of a disease results in a reduction of the toxicity level in the gastro-intestinal tract while altering the pharmacodynamics of the drug wherein the end result is a reduction in toxic drugs or their metabolites within the circulation.

Accordingly, the present invention provides a method of treatment comprising administration of a formulation comprising hyaluronan (HA) and a therapeutic agent, wherein said formulation or a component thereof modulates the activity of beta-glucuronidase and reduces gastrointestinal toxicity relative to the therapeutic agent alone.

Another aspect of the subject invention provides a method of treatment comprising administration of a formulation comprising hyaluronan (HA) and a therapeutic agent, wherein said formulation or a component thereof modulates the activity of drug transport proteins such a the cationic exchange protein known as cMOAT which results in reduced circulatory levels of toxic drugs or their metabolites; a clinical manifestation that has the final therapeutic effect of reduced bone marrow toxicity.

In particular, the method of treatment comprises administration of a formulation wherein the biological activity of the beta-glucuronidase in the digestive tract is modulated.

In a particular embodiment, the hyaluronan component has an average molecular weight of about 1 kDalton to about 1000 kDaltons.

In another particular embodiment, the hyaluronan component has an average molecular weight of about 1 kDalton to about 100 kDaltons.

In a further particular embodiment, the hyaluronan component has an average molecular weight of about 350 Daltons to about 10 kDaltons.

Yet another particular embodiment includes the hyaluronan component has an average molecular weight of about 350 Daltons to about 5 kDaltons.

In still another particular embodiment, the hyaluronan component has an average molecular weight of about 350 Daltons to about 2 kDaltons.

Particularly, the method of treatment comprises administration of a formulation comprising hyaluronan (HA) of MW about 350-9500 Daltons and a therapeutic agent which reduces toxicity level in the gastro-intestinal tract wherein the HA modulates the activity of beta-glucuronidase in the tract.

Particularly, the method of treatment comprises administration of a formulation comprising:
(i) hyaluronan (HA) of average molecular weight about 10 kDaltons; and
(ii) hyaluronan (HA) of average molecular weight about 860 kDaltons, and
(iii) a therapeutic agent,
wherein said formulation modulates the activity of beta-glucuronidase and reduces gastrointestinal toxicity relative to the therapeutic agent alone.

Particularly, the method of treatment comprises administration of a formulation comprising:
(i) hyaluronan (HA) of average molecular weight about 2 kDaltons; and
(ii) hyaluronan (HA) of average molecular weight about 860 kDaltons, and
(iii) a therapeutic agent,
wherein said formulation modulates the activity of beta-glucuronidase and reduces gastrointestinal toxicity relative to the therapeutic agent alone.

Particularly, the HA is administered prior or subsequent to the administration of the agent.

Particularly, the HA is administered prior to the administration of the agent.

Particularly, the HA is administered subsequent to the administration of the agent.

Particularly, the HA of average molecular weight about 10 kDaltons is administered orally.

Particularly, the HA of average molecular weight about 2 kDaltons is administered orally.

Particularly, the HA of average molecular weight about 860 kDaltons is administered systemically.

Particularly, the agent is a substrate of beta-glucuronidase.

Particularly, the therapeutic agent contains a glucuronide moiety.

Particularly, the therapeutic agent is metabolized to form a glucuronide conjugate.

Preferably, the glucuronide is selected from the list consisting of morphine-3-glucuronide, morphin-6-glucuronide, lithocholate glucuronide, D-glucuronide, estrone-3-glucuronide, retinoyl glucuronide, imboxyl-beta-D-doxorubicin glucuronide, androstaneodiol glucuronide and paracetamol glucuronide.

Preferably, the chemotherapeutic agent is selected form the list consisting of daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxy-cyclophosphoramide, 5-fluorouracil (5-FU), 5-fluorodeoxyuridine (5-FUdR), methotrexate (MTX), oxaliplatin, colchicine, taxol, vincristine, vinblastine, etoposide (VP-16), trimetrexate, irinotecan, topotecan, gemcitabine, teniposide, cisplatin, diethylstilbestrol (DES) and a glucuronide conjugate thereof.

Preferably, the chemotherapeutic agent is selected from the list consisting of chemotherapeutic compounds include antimetabolites, antitumor antibiotics, mitotic inhibitors, steroids, hormones, alkylating agents, nitrogen mustards, nitrosoureas, hormone agonists and microtubule inhibitors. Other useful therapeutic agents include extracts or purified molecules from biological sources such as plants, coral or microorganisms. Anti-cancer agents from plants are particularly useful in isolated form or as fractions or extracts.

Another aspect of the invention provides a method of treatment comprising administration of a formulation comprising hyaluronan (HA) and a therapeutic agent, wherein said formulation or a component thereof modulates the activity of beta-glucuronidase and enhances drug activation relative to the therapeutic agent alone.

Another aspect of the invention provides a method of treatment comprising administration of a formulation comprising hyaluronan (HA) and a therapeutic agent, wherein said formulation modulates the activity of beta-glucuronidase and reduces myelosuppression relative to the therapeutic agent alone.

Preferably, the hyaluronan component has an average molecular weight of about 1 kDalton to about 1000 kDaltons.

Preferably, the hyaluronan component has an average molecular weight of about 1 kDalton to about 100 kDaltons.

Preferably, the hyaluronan component has an average molecular weight of about 350 Daltons to about 10 kDaltons.

Preferably, the hyaluronan component has an average molecular weight of about 350 Daltons to about 5 kDaltons.

Preferably, the hyaluronan component has an average molecular weight of about 350 Daltons to about 2 kDaltons.

Preferably, the method of treatment comprises administration of a formulation comprising:
(i) hyaluronan (HA) of average molecular weight about 10 kDaltons; and
(ii) hyaluronan (HA) of average molecular weight about 860 kDaltons, and
(iii) a therapeutic agent, wherein said formulation modulates the activity of beta-glucuronidase and reduces myelosuppression relative to the therapeutic agent alone.

Preferably, the method of treatment comprises administration of a formulation comprising:
(i) hyaluronan (HA) of average molecular weight about 2 kDaltons; and
(ii) hyaluronan (HA) of average molecular weight about 860 kDaltons, and
(iii) a therapeutic agent,
wherein said formulation modulates the activity of beta-glucuronidase and reduces myelosuppression relative to the therapeutic agent alone.

Preferably, the HA is administered prior or subsequent to the administration of the agent.

Preferably, the HA is administered prior to the administration of the agent.

Preferably, the HA is administered subsequent to the administration of the agent.

Preferably, the HA is administered orally.

Preferably, the HA of average molecular weight about 10 kDaltons is administered orally.

Preferably, the HA of average molecular weight about 2 kDaltons is administered orally.

Preferably, the HA is administered systemically.

Preferably, the HA of average molecular weight about 860 kDaltons is administered systemically.

Preferably, the therapeutic agent contains a glucuronide moiety.

Preferably, the glucuronide is selected from the list consisting of morphine-3-glucuronide, morphin-6-glucuronide, lithocholate glucuronide, estrone-3-glucuronide, retinoyl glucuronide, imboxyl-beta-D-glucuronide, doxorubicin glucuronide, androstaneodiol glucuronide and paracetamol glucuronide.

Preferably, the agent is a chemotherapeutic agent is selected form the list consisting of daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxy-cyclophosphoramide, 5-fluorouracil (5-FU), 5-fluorodeoxyuridine (5-FUdR), methotrexate (MTX), oxaliplatin, colchicine, taxol, vincristine, vinblastine, etoposide (VP-16), trimetrexate, irinotecan, topotecan, gemcitabine, teniposide, cisplatin, diethylstilbestrol (DES) and a glucuronide conjugate thereof.

Preferably, the agent is a chemotherapeutic agent selected from the list consisting of chemotherapeutic compounds include antimetabolites, antitumor antibiotics, mitotic inhibitors, steroids, hormones, alkylating agents, nitrogen mustards, nitrosoureas, hormone agonists and microtubule inhibitors Preferably, a pharmaceutical composition comprising a formulation according to the invention is used to treat cancer.

Reference herein to "treatment" includes prophylaxis and amelioration of one or more symptoms.

DETAILED DESCRIPTION OF THE INVENTION

Figure 1:
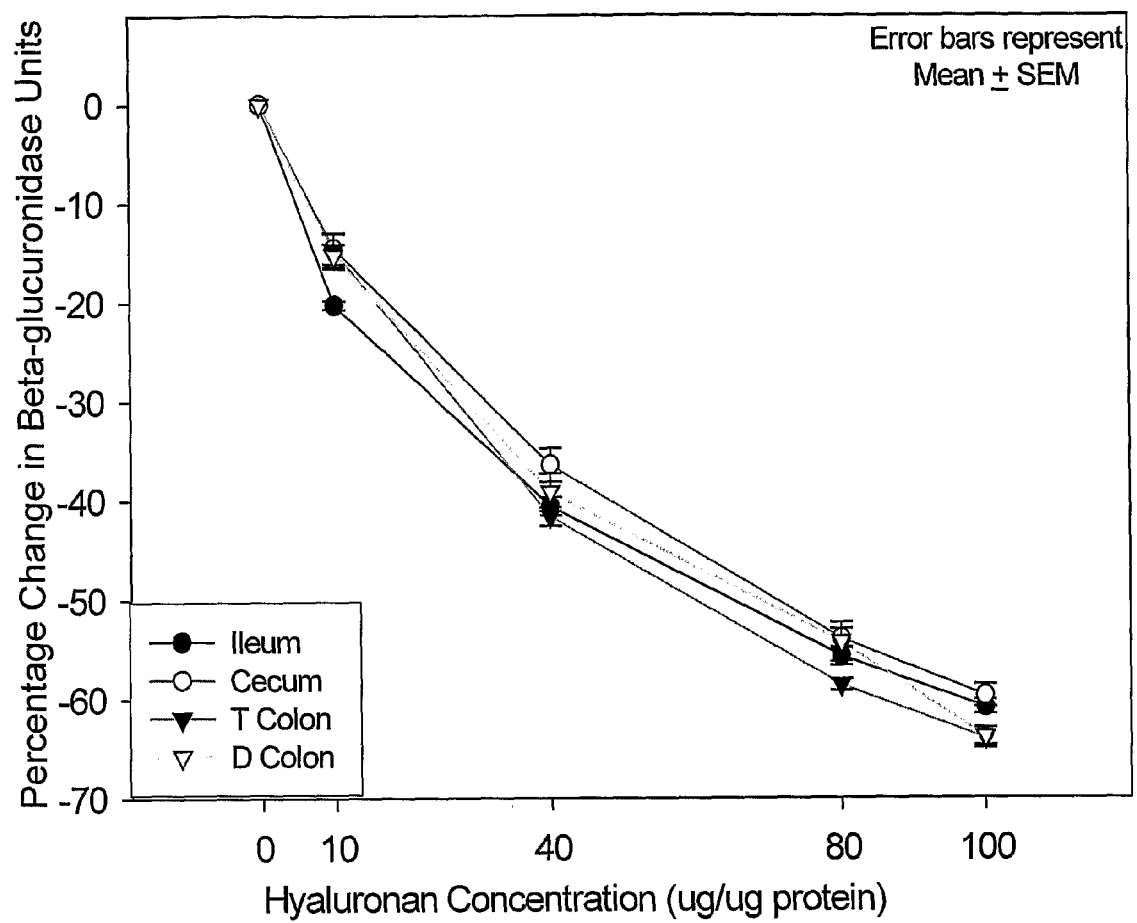
FIG. 1 is a graphical representation demonstrating the effect of <2 kDa HA on beta-Glucuronidase activity on GI tract tissue.

The present invention is predicated in part on the determination that hyaluronic acid (HA) alters the metabolism of therapeutic agents. Reference to "alters" in this context means modulates since in some circumstances enzymes which metabolize therapeutic agents or their pro-drug forms to toxic products or intermediates are inhibited. Consequently, there is a reduced level of toxic metabolic byproducts of a therapeutic agent relative to administration of the agent in the absence of HA. In other circumstances, levels of enzymes which generate more active therapeutic metabolic byproducts are elevated and hence the efficacy of the administered agent or its pro-drug form is enhanced relative to the administration of the agent in the absence of HA.

Accordingly, the instant invention provides a method of treatment comprising administration of a formulation comprising hyaluronan (HA) and a therapeutic agent, wherein said formulation or components thereof modulate the activity of beta-glucuronidase and reduce gastrointestinal toxicity relative to the therapeutic agent alone.

The terms "therapeutic agent" and "chemotherapeutic agent" are considered herein to be synonymous terms and are used interchangeably throughout the subject specification. The terms are to be construed in their broadest sense to include any chemical or pertinacious molecule employed to induce, exhibit or confer a therapeutic event or benefit. A therapeutic agent may be a non-naturally occurring chemical such as an anti-cancer agent or an anti-pathogen agent. Alternatively, the chemotherapeutic agent is an antibiotic or a recombinant molecule. In one particular embodiment, the chemotherapeutic agent is a substrate of a glucuronidase such as a beta-glucuronidase. The term "substrate" in this context means that a glucuronidase is capable of catalyzing a metabolic change in the chemotherapeutic agent. According to this aspect, the present invention provides a therapeutic protocol for a subject wherein said therapeutic protocol involves the administration of a chemotherapeutic agent or a pro-drug form of said agent, said method comprising administering to said subject, HA or a derivative thereof before, during or following administration of the therapeutic agent or its pro-drug form in an amount effective to modulate the level or activity of enzymes which render the therapeutic agent or its pro-drug form toxic or more active relative to the administration of the agent in the absence of HA.

It is to be understood that unless otherwise indicated, the subject invention is not limited to specific formulations of components, manufacturing methods, dosage regimes, or the like, as such may vary. It is also to be understood that the terminology used herein is for the purpose of describing particular embodiments only, and is not intended to be limiting.

In addition, as used in the subject specification, the singular forms "a", "an" and "the" include plural aspects unless the context clearly dictates otherwise. Thus, for example, reference to "a chemotherapeutic agent", "an anti-cancer agent", "the hyaluronic acid" and so forth includes a single entity (i.e. a single anti-cancer agent, chemotherapeutic agent or hyaluronic acid) as well as two or more entities.

The term "HA" is used in its most general sense and is also known as sodium hyaluronate, hyaluronan or hyaluronic acid. All these terms may be used to describe the same entity. It is a mucopolysaccharide which is in every part of mammalian body, and the main component of mammalian connective tissues. Under physiological conditions, HA can, inter alia, absorb water into intercellular space to make "jelly matrix". In vivo, this serves to protect cell structure and defend against external insult, bacterial infections and the like.

The instant invention also provides compositions including one or more anticancer antibodies and derivatives, fragments and/or salts of HA. A number of derivatives and fragments of HA have been described in the literature and are intended to be included in the methods and formulations of the instant invention.

Exemplary HA derivatives are those described in U.S. Pat. No. 6,620,927 (thiol-modified hyaluronic acid derivatives); U.S. Pat. No. 6,552,184 (crosslinked compounds of hyaluronic acid and the derivatives thereof); U.S. Pat. No. 6,579,978 (sulphated compounds of hyaluronic acid and derivatives thereof); U.S. Pat. No. 6,831,172 (cross-linked hyaluronic acids and hemisuccinylated derivates thereof); U.S. Pat. No. 6,027,741 (sulfated hyaluronic acid and esters thereof); European Patent No. 0 138 572 (Hyaluronic acid fragments HYALECTIN and HYALASTINE).

Falk's earlier patents (eg, U.S. Pat. No. 5,852,002; U.S. Pat. No. 6,069,135) define hyaluronic acid as a naturally occurring glycosaminoglucan, the molecular weight of which may vary from 50,000 daltons upwards. Fidia's patents (eg EP 013852) disclose a hyaluronic acid called HYALASTINE of MW of about 50 kDa-100 kDa which possess characteristics desirable for a topically applied material useful in promoting wound healing. A lower molecular weight material comprising fractions of less than 30 kDa is also disclosed by Fidia et. al. However, these fractions were discarded as impurities and therefore teach away from the use as formulations as described in the present invention. International Patent Application No. WO 00/41730 and WO 02/05852, for example, relate primarily to use of HA of molecular weight higher than 750 kDa. While WO 02/05852 describes several low molecular weight hyaluronans (eg a tetrasaccharide, a hexasaccharide, and a dodecasaccharide, as well as HA's of 5600 Da, and 50,000 Da), these low molecular weight hyaluronans were used to determine the effect of HA on the cell cycle. None of this prior art discloses the use of HA of less than 10,000 Da to reduce toxicity level and/or ameliorate myelosuppression. Surprisingly, HA of the present invention includes fractions of MW much lower than 50,000 Da, particularly lower than 10,000 Da, preferably about 2000 Da. which advantageously reduce toxicity in the gastro-intestinal tract and/or ameliorate myelosuppression.

Hence, the present invention extends to the use of HA having a molecular weight from about 350 Daltons to 1000 kDa such as 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000 Da and 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000 Da including molecular weights in between.

In addition to fragments and derivatives of HA, synthetic derivatives, and/or semisynthetic derivatives may be used in the methods and compositions of the invention. Exemplary semisynthetic derivatives of HA are esters of HA with alcohols of the aliphatic, aromatic, heterocyclic and cycloaliphatic series, designated "HYAFF," that are described in U.S. Pat. Nos. 4,851,521, 4,965,353, and 5,202,431, EP 0 341 745 and EP 0 216 453. The contents of each of the above-identified patents are expressly incorporated herein by reference.

The term "subject" as used herein refers to an animal, preferably a mammal and more preferably human who can benefit from the compositions and methods of the present invention. There is no limitation on the type of animal that could benefit from the present methods. A subject regardless of whether a human or non-human animal may be referred to as an individual, subject, animal, host or recipient. The methods of the present invention have applications in human medicine, veterinary medicine as well as in general, domestic or wild animal husbandry. Preferably, the candidate subject is a mammal such as a human or laboratory test animal such as a mouse, rat, rabbit, guinea pig, hamster or avian species such as a poultry bird.

Hyaluronan is an unbranched polysaccharide made up of alternating glucuronic acid and N-acetyl glucosamine units. Being a polymeric molecule, HA molecules may exhibit a range of molecule weights. HA formulations may, therefore, comprise molecules of different molecular weights. Almost any average of modal molecular weight formulation of HA may be effective in the methods of the present invention and the present invention is not limited to any particular size or size range of HA. The minimal unit of HA is a disaccharide of molecular mass 397 daltons. Higher saccharides are multiples of this disaccharidic unit and the molecular masses will be a multiple of $(n-1\times379)+397$, thus the tetrasaccharide (two minimal units, $n=2$) will have a molecular mass of 776 etc. Preferably, n is between about 5 and about 2200. Since higher molecular weight hyaluronans are metabolized or biodegraded to lower molecular weigh hyaluronans, we anticipate that hyaluronans of any average molecular weight can be used according to the present invention.

The terms such as "hyaluronic acid", "hyaluronan", "HA" and the like as used herein also encompass chemical or polymeric or cross-linked derivatives of HA. Examples of chemical modifications which may be made to HA include any reaction of an agent with the four reactive groups of HA, namely: the acetamido, carboxyl, hydroxyl and the reducing end.

As indicated above, the HA and chemotherapeutic agent may be administered as a single composition with both entities admixed together or the therapeutic agent embedded with the HA. Alternatively, the HA and therapeutic agent are administered separately, in either order within seconds, minutes, hours, days or weeks of each other. Accordingly, simultaneous and sequential administration of the HA and therapeutic agent in either order forms part of the present invention.

The present invention extends to the treatment of cancer as well as a range of other conditions such as infection with a range of bacterial, fungal, yeast, viral and parasites. Examples of pathogens include Human Immunodeficiency Virus (HIV), Hepatitis B virus (HBV), Hepatitis C virus (HCV), *Plasmodium* species and Multi-resistant *Stephylococcus*.

Other disease conditions include the treatment of pain (acute and/or neuropathic pain), diabetes, gastrointestinal disorders (e.g. diarrhea) and neurological conditions including Parkinson's disease, Alzheimer's disease and Hunting-ton's disease. In fact, any disease condition for which a glucuronide may be given to track or present the condition is contemplated by the present invention.

In one particular embodiment, however, the disease is cancer. Reference to "cancer" includes tumors, sarcomas, carcinomas etc.

Accordingly, another aspect of the present invention contemplates a method for treating a subject having cancer said method comprising administering to said subject HA or a derivative thereof before, during or following administration of an anti-cancer chemotherapeutic agent or a pro-drug form thereof in an amount effective to modulate the level of activity of enzymes which render the anti-cancer chemotherapeutic agent or its pro-drug form toxic or more active relative to the administration of the agent in the absence of HA.

As indicated above, reference to "anti-cancer chemotherapeutic agent" includes reference to multiple, i.e. two or more therapeutic agents. In a preferred embodiment, the chemotherapeutic agent is a substrate of a glucuronidase and in a most preferred embodiment is a glucuronide.

In one preferred embodiment, the present invention provides a method for treating or preventing the growth and/or metastasis of "solid" tumors in a subject. As used herein a "solid tumor" refers to one or more cells which are growing or have grown in an uncontrolled manner to form a tumor, without any differentiation of those cells into specialized and different cells. As used herein, the term "solid tumor" includes, but is not limited to "carcinomas", "adenocarcinomas" and "sarcomas". "Sarcomas" are cancers of the connective tissue, cartilage, bone, muscle, and so on. "Carcinomas" are cancers of epithelial (lining) cells. "Adenocarcinoma" refers to carcinoma derived from cells of glandular origin.

Exemplary "tumors" which may be treated in accordance with the present invention include AIDS Related tumors, Acoustic Neuroma, Adenocystic carcinoma, Adrenocortical Cancer, Agnogenic myeloid metaplasia, Alopecia, Alveolar soft-part sarcoma, Anal cancer, Angiosarcoma, Aplastic Anaemia, Astrocytoma, Ataxia-telangiectasia, Basal Cell Carcinoma (Skin), Bladder Cancer, Bone Cancers, Bowel cancer, Brain Stem Glioma, Brain and CNS Tumors, Breast Cancer, CNS tumors, Carcinoid Tumors, Cervical Cancer, Childhood Brain Tumors, Childhood Cancer, Childhood Soft Tissue Sarcoma, Chondrosarcoma, Choriocarcinoma, Colorectal Cancers, Cutaneous T-Cell Lymphoma, Dermatofibrosarcoma-protuberans, Desmoplastic-Small-Round-Cell-Tumor, Ductal Carcinoma, Endocrine Cancers, Endometrial Cancer, Ependymoma, Esophageal Cancer, Ewing's Sarcoma, Extra-Hepatic Bile Duct Cancer, Eye Cancer, Eye: Melanoma, Retinoblastoma, Fallopian Tube cancer, Fanconi Anaemia, Fibrosarcoma, Gall Bladder Cancer, Gastric Cancer, Gastrointestinal Cancers, Gastrointestinal-Carcinoid-Tumor, Genitourinary Cancers, Germ Cell Tumors, Gestational-Trophoblastic-Disease, Glioma, Gynecological Cancers, Haematological Malignancies, Head and Neck Cancer, Hepatocellular Cancer, Hereditary Breast Cancer, Histiocytosis, Hodgkin's Disease, Human Papillomavirus, Hydatidiform mole, Hypercalcemia, Hypopharynx Cancer, IntraOcular Melanoma, Islet cell cancer, Kaposi's sarcoma, Kidney Cancer, Langerhan's-Cell-Histiocytosis, Laryngeal Cancer, Leiomyosarcoma, Li-Fraumeni Syndrome, Lip Cancer, Liposarcoma, Liver Cancer, Lung Cancer, Lymphedema, Lymphoma, Hodgkin's Lymphoma, Non-Hodgkin's Lymphoma, Male Breast Cancer, Malignant-Rhabdoid-Tumor-of-Kidney, Medulloblastoma, Melanoma, Merkel Cell Cancer, Mesothelioma, Metastatic Cancer, Mouth Cancer, Multiple Endocrine Neoplasia, Mycosis Fungoides, Myelodysplastic Syndromes, Myeloma, Myeloproliferative Disorders, Nasal Cancer, Nasopharyngeal Cancer, Nephroblastoma, Neuroblastoma, Neurofibromatosis, Nijmegen Breakage Syndrome, Non-Melanoma Skin Cancer, Non-Small-Cell-Lung-Cancer-(NSCLC), Ocular Cancers, Oesophageal Cancer, Oral cavity Cancer, Oropharynx Cancer, Osteosarcoma, Ostomy Ovarian Cancer, Pancreas Cancer, Paranasal Cancer, Parathyroid Cancer, Parotid Gland Cancer, Penile Cancer, Peripheral-Neuroectodermal-Tumors, Pituitary Cancer, Polycythemia vera, Prostate Cancer, Rare-cancers-and-associated-disorders, Renal Cell Carcinoma, Retinoblastoma, Rhabdomyosarcoma, Rothmund-Thomson Syndrome, Salivary Gland Cancer, Sarcoma, Schwannoma, Sezary syndrome, Skin Cancer, Small Cell Lung Cancer (SCLC), Small Intestine Cancer, Soft Tissue Sarcoma, Spinal Cord Tumors, Squamous-Cell-Carcinoma-(skin), Stomach Cancer, Synovial sarcoma, Testicular Cancer, Thymus Cancer, Thyroid Cancer, Transitional-Cell-Cancer-(bladder), Transitional-Cell-Cancer-(renal-pelvis-/-ureter), Trophoblastic Cancer, Urethral Cancer, Urinary System Cancer, Uroplakins, Uterine sarcoma, Uterus Cancer, Vaginal Cancer, Vulva Cancer, Waldenstrom's-Macroglobulinemia and Wilms' Tumor.

The tumor which is treated using the methods of the present invention may be a primary lesion or may be the result of metastasis of a primary cancer. Furthermore, if the tumor is a metastasis of a primary cancer, the primary cancer may be either a primary tumor as described above or may be a dispersed primary cancer such as a leukaemia or lymphoma.

The present invention contemplates "administration" of HA to a subject. As used herein the term "administration" should be considered to encompass all methods of administration of HA. As would be evident to one of skill in the art, the most convenient or suitable route of administration will depend on several factors and as such may vary from subject to subject. However, the most convenient or suitable route of administration for any particular subject would be readily determined by one of skill in the art without undue experimentation. Routes of administration include intra-arterial, intra-hepatic, sub-cutaneous, intravenous, via inhalation, suppository or in a slow-release formulation including during surgery or although the present invention should not be considered in any way limited to these particular routes. In addition, the HA and the chemotherapeutic agent may be administered via different routes or the same routes.

The preferred concentration of HA is from about 0.00001% w/v to 10,000% w/v, where this concentration of HA is administered over a period of 1 min and up to 336 hrs but with a preferred infusion time of 120 min. Again, the HA may be given simultaneously with the chemotherapeutic agent or both entities may be given sequentially in either order. In addition, the therapeutic protocol may include multiple administrations of one or HA or the chemotherapeutic agent and less frequent administration of the other of HA and the chemotherapeutic agent.

By "co-administered" is meant simultaneous administration in the same formulation or in two different formulations via the same or different routes or sequential administration by the same or different routes. By "sequential" administration is meant a time difference of from seconds, minutes, hours, days or weeks between the administration of the two agents or treatment protocols. The sequentially administered agents or treatment protocols may be administered in any order. In one embodiment, the HA and the chemotherapeutic agent are co-administered via delivery in the same formulation or the HA is administered prior to the administration of the therapeutic agent and/or subsequent to the administration of the therapeutic agent.

In another embodiment, the therapeutic agent may be encapsulated by or otherwise associated with the HA or its derivatives. HA can be chemically modified to from a high molecular weight, viscous material that could embolize and entrap smaller therapeutic compounds such as the therapeutic agents as described below. In yet another embodiment, HA may be chemically modified to form HA beads which could be filled with therapeutic agents which collectively could embolize within a target tissue.

Examples of such therapeutic agents which may be co-administered with HA or its derivatives include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), oxaliplatin, doxorubicin, colchicine, taxol, vincristine, vinblastine, etoposide (VP-16), trimetrexate, irinotecan, topotecan, gemcitabine, teniposide, cisplatin, diethylstilbestrol (DES) and glucuronide conjugates thereof. Further non-limiting examples of chemotherapeutic compounds include antimetabolites, antitumor antibiotics, mitotic inhibitors, steroids, hormones, alkylating agents, nitrogen mustards, nitrosoureas, hormone agonists and microtubule inhibitors. The composition can also include antibodies or proteins that exert anti-angiogenic activity or anti-cancer activity through modulation of cancer-related receptors or binding proteins.

As used herein the term "antimetabolites" includes substances which interfere with the body's chemical processes needed for cell growth and reproduction; in cancer treatment, antimetabolite drugs disrupt DNA production, which in turn prevents cell division. Examples include Azaserine, D-Cycloserine, Mycophenolic acid, Trimethoprim, 5-fluorouracil, capecitabine, methotrexate, gemcitabine, cytarabine (ara-C) and fludarabine.

"Antitumor antibiotics" include compounds which interfere with DNA by stopping enzymes and mitosis or altering the membranes that surround cells. These agents work in all phases of the cell cycle. Thus, they are widely used for a variety of cancers. Examples of anti-tumor antibiotics include dactinomycin, daunorubicin, doxorubicin (Adriamycin), idarubicin, and mitoxantrone.

"Mitotic inhibitors" include plant alkaloids and other compounds derived from natural products. They can inhibit, or stop, mitosis or inhibit enzymes for making proteins needed for reproduction of the cell. These work during the M phase of the cell cycle. Examples of mitotic inhibitors include paclitaxel, docetaxel, etoposide (VP-16), vinblastine, vincristine, and vinorelbine.

The term "steroids" as used herein includes natural hormones and hormone-like drugs that are useful in treating some types of cancer (lymphoma, leukemias, and multiple myeloma) as well as other illnesses. When these drugs are used to kill cancer cells or slow their growth, they are considered chemotherapy drugs. They are often combined with other types of chemotherapy drugs to increase their effectiveness. Examples include prednisone and dexamethasone.

"Hormones" including sex hormones and hormone-like drugs, alter the action or production of female or male hormones. They are used to slow the growth of breast, prostate, and endometrial (lining of the uterus) cancers, which normally grow in response to hormone levels in the body. These hormones typically do not work in the same ways as standard chemotherapy drugs. Examples include anti-estrogens (tamoxifen, fulvestrant), aromatase inhibitors (anastrozole, letrozole), progestins (megestrol acetate), anti-androgens (bicalutamide, flutamide), and LHRH agonists (leuprolide, goserelin).

"Alkylating agents" include compounds which work directly on DNA to prevent the cancer cell from reproducing. As a class of drugs, these agents are not phase-specific (in other words, they work in all phases of the cell cycle). These drugs are active against chronic leukemias, non-Hodgkin's lymphoma, Hodgkin's disease, multiple myeloma, and certain cancers of the lung, breast, and ovary. Examples of alkylating agents include busulfan, cisplatin, carboplatin, chlorambucil, cyclophosphamide, ifosfamide, dacarbazine (DTIC), mechlorethamine (nitrogen mustard) and melphalan.

"Nitrogen mustards" such as those in the form of its crystalline hydrochloride are used as a drug in the treatment of Hodgkin's disease, non-Hodgkin's lymphomas, and brain tumors. Nitrogen mustards cause mutations in the genetic material of cells, thereby disrupting mitosis, or cell division. Cells vary in their susceptibility to nitrogen mustards, with rapidly proliferating tumor and cancer cells most sensitive; bone marrow, which produces red blood cells, is also sensitive, and depression of red blood cell production is a frequent side effect of nitrogen mustard therapy. The nitrogen mustards also suppress the immune response (see immunity). Other types include the aromatic mustards melphalan and chlorambucil, cyclophosphamide, HN1, bis-(2-chloroethyl), ethylamine; HN2, bis-(2-chloroethyl), methylamine and HN3, tris-(2-chloroethyl), amine.

"Nitrosoureas" generally act in a similar way to alkylating agents. They interfere with enzymes that help repair DNA. These agents are able to travel to the brain so they are used to treat brain tumors as well as non-Hodgkin's lymphomas, multiple myeloma, and malignant melanoma. Examples of nitrosoureas include carmustine (BCNU) and lomustine (CCNU).

"Hormone agonists" include compounds which modulate the activity of one or more hormones. Examples include Leuprolide (Lupron, Viadur, Eligard) for prostate cancer, Goserelin (Zoladex) for breast and prostate cancers and Triptorelin (Trelstar) for ovarian and prostate cancers and nafarelin acetate (Synarel).

"Microtubule inhibitors" include compounds such as the vinca alkaloids, taxoids and benzimidazoles.

Particularly important chemotherapeutic compounds contemplated by the present invention are glucuronides or glucuronide conjugates. Examples of glucuronides encompassed by the present invention include but are not limited to morphine-3-glucuronide, morphin-6-glucuronide, lithocholate glucuronide, retinoyl glucuronide, imboxyl-beta-D-glucuronide, estrone-3-glucuronide, doxorubicin glucuronide, androstaneodiol glucuronide and paracetamol glucuronide.

In one particular embodiment, the therapeutic agent is the anti-cancer agent, irinotecan. Co-administration of irinotecan with HA inhibits conversion of the non-toxic SN-38G form into the toxic SN-38 form. It is proposed that HA inhibits the activity of beta-glucuronidase. HA or fragments thereof appear to compete with SN-38G for beta-glucuronidase conversion and hence gastrointestinal (GI) tract toxicity is reduced.

Figure 2:
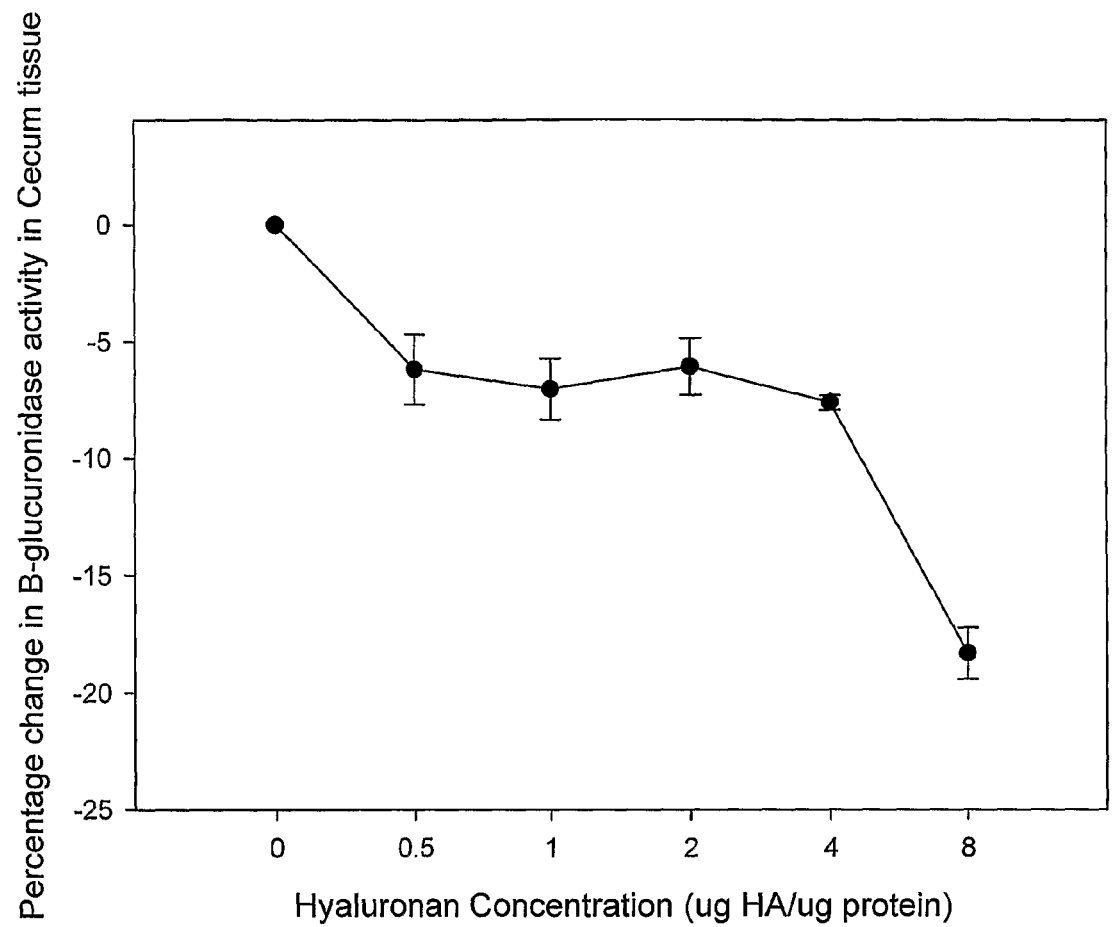
FIG. 2 is a graphical representation demonstrating the effect of <2 kDa HA on beta-Glucuronidase activity in GI Tract tissue.

The data provided in the present invention demonstrate that non-physiologically achievable concentrations of hyaluronans (860 and 10 kDa) can exert a stimulatory effect on the activity of endogenous beta-glucuronidase derived from hepatic and GI tract tissue and luminal contents. In contrast, however, low molecular weight HA (<2 kDa) exerts an inhibitory effect on endogeneous beta-glucuronidase derived from the liver and GI tract tissues (FIGS. 1 and 2). The catabolism of HA to fragments <2 kDa may interfere with the conversion of SN-38G to SN-38 is a possible mechanism by which exogenously administered HA may reduce the severity of CPT-11'-induced gastrointestinal tract toxicity.

The novel, HA/Chemotherapeutic-based compositions and/or formulations described above (also referred to herein as "active compounds") of the present invention can be incorporated into pharmaceutical compositions suitable for administration. Such compositions typically comprise the active compounds and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. As discussed above, supplementary active compounds can also be incorporated into the compositions.

A pharmaceutical composition of the invention is formulated to be compatible with its intended route of administration. Examples of routes of administration include, but are not limited to, parenteral, e.g., intravenous, intradermal, intramuscular, intraosseous, subcutaneous, oral, intranasal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The composition preferably is sterile and should be fluid to the extent that easy syringability exists. The compositions suitably should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminium monostearate and gelatin.

Sterile injectable solutions can be prepared by incorporating the active compound in a therapeutically effective or beneficial amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. Suitable oral compositions may be e.g. enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as hydroxyfluoroalkane (HFA), or a nebulizer. Alternatively, intranasal preparations may be comprised of dry powders with suitable propellants such as HFA.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially e.g. from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the ED50 (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions (e.g. written) for administration, particularly such instructions for use of the active agent to treat against a disorder or disease as disclosed herein, including diseases or disorders associated with Siglec-8 expressing cells.

The present invention is also useful in increasing the half life or maintaining stability of particular therapeutic agents such as proteins, peptides and antibodies in the blood stream or other biological fluids.

The following non-limiting examples are illustrative of the invention. All documents mentioned herein are incorporated herein by reference in their entirety.

Example 1

Determining the Effect of HA Concentration and Molecular Weight on Beta-Glucuronidase Activity in Gastrointestinal Tissue and Gastrointestinal Contents In Vitro Preparation of GI Tract Tissue Homogenates and GI Tract (Luminal) Content Sonicates Portions of the ileum, cecum, transverse and descending colon of the gastrointestinal (GI) tract were dissected from male out-bred Sprague Dawley rats. The luminal contents of each section was then removed and weighed. Each tissue section was then thoroughly rinsed with ice cold 0.9% w/v sodium chloride solution and weighed. Ileum, cecum, transverse and descending colon were then homogenized in ice-cold potassium phosphate buffer for 10 minutes using an Ultra-Turrax tissue homogenizer. Luminal contents recovered from the ileum, cecum, transverse and descending colon were also homogenized in the same manner. All samples were then subjected to sonication disruption for 4 minutes followed by centrifugation 4° C. for 30 minutes at 6000 $g_{av}$. The resulting supernatants were quantitated for protein content using the BCA method.

Preparation of Liver Tissue Homogenates

The liver was weighed then homogenized in ice cold 20 mM Tris/HCl pH7.5 buffer containing 0.2% v/v TritonX100 for 5-10 minutes then centrifuged at 4° C. for 30 minutes at 6000 $g_{av}$. Supernatants were quantitated for protein content using the BCA method, aliquoted and stored at −20° C. until use.

Preparation of 4-Methylumbelliferone (4-MU) Standard Curve

For the purpose of these examples 1 Unit of beta-glucuronidase activity was defined as 1 nmol of 4 MU liberated per mg/hr (Sands et al. *Protocols for Gene Transfer in Neuroscience* 263-274, 1996). Accordingly, to allow the conversion of relative fluorescence (from assayed tissue and luminal content homogenates) to units of enzyme activity a standard curve of 4-MU was prepared ranging between 0-10 Units of beta-glucuronidase activity.

Liver homogenates were diluted to 0.8 mg/mL and the GI tract and luminal contents to 0.1 mg/ml prior to assay set up.

10 mg/ml hyaluronan stock of modal MW 860 kDa and 10 kDa was added to the diluted samples as per Table 1. In this manner when 100 μl of each sample was used for the assay the concentration range of HA to a fixed amount of protein was; 10 μg, 40 μg, 80 μg and 100 μg HA per μg of protein.

TABLE 1

| Tube number | μg HA/ μg protein | Vol of the 0.1 mg/ml sample (μl) | Vol of HA added (μl) | Diluent (Potassium phosphate buffer) (μl) | Final Vol (μl) |
|---|---|---|---|---|---|
| 1 | 0 μg | 500 | 0 | 1000 | 1500 |
| 2 | 10 μg | 500 | 50 | 950 | 1500 |
| 3 | 40 μg | 500 | 200 | 800 | 1500 |
| 4 | 80 μg | 500 | 400 | 600 | 1500 |
| 5 | 100 μg | 500 | 500 | 500 | 1500 |

25 mg/ml hyaluronan stock of <2 kDa MW was added to the diluted samples as per Table 2. In this manner when 100 μl of each sample was used for the assay the concentration range of HA to a fixed amount of protein was; 10 μg, 40 μg, 80 μg and 100 μg HA per μg of protein.

TABLE 2

| Tube number | HA/μg protein (μg) | Vol of the 0.1 mg/ml sample (μl) | Vol of HA added (μl) | Diluent (Potassium phosphate buffer) (μl) | Final Vol (μl) |
|---|---|---|---|---|---|
| 1 | 0 μg | 500 | 0 | 1000 | 1500 |
| 2 | 10 μg | 500 | 20 | 980 | 1500 |
| 3 | 40 μg | 500 | 80 | 920 | 1500 |
| 4 | 80 μg | 500 | 160 | 840 | 1500 |
| 5 | 100 μg | 500 | 200 | 800 | 1500 |

After the addition of HA all samples were thoroughly mixed then incubated overnight at 37° C. after which they were then used for the quantification of beta-glucuronidase activity.

Beta-Glucuronidase Assay: 96-Well-Plate Method

For the GI tract assay, 100 μl of sample (3.33 μg), 100 μl of substrate and 100 μl of stop buffer were used. The assay was performed in triplicate in 96-well black clear-bottom plates. For control samples an equivalent volume of 75 mM potassium phosphate buffer in place of a biological sample was used. The reaction was started by addition of the appropriate volume of 500 μM of 4-Methylumbelliferyl-beta-D-Glucuronide (4-MUBG) substrate into each test and blank well. The plates were incubated at 37° C. for 1 hour after which stop buffer was added to each well. The amount of product generated in each well was then recorded in a Fluostar Optima plate reader following excitation at 350 nm and fluorescence recorded at 450 nm.

Example 2

Determining the Effect of HA Concentration and Molecular Weight on Hepatic Beta-Glucuronidase Activity In Vitro Liver homogenate stocks were diluted to 0.8 mg/mL before being used for the assay. Hyaluronan (860 kDa, 10 kDa and <2 kDa) was diluted to 8 mg/ml, 3.2 mg/ml, 1.6 mg/ml, 0.4 mg/ml, 0.2 mg/ml, 0.04 mg/ml, 0.02 mg/ml and 0.0008 mg/ml in potassium phosphate buffer. Aliqouts of 0.8 mg/ml liver homogenates were then thoroughly mixed with an equivalent volume of each diluted preparation of HA and incubated overnight at 37° C. Next day, the samples were briefly flick mixed before quantification of the beta-glucuronidase activity. Refer to Table 3 for sample preparation:

TABLE 3

| Tube number | HA concentration in mg/ml | μg HA/μg protein |
|---|---|---|
| 1 | 8 mg/ml | 10 μg |
| 2 | 3.2 mg/ml | 4 μg |
| 3 | 1.6 mg/ml | 2 μg |
| 4 | 0.4 mg/ml | 0.5 μg |
| 5 | 0.2 mg/ml | 0.25 μg |
| 6 | 0.04 mg/ml | 0.05 μg |
| 7 | 0.02 mg/ml | 0.025 μg |
| 8 | 0.0008 mg/ml | 0.001 μg |

Analysis of Data

Raw fluorescence readings were corrected for background fluorescence using the blank control sample. Using a standard curve of known amounts of 4-MU, and hence units of beta-glucuronidase activity the corrected fluorescence readings were then translated into units of enzyme activity. The following formula was then used to determine the percentage change in beta-glucuronidase enzyme activity:

Percentage change of no $HA$ control =

$$\left[ \frac{\text{Fluorescence of sample}}{\text{Fluorescence of no } HA \text{ control}} \times 100 \right] - 100$$

The mean of the percentage change, standard deviation (SD) of the percentage change and the standard error of the mean (SEM) of the percentage change was determined to plot the graph. All assay determinations were performed in triplicate.

Establishing Standard Curve for the Quantitation of Beta-Glucuronidase Activity

For the purposes of these Examples, one unit of the beta-glucuronidase enzyme is equivalent to the generation of 1 nmole of the 4-MU/hr (Wolfe & Sands *Protocols for Gene Transfer in Neuroscience*, 1996). By varying concentrations of the end product of the reaction 4-MU a standard curve relating relative fluorescence units to known amounts of beta-glucuronidase activity was prepared. By using a concentrations range of 4-MU of 0.01 μm-50 μm a standard curve relating to 0.01-10 Units beta-glucuronidase activity was generated. The standard curve was linear over this range of 0.001-5 units with the average $r^2$ coefficient=0.99 (n=5) as shown in Table 4.

TABLE 4

| 4-MU Conc. (μM) | Equivalent beta-glucuronidase Units | Fluorescence Units Mean ± SD |
|---|---|---|
| 0.01 | 0.001 | 27 ± 4 |
| 0.1 | 0.01 | 121 ± 13 |
| 1 | 0.1 | 1100 ± 56 |
| 2.5 | 0.25 | 2678 ± 4 |
| 5 | 0.5 | 5571 ± 54 |
| 10 | 1.0 | 10342 ± 226 |
| 25 | 2.5 | 22476 ± 511 |
| 50 | 5.0 | 37947 ± 1068 |
| 75 | 7.5 | 48039 ± 171 |
| 100 | 10.0 | 55895 ± 421 |

Example 3

Determining the Effect of HA Molecular Weight and Concentration on Beta-Glucuronidase Activity in GI Tract Tissue Homogenates In Vitro Evaluation of <2 kDa HA The effect of <2 kDa HA on the activity of beta-glucuronidase in tissue homogenates from the gastrointestinal tract was determined. The quantitation of the beta-glucuronidase units expressed as percentage change in beta-glucuronidase activity compared to the untreated tissue samples (mean±SEM) are shown in Table 5 and FIG. 1. At 40 μg, 80 μg and 100 μg of HA there was significant decrease in beta-glucuronidase activity. Using the highest concentration of HA in this assay (100 μg) beta-glucuronidase activity was inhibited by up to 64%.

As the caecum was assayed to contain the highest beta-glucuronidase activity further dose titration of HA from 8-0.5 μg HA/μg protein was undertaken.

TABLE 5

| HA (<2 kDa) μg HA/μg protein | Ileum tissue | Cecum tissue | T Colon tissue | D Colon tissue |
|---|---|---|---|---|
| 0 | 0 | 0 | 0 | 0 |
| 10 | −20 ± 0 | −15 ± 2 | −15 ± 2 | −15 ± 1 |
| 40 | −41 ± 1 | −36 ± 2 | −42 ± 1 | −39 ± 2 |
| 80 | −56 ± 1 | −54 ± 1 | −59 ± 1 | −54 ± 2 |
| 100 | −61 ± 1 | −60 ± 1 | −64 ± 1 | −64 ± 1 |

Determining the Concentration of Activity Thresholds of <2 kDa HA

HA was further titrated to encompass the following range 0.5 to 8 μg HA/μg protein and the assay repeated from the tissue homogenate derived from the cecum. The quantitation of the beta-glucuronidase units expressed as percentage change in activity compared to the untreated tissue samples (mean±SEM) are shown in Table 6 and FIG. 2.

TABLE 6

| HA conc (ug HA/ug protein) | % Change | SEM |
|---|---|---|
| 0 | 0 | 0 |
| 0.5 | −6 | 2 |
| 1 | −7 | 1 |
| 2 | −6 | 1 |
| 4 | −8 | 0 |
| 8 | −18 | 1 |

Evaluation of 10 kDa HA

The effect of 10 kDa HA on the activity of beta-glucuronidase in tissue homogenates from the gastrointestinal tract was determined. The quantitation of the beta-glucuronidase units expressed as percentage change in beta-glucuronidase activity compared with the untreated tissue samples (mean±SEM) are shown in Table 7. HA at 40 μg, 80 μg and 100 μg/μg protein significantly increased the beta-glucuronidase activity. At 100 μg of HA/μg of tissue, beta-glucuronidase activity increased by up to 43%.

TABLE 7

| HA (10 kDa) μg HA/μg protein | Ileum tissue | Cecum tissue | T Colon tissue | D Colon tissue |
|---|---|---|---|---|
| 0 | 0 | 0 | 0 | 0 |
| 10 | 6 ± 3 | 4 ± 2 | 1 ± 0 | 9 ± 4 |
| 40 | 29 ± 2 | 14 ± 1 | 18 ± 1 | 19 ± 4 |
| 80 | 39 ± 2 | 34 ± 1 | 34 ± 1 | 24 ± 5 |
| 100 | 43 ± 3 | 40 ± 5 | 37 ± 2 | 32 ± 5 |

Evaluation of 860 kDa HA

The effect of 860 kDa molecular weight HA on the activity of beta-glucuronidase in tissue homogenates from the gastrointestinal tract was determined. The quantitation of the beta-glucuronidase units expressed as percentage change in beta-glucuronidase activity compared to the untreated tissue samples (mean±SEM) are shown in Table 8. At 80 μg and 100 μg of HA/μg protein there was an increase in beta-glucuronidase activity in ileum, cecum and the transverse colon. As the concentration of the HA increased from ≥80 μgHA/μg protein, the beta-glucuronidase activity was increased by up to 41%.

TABLE 8

| HA (860 kDa) μg HA/μg protein | Ileum tissue | Cecum tissue | T Colon tissue | D Colon tissue |
|---|---|---|---|---|
| 0 | 0 | 0 | 0 | 0 |
| 10 | 5 ± 1 | 8 ± 1 | 5 ± 4 | 6 ± 2 |
| 40 | 13 ± 5 | 19 ± 7 | 20 ± 3 | 4 ± 3 |
| 80 | 31 ± 3 | 25 ± 5 | 29 ± 3 | 10 ± 4 |
| 100 | 39 ± 1 | 28 ± 4 | 41 ± 2 | 17 ± 5 |

Example 4

Determining the Effect of HA Concentration and Molecular Weight on Beta-Glucuronidase Activity in Gastrointestinal Tissue and Gastrointestinal Contents In Vivo Male Sprague-Dawley rats were purchased from Monash Animal Central Services (Monash University, Clayton). After one week acclimitisation rats were randomly assigned to respective treatment groups (n=5). Each animal was then restrained and subjected to a single bolus injection of test article (see Table 9) in the lateral tail vein.

TABLE 9

The treatment groups and doses of CPT-11 and HA

| Treatment Group | CPT-11 Dosage (mg/kg) | HA Dosage (mg/kg) |
|---|---|---|
| CPT-11 (30) | 30.0 | 0 |
| CPT-11 (60) | 60.0 | 0 |
| HyCAMP ™ (13.0/30) | 30.0 | 13.0 |
| HyCAMP ™ (13.0/60) | 60.0 | 13.0 |
| HyCAMP ™ (26.6/30) | 30.0 | 26.6 |
| HyCAMP ™ (26.6/60) | 60.0 | 26.6 |
| HyCAMP ™ (55/30) | 30.0 | 55.0 |
| HyCAMP ™ (55/60) | 60.0 | 55.0 |

A single intravenous injection of each test article outlined in Table 9, rats from each treatment condition were sacrificed at 90 minutes, 3 hour and 6 hour time points. Blood and portions of the liver, small intestine, large intestine, spleen and kidneys were excised, weighed and immediately frozen until quantitation by HPLC of CPT-11, SN-38 and SN-38G was undertaken.

Extraction of CPT-11 and SN-38 from Blood Samples

CPT-11 and SN-38 was extracted from the maximum volume (200 μL) of blood sample by adding 400 μl of 0.1% orthophosphoric acid in methanol and acetonitrile (60:40). Each sample was then vortexed for 1 minute followed by extraction for 1 hour at room temperature with constant agitation. At the completion of the extraction the samples were vortexed for 2 minutes, and centrifuged at 13000 $g_{av}$ for 5 minutes, 4° C. The supernatant was then air-dried.

Following reconstitution of the air dried sample in 200 μl of HPLC mobile phase the sample was then vortexed for 5 minutes and centrifuged at 13,000 $g_{av}$ for 5 minutes at 4° C. The resulting supernatant was then analyzed by reverse-phase high performance liquid chromatography (HPLC), as using the elution conditions outlined in Table 10.

TABLE 10

The HPLC Conditions Used to Detect and Quantitate CPT-11 and SN-38

| Column | SS Wakosil II (150 × 4.6 mm) C18 5 μm; Product #206605 |
|---|---|
| Column Temperature | 30° C. |
| Detector Wavelength | Excitation 350 nm, Emission 556 nm |
| Flow rate | 1.0 ml/min |
| Guard column | All-guard cartridge system: C18 Alltima guard column (7.5 × 4.6 mm), 5 μm |
| Mobile Phase | Isocratic gradient containing 0.025 M $KH_2PO_4$ and Acetonitrile (75:25) which was adjusted to pH 2.5 with orthophosphoric acid |
| Injection volume | 30 μl |
| Run time | 20 minutes |

Extraction of CPT-11 and SN-38 from Organs and Feces Sample

Organ and feces samples were homogenized prior to CPT-11 and SN-38 extraction. CPT-11 and SN-38 was then extracted from organ and feces sample by adding 400 μl 0.1% orthophosphoric acid in methanol and acetonitrile (60:40) to each 50 mg sample. After vortexing for 2 minutes all samples were incubated at room temperature for 1 hour with periodic agitation after which time the samples were centrifuged at 13,000 $g_{av}$ for 10 minutes at 4° C. The resulting supernatant was then transferred into a clean Eppendorf tube then air dried before reconstituting in 200 μL of HPLC mobile phase. All samples were then re-centrifuged at 13,000 $g_{av}$ for 5 minutes at 4° C. then analysed for by reverse-phase high performance liquid chromatography (HPLC) using the elution conditions outlined in Table 10.

Estimation of SN-38G Levels in Blood or Tissue Homogenates

Blood samples, tissue homogenates and fecal matter from small and large intestine were mixed with 15-fold volume (w/v) of cold methanol (−20° C.) then vortexed until a homogenous solution was achieved. Following centrifugation at 3000 $g_{av}$ for 2-minutes at 4° C. the supernatant was transferred to a clean Eppendorf microcentrifuge tube. Chromatographic separations were achieved using a TSK gel ODS-80TS column (150×4.6 mm I.D.), and a mobile phase gradient. Mobile phase A and B were 0.075 M ammonium acetate buffer (pH6.4) and acetonitrile, respectively. Gradient elution were employed according to the following linear program of mobile phase B: time zero, 15%; 6 min, 30%; 9 min, 55%; 13 min, 55% and 15 min, 15%; where the flow rate was 1.1 ml/min, with a total run time of 20 min, and column temperature was maintained at 40° C. while the autosampler at 4° C. The fluorescence detector was set at an excitation wavelength of 355 nm and emission wavelength 515 nm.

Calculations

The peak areas of the standards and samples will be manually entered onto a spreadsheet to graph the standard curve. The amount of the sample is extrapolated from the standard curve and the final calculation of the samples is calculated as follow:

$$\text{Concentration} = \frac{\text{extrapolated amount from std curve} \times \text{dilution factor}}{\text{Injection volume}}$$

Quantity of $CPT\text{-}11$ or $SN\text{-}38$ = Concentration × Reconstitution Volume $CPT\text{-}11$ or $SN\text{-}38$ Concentration in Sample =

$$\frac{\text{Quantity of } CPT\text{-}11 \text{ or } SN\text{-}38}{\text{Quantity of Sample extracted}}$$

Data is represented graphically by mean±sem. Comparison between treatment groups and time points were achieved by statistical analysis using parametric t-test analysis. On failing of normal distribution, implementation of non-parametric analysis was carried out using Mann-Whitney Rank Sum test.

Results

Tables 11-14 summarize the pharmacokinetic and pharmacodynamic data for CPT-11, SN-38 and SN-38G derived from all experimental groups outlined in Table 9.

TABLE 11

Figure 3:
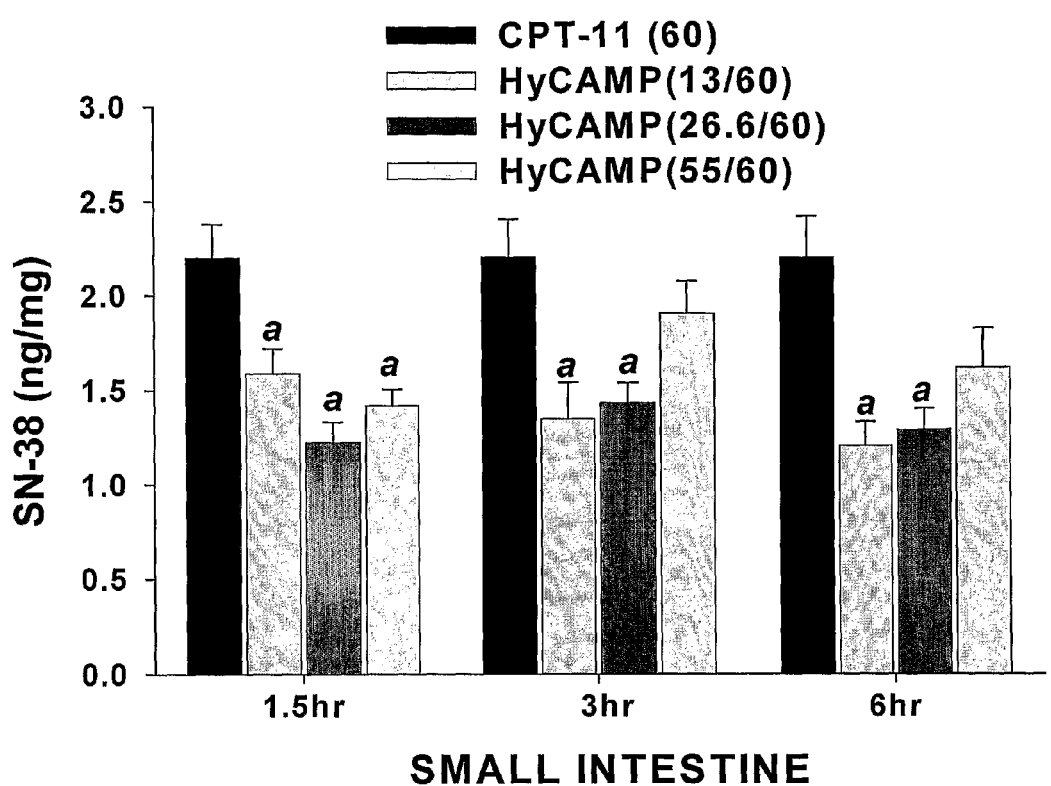
FIG. 3 is a graphical representation demonstrating the effect of HA dose modulation on tissue distribution of SN-38 when irinotecan is administered at a dose of 60 mg/kg.

The effect of HA dose modulation on tissue distribution of SN-38 in the small intestine when irinotecan is administered at a dose of 60 mg/kg (refer FIG. 3)

| Time (hr) | Quantitation of SN-38(ng/mg) ± sem | | | |
|---|---|---|---|---|
| | CPT-11 (60) | HyCAMP (13/60) | HyCAMP (26/60) | HyCAMP (55/60) |
| 1.5 | 2.2 ± 0.2 | 1.6 ± 0.1 | 1.2 ± 0.1 | 1.4 ± 0.08 |
| 3 | 2.2 ± 0.2 | 1.4 ± 0.2 | 1.4 ± 0.1 | 1.9 ± 0.2 |
| 6 | 2.2 ± 0.2 | 1.2 ± 0.1 | 1.3 ± 0.1 | 1.6 ± 0.2 |

TABLE 12

Figure 4:
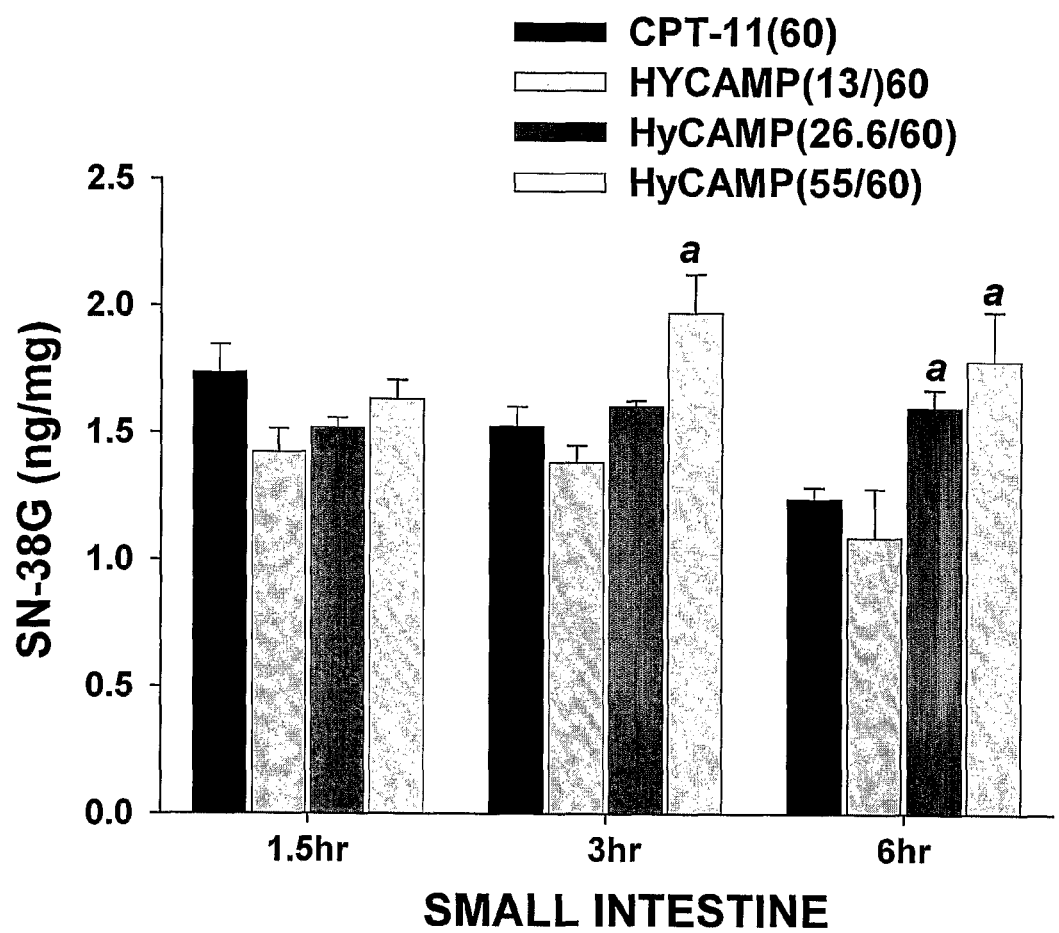
FIG. 4 is a graphical representation demonstrating the effect of HA dose modulation on tissue distribution of SN-38G when irinotecan is administered at a dose of 60 mg/kg.

The effect of HA dose modulation on tissue distribution of SN-38G in the small intestine when irinotecan is administered at a dose of 60 mg/kg (refer FIG. 4)

| Time (hr) | Quantitation of SN-38(ng/mg) ± sem | | | |
|---|---|---|---|---|
| | CPT-11 (60) | HyCAMP (13/60) | HyCAMP (26/60) | HyCAMP (55/60) |
| 1.5 | 1.7 ± 0.1 | 1.4 ± 0.09 | 1.5 ± 0.04 | 1.6 ± 0.07 |
| 3 | 1.5 ± 0.07 | 1.4 ± 0.06 | 1.6 ± 0.02 | 2.0 ± 0.2 |
| 6 | 1.2 ± 0.04 | 1.1 ± 0.2 | 1.6 ± 0.07 | 1.8 ± 0.2 |

As seen in Tables 11-14, the primary pharmacokinetic and pharmacodynamic effects exerted by the formulation of HA with irinotecan (HyCAMP) are:

i. There is more of the CPT-11 metabolite SN-38 in the blood stream demonstrating that the biliary excretion and intestinal transport of the drug is altered which would be a consequence of HA altering the activity of the cMOAT transport protein and excretionary channels ii In the small intestine there is less SN-38 and more SN-38G unequivocally demonstrating that HA inhibits the activity of intestinal beta-glucuronidase which results in reduced gastrointestinal toxicity.

TABLE 13a

Pharmacokinetics and pharmacodynamics of HyCAMP (13/30) and HyCAMP (26/30) and HyCAMP(55/30) formulation in rats

| | CPT-11 | | | | SN-38 | | | | SN-38G | | | |
|---|---|---|---|---|---|---|---|---|---|---|---|---|
| | CPT-11 30 | HyCAMP 13/30 | HyCAMP 26/30 | HyCAMP 55/30 | CPT-11 30 | HyCAMP 13/30 | HyCAMP 26/30 | HyCAMP 55/30 | CPT-11 30 | HyCAMP 13/30 | HyCAMP 26/30 | HyCAMP 55/30 |
| PLASMA (ng/ml) | | | | | | | | | | | | |
| 1.5 h | 4635 ± 70 | 2813 ± 372 | Not Detected | 460 ± 398 | 550 ± 72 | 724 ± 55 | 1975 ± 64 | 1988 ± 203 | 25 ± 2 | 26 ± 1 | 21 ± 1 | 26 ± 2 |
| 3 h | 1188 ± 280 | 744 ± 238 | Not Detected | 23 (n = 1) | 665 ± 84 | 528 ± 63 | 794 ± 33 | 891 ± 54 | 27 ± 2 | 27 ± 3 | 21 ± 1 | 21 ± 1 |
| 6 h | Not Detected | 134 (n = 1) | Not Detected | Not Detected | 303 ± 117 | 164 ± 10 | 160 ± 12 | 191 ± 15 | 39 ± 13 | 26 ± 1 | 25 ± 2 | 28 ± 2 |
| LIVER (ng/mg tissue) | | | | | | | | | | | | |
| 1.5 h | 76 ± 7 | 77 ± 9 | 85 ± 6 | 81 ± 6 | 1.1 ± 0.1 | 0.9 ± 0.1 | 1.0 ± 0.1 | 0.7 ± 0.03 | 8 ± 0.6 | 6.9 ± 0.3 | 6.4 ± 0.3 | 6.3 ± 0.2 |
| 3 h | 44 ± 6 | 28 ± 2 | 33 ± 2 | 34 ± 3 | 1.0 ± 0.2 | 0.5 ± 0.1 | 0.5 ± 0.06 | 0.5 ± 0.05 | 7.5 ± 0.3 | 7.3 ± 0.4 | 6.4 ± 0.4 | 5.2 ± 0.3 |
| 6 h | 8 ± 1 | 7 ± 0.1 | 9 ± 2 | 9 ± 1 | 0.4 ± 0.07 | 0.2 ± 0.02 | 0.3 ± 0.03 | 0.4 ± 0.06 | 7 ± 0.3 | 6.8 ± 0.02 | 5.4 ± 0.2 | 4.3 ± 0.6 |
| KIDNEYS (ng/mg tissue) | | | | | | | | | | | | |
| 1.5 h | 149 ± 15 | 129 ± 13 | 167 ± 11 | 153 ± 5 | 0.5 ± 0.1 | 0.4 ± 0.03 | 0.4 ± 0.03 | 0.3 ± 0.1 | 13 ± 0.7 | 13 ± 0.5 | 15 ± 0.8 | 17 ± 0.5 |
| 3 h | 57 ± 2 | 40 ± 3 | 57 ± 6 | 62 ± 7 | 0.3 ± 0.03 | 0.2 ± 0.01 | 0.2 ± 0.01 | 0.2 ± 0.01 | 12 ± 0.6 | 15 ± 1 | 15 ± 2 | 15 ± 1 |
| 6 h | 9 ± 1 | 8 ± 0.2 | 11 ± 1 | 9 ± 1 | 0.1 ± 0.01 | 0.1 ± 0.01 | 0.1 ± 0.0 | 0.1 ± 0.01 | 15 ± 0.7 | 15 ± 1 | 17 ± 1 | 17 ± 2 |
| SPLEEN (ng/mg tissue) | | | | | | | | | | | | |
| 1.5 h | 137 ±4 | 113 ± 9 | 163 ± 7 | 171 ± 4 | Not Detected | Not Detected | Not Detected | Not Detected | 1.5 ± 0.1 | 1.9 ± 0.4 | 1.7 ± 0.2 | 1.8 ± 0.2 |
| 3 h | 72 ± 10 | 34 ± 6 | 70 ± 7 | 84 ± 5 | Not Detected | Not Detected | Not Detected | Not Detected | 1.8 ± 0.1 | 2.0 ± 0.2 | 1.8 ± 0.1 | 1.4 ± 0.2 |
| 6 h | 9 ± 0.6 | 10 ± 1 | 10 ± 1 | 12 ± 1 | Not Detected | Not Detected | Not Detected | Not Detected | 1.4 ± 0.2 | 1.4 ± 0.2 | 1.7 ± 0.1 | 1.6 ± 0.2 |

Less than CPT-11   More than CPT-11

TABLE 13b

Pharmacokinetics and pharmacodynamics of HyCAMP (13/30) and HyCAMP(26/30) and HyCAMP(55/30) formulation in rats

| | CPT-11 | HyCAMP 13/30 | HyCAMP 26/30 | HyCAMP 55/30 | CPT-11 | HyCAMP 13/30 | HyCAMP 26/30 | HyCAMP 55/30 | CPT-11 | HyCAMP 13/30 | HyCAMP 26/30 | HyCAMP 55/30 |
|---|---|---|---|---|---|---|---|---|---|---|---|---|
| SMALL INTESTINES (ng/ml tissue) | | | | | | | | | | | | |
| 1.5 h | 46 ± 6 | 36 ± 3 | 25 ± 2 | 47 ± 6 | 1.4 ± 0.1 | 1.5 ± 0.04 | 1.1 ± 0.09 | 1.7 ± 0.1 | 1.2 ± 0.1 | 1.5 ± 0.1 | 1.5 ± 0.2 | 2.2 ± 0.1 |
| 3 h | 88 ± 9 | 60 ± 8 | 26 ± 2 | 42 ± 4 | 1.9 ± 0.1 | 2.1 ± 0.2 | 1.2 ± 0.09 | 1.5 ± 0.2 | 2.0 ± 0.3 | 1.7 ± 0.1 | 1.5 ± 0.1 | 2.4 ± 0.3 |
| 6 h | 16 ± 2 | 9 ± 1 | 10 ± 0.4 | 10 ± 1 | 1.7 ± 0.1 | 1.0 ± 0.08 | 1.0 ± 0.04 | 1.0 ± 0.05 | 1.5 ± 0.2 | 1.4 ± 0.05 | 1.5 ± 0.1 | 1.5 ± 0.2 |
| CONTENTS OF SMALL INTESTINES (ng/mg tissue) | | | | | | | | | | | | |
| 1.5 h | 312 ± 30 | 298 ± 27 | 293 ± 18 | 443 ± 35 | 6.5 ± 0.9 | 5.3 ± 1 | 9.1 ± 2 | 11.8 ± 2 | 7.1 ± 0.9 | 17.6 ± 3.4 | 14.2 ± 4.4 | 9.9 ± 2.0 |
| 3 h | 447 ± 71 | 317 ± 42 | 484 ± 53 | 437 ± 43 | 7.6 ± 1.1 | 7.7 ± 1 | 9.2 ± 1 | 7.5 ± 0.6 | 16.3 ± 1.1 | 10.5 ± 2.5 | 15.3 ± 4.1 | 13.4 ± 3.3 |
| 6 h | 99 ± 10 | 102 ± 20 | 138 ± 8 | 121 ± 11 | 7.0 ± 1 | 8.9 ± 2 | 14.3 ± 2 | 13.9 ± 2 | 17.8 ± 1 | 6.8 ± 0.5 | 11.3 ± 2.1 | 8.0 ± 0.4 |
| LARGE INTESTINES (ng/mg tissue) | | | | | | | | | | | | |
| 1.5 h | 13 ± 1 | 12 ± 0.6 | 11 ± 1 | 11 ± 1 | 0.4 ± 0.9 | Not Detected | Not Detected | 0.3 ± 0.1 | 1.3 ± 0.1 | 1.5 ± 0.1 | 2.2 ± 0.1 | 2.1 ± 0.1 |
| 3 h | 33 ± 3 | 42 ± 3 | 16 ± 1 | 19 ± 2 | 1.2 ± 1.1 | 2.1 ± 0.2 | 1 ± .01 | 0.9 ± 0.1 | 1.4 ± 0.1 | 1.8 ± 0.1 | 2.2 ± 0.1 | 1.8 ± 0.06 |
| 6 h | 59 ± 6 | 44 ± 4 | 23 ± 3 | 25 ± 4 | 2.8 ± 0.1 | 2.1 ± 0.6 | 1.3 ± 0.2 | 1.5 ± 0.2 | 1.8 ± 0.1 | 1.9 ± 0.1 | 1.7 ± 0.04 | 1.7 ± 0.06 |
| CONTENTS OF LARGE INTESTINES (ng/mg tissue) | | | | | | | | | | | | |
| 1.5 h | 84 ± 17 | 62 ± 6 | 63 ± 8 | 52 ± 10 | 1.6 ± 1.1 | 0.5 ± 0.04 | 0.3 ± 0.05 | 0.7 ± 0.4 | 10.8 ± 0.8 | 8.9 ± 0.5 | 10.9 ± 1.1 | 9.7 ± 0.1 |
| 3 h | 267 ± 24 | 359 ± 61 | 194 ± 13 | 277 ± 64 | 10.5 ± 1.2 | 16.5 ± 3.1 | 14.2 ± 0.6 | 12.5 ± 2.3 | 7.9 ± 0.5 | 8.5 ± 0.5 | 10.3 ± 0.9 | 8 ± 0.5 |
| 6 h | 806 ± 86 | 878 ± 84 | 714 ± 70 | 704 ± 47 | 38 ± 4.2 | 44 ± 4.4 | 38 ± 3.1 | 33.3 ± 22 | 9.2 ± 0.6 | 11.1 ± 1.4 | 8.6 ± 0.3 | 9.3 ± 0.5 |

Less than CPT-11 ▒ ; More than CPT-11 ■

TABLE 14a

Pharmacokinetics and pharmacodynamics of HyCAMP (13/60) and HyCAMP(26/60) and HyCAMP(55/60) formulation in rats

| | CPT-11 | | | | SN-38 | | | | SN-38G | | | |
|---|---|---|---|---|---|---|---|---|---|---|---|---|
| | CPT-11 60 | HyCAMP 13/60 | HyCAMP 26/60 | HyCAMP 55/60 | CPT-11 60 | HyCAMP 13/60 | HyCAMP 26/60 | HyCAMP 55/60 | CPT-11 60 | HyCAMP 13/60 | HyCAMP 26/60 | HyCAMP 55/60 |
| PLASMA (ng/ml) | | | | | | | | | | | | |
| 1.5 h | 11010 ± 1100 | 10066 ± 577 | 4629 ± 519 | 2567 ± 901 | 584 ± 106 | 481 ± 117 | 2191 ± 120 | 3486 ± 280 | 25 ± 2 | 28 ± 2 | 20 ± 1 | 26.3 ± 3 |
| 3 h | 4800 ± 600 | 4126 ± 608 | 2335 ± 841 | Not Detected | 614 ± 113 | 669 ± 43 | 1519 ± 374 | 2146 ± 154 | 27 ± 1 | 26 ± 2 | 25 ± 3 | 21 ± 1 |
| 6 h | 990 ± 580 | 1421 ± 604 | 716 (n = 1) | Not Detected | 670 ± 47 | 474 ± 76 | 691 ± 105 | 891 ± 41 | 32 ± 3 | 30 ± 2 | 36 ± 6 | 31 ± 3 |
| LIVER (ng/mg tissue) | | | | | | | | | | | | |
| 1.5 h | 194 ± 22 | 161 ± 8 | 183 ± 23 | 177 ± 18 | 1.6 ± 0.2 | 0.9 ± 0.1 | 1.0 ± 0.2 | 1.3 ± 0.1 | 7.5 ± 0.2 | 6.9 ± 0.3 | 6.4 ± 0.1 | 3.4 ± 0.9 |
| 3 h | 108 ± 7 | 100 ± 10 | 99 ± 7 | 83 ± 12 | 1.0 ± 0.1 | 0.9 ± 0.1 | 0.9 ± 0.05 | 0.9 ± 0.2 | 7.3 ± 0.3 | 7.3 ± 0.4 | 6.2 ± 0.2 | 4.2 ± 0.6 |
| 6 h | 31 ± 4 | 27 ± 2 | 33 ± 8 | 37 ± 4 | 0.8 ± 0.1 | 0.5 ± 0.1 | 0.6 ± 0.1 | 0.8 ± 0.1 | 6.8 ± 0.3 | 6.8 ± 0.4 | 6.0 ± 0.2 | 6.4 ± 0.2 |

TABLE 14a-continued

| | | | | | | | | | | | | |
|---|---|---|---|---|---|---|---|---|---|---|---|---|
| KIDNEYS (ng/mg tissue) | | | | | | | | | | | | |
| 1.5 h | 460 ± 33 | 404 ± 51 | 447 ± 46 | 535 ± 42 | 0.63 ± 0.05 | 0.57 ± 0.06 | 0.42 ± 0.03 | 0.84 ± 0.05 | 13 ± 0.9 | 15 ± 0.6 | 17 ± 1.8 | 14 ± 1.5 |
| 3 h | 199 ± 17 | 176 ± 11 | 176 ± 11 | 205 ± 34 | 0.38 ± 0.03 | 0.5 ± 0.03 | 0.3 ± 0.02 | 0.47 ± 0.03 | 14 ± 0.8 | 13 ± 1 | 17 ± 0.8 | 16 ± 0.8 |
| 6 h | 46 ± 9 | 45 ± 5 | 45 ± 5 | 43 ± 7 | 0.27 ± 0.03 | 0.26 ± 0.03 | 0.21 ± 0.01 | 0.26 ± 0.02 | 13 ± 0.6 | 15 ± 0.8 | 19 ± 0.8 | 14 ± 0.5 |
| SPLEEN (ng/mg tissue) | | | | | | | | | | | | |
| 1.5 h | 441 ± 46 | 310 ± 28 | 345 ± 22 | 486 ± 22 | Not Detected | Not Detected | Not Detected | Not Detected | 1.9 ± 0.2 | 1.4 ± 0.2 | 1.9 ± 0.2 | 2.2 ± 0.1 |
| 3 h | 251 ± 16 | 207 ± 21 | 228 ± 12 | 297 ± 50 | Not Detected | Not Detected | Not Detected | Not Detected | 1.7 ± 0.1 | 2.0 ± 0.2 | 1.6 ± 0.2 | 1.9 ± 0.2 |
| 6 h | 79 ± 16 | 67 ± 5 | 80 ± 14 | 98 ± 11 | Not Detected | Not Detected | Not Detected | Not Detected | 1.9 ± 0.2 | 1.4 ± 0.2 | 1.9 ± 0.2 | 1.6 ± 0.1 |

Less than CPT-11   More than CPT-11

TABLE 14b

Pharmacokinetics and pharmacodynamics of HyCAMP (13/60) and HyCAMP(26/60) and HyCAMP(55/60) formulation in rats

| | | | | | | | | | | | | |
|---|---|---|---|---|---|---|---|---|---|---|---|---|
| SMALL INTESTINES (ng/ml tissue) | | | | | | | | | | | | |
| 1.5 h | 109 ± 4 | 72 ± 4 | 60 ± 3 | 73 ± 3 | 2.2 ± 0.2 | 1.6 ± 0.1 | 1.2 ± 0.1 | 1.4 ± 0.1 | 1.7 ± 0.1 | 1.4 ± 0.1 | 1.5 ± 0.04 | 1.6 ± 0.1 |
| 3 h | 85 ± 7 | 60 ± 4 | 74 ± 4 | 76 ± 10 | 2.2 ± 0.2 | 1.4 ± 0.2 | 1.4 ± 0.1 | 1.9 ± 0.2 | 1.5 ± 0.07 | 1.4 ± 0.1 | 1.6 ± 0.02 | 2.0 ± 0.2 |
| 6 h | 43 ± 8 | 32 ± 3 | 32 ± 4 | 56 ± 8 | 2.2 ± 0.2 | 1.2 ± 0.1 | 1.3 ± 0.1 | 1.6 ± 0.2 | 1.2 ± 0.04 | 1.1 ± 0.2 | 1.6 ± 0.1 | 1.8 ± 0.2 |
| CONTENTS OF SMALL INTESTINES (ng/mg tissue) | | | | | | | | | | | | |
| 1.5 h | 492 ± 40 | 518 ± 40 | 540 ± 32 | 644 ± 22 | 11.9 ± 1.7 | 14.3 ± 2.4 | 10 ± 1.3 | 16.1 ± 1.8 | 9.5 ± 1.5 | 7.1 ± 3.4 | 11.5 ± 1.6 | 12.4 ± 3.7 |
| 3 h | 641 ± 88 | 670 ± 77 | 667 ± 38 | 697 ± 99 | 11 ± 2.8 | 14.4 ± 3.9 | 10.8 ± 2.3 | 12.7 ± 3 | 10.6 ± 2.0 | 8.5 ± 2.5 | 8.7 ± 0.6 | 10 ± 2.4 |
| 6 h | 245 ± 42 | 238 ± 43 | 387 ± 44 | 467 ± 44 | 9.1 ± 2.2 | 6.3 ± 0.5 | 14.7 ± 1.2 | 16.1 ± 1.7 | 7.7 ± 0.2 | Not Detected | 9.5 ± 0.7 | 6.9 ± 0.6 |
| LARGE INTESTINES (ng/mg tissue) | | | | | | | | | | | | |
| 1.5 h | 42 ± 4 | 26 ± 2 | 42 ± 4 | 2 ± 4 | 0.4 ± 0.09 | 0.3 ± 0.03 | 0.7 ± 0.3 | 0.2 ± 0.02 | 1.6 ± 0.1 | 1.3 ± 0.1 | 1.7 ± 0.1 | 1.2 ± 0.1 |
| 3 h | 47 ± 5 | 67 ± 8 | 47 ± 5 | 47 ± 5 | 1.7 ± 0.04 | 1.9 ± 0.2 | 1.8 ± 0.2 | 1.6 ± 0.2 | 1.4 ± 0.06 | 1.6 ± 0.;1 | 2.1 ± 0.2 | 1.7 ± 0.1 |
| 6 h | 115 ± 14 | 107 ± 12 | 91 ± 16 | 74 ± 12 | 4.4 ± 0.6 | 3.5 ± 0.2 | 2.7 ± 0.4 | 2.9 ± 0.5 | 1.4 ± 0.2 | 1.4 ± 0.1 | 2 ± 0.1 | 1.7 ± 0.1 |
| CONTENTS OF LARGE INTESTNES (ng/mg tissue) | | | | | | | | | | | | |
| 1.5 h | 146 ± 21 | 143 ± 18 | 175 ± 54 | 94 ± 12 | 1.3 ± 0.5 | 1.4 ± 0.4 | 2.3 ± 1.7 | 0.5 ± 0.2 | 8.7 ± 0.5 | 9.1 ± 0.5 | 8.7 ± 0.7 | 8.2 ± 0.6 |
| 3 h | 523 ± 109 | 676 ± 135 | 639 ± 66 | 386 ± 40 | 19.2 ± 4.8 | 21.1 ± 3.9 | 22.3 ± 2.8 | 16 ± 1.5 | 6.9 ± 0.4 | 10.6 ± 1.1 | 9.6 ± 1.0 | 10.9 ± 0.9 |
| 6 h | 1509 ± 268 | 2282 ± 235 | 1815 ± 182 | 1158 ± 85 | 45 ± 4.9 | 55.3 ± 7.3 | 41.9 ± 4 | 35 ± 4.1 | 9 ± 1.9 | Not Detected | 9.2 ± 0.3 | 11.3 ± 0.9 |

Less than CPT-11   More than CPT-11

Example 5

Determining the Effect of HA Molecular Weight and Concentration on Hepatic Beta-Glucuronidase Activity The effect of 860, 10 and <2 kDa HA on the activity of hepatic beta-glucuronidase were determined. The quantitation of the beta-glucuronidase units expressed as percentage change in beta-glucuronidase activity compared to the untreated tissue samples (Mean±SEM) are shown in Table 15. Whereas 10 and 860 kDa HA increased beta-glucuronidase activity increased by up to 36%, <2 kDa HA caused a marked inhibition of the enzyme by approximately 61%.

TABLE 15

| HA Conc. (μg HA/μg protein) | HA MW <2 kDa | HA MW 10 kDa | HA MW 860 kDa |
|---|---|---|---|
| 0.0 | 0 | 0 | 0 |
| 0.001 | −2 | −3 ± 1 | 0 ± 3 |
| 0.025 | −2 ± 1 | 0 ± 1 | 1 ± 2 |
| 0.05 | −1 ± 1 | 0 | 1 ± 1 |

TABLE 15-continued

| HA Conc. (μg HA/μg protein) | HA MW <2 kDa | HA MW 10 kDa | HA MW 860 kDa |
|---|---|---|---|
| 0.25 | −5 ± 1 | 5 | 1 |
| 0.5 | −11 ± 1 | 5 ± 1 | 3 ± 1 |
| 2 | −31 ± 2 | 7 ± 1 | 6 ± 2 |
| 4 | −45 ± 1 | 9 ± 1 | 10 ± 1 |
| 10 | −61 ± 1 | 24 ± 1 | 36 ± 7 |

Example 6

Effect of Hyaluronan on Both the Binary Excretion and Intestinal Exsorption of Irinotecan Hydrochloride (CPT-11) and its Metabolites, SN-38 and SN-38G Preparation HyCAMP™ and Irinotecan for Intravenous Dosing The 20 mg/mL stock of CPT-11 was diluted to 10 mg/mL in 0.9% (w/v) pyrogen-free injection grade NaCl and used to prepare individual irinotecan injections according to individual animal masses with the aim of delivering 30 or 60 mg/kg irinotecan.

A 10 mg/ml solution of HA in water for injection was used as the stock HA where injections were individually prepared according to animal masses in order to administer 26.6 mg/kg HA.

HyCAMP™ (hyaluronan formulated with irinotecan) was prepared immediately before injection. HyCAMP™ injections were then prepared according to individual animal masses with the aim of delivering 26.6 mg/kg of animal mass for HA and 60- and 30 mg/kg of animal mass for irinotecan.

Experimental Animal Model: In Situ Perfusion

Animal Specifications

Male Wistar rats were randomly divided into experimental groups (n=6/group). Treatment commenced when rats reach the desired starting weight of 280 to 340 g. The rats were fasted overnight with free access to drinking water before experiments.

In Situ Perfusion

Rats were anesthized by intraperitoneal (i.p) injection of ethyl carbamate (1.2 g/kg). The small intestine was exposed by placing a midline abdominal incision. The upper duodenum and the ileocecal junction were cannulated with a polyethylene tube. The small intestine was washed with saline at 37° C. and was perfused with lactated Ringer's solution at a rate of 1.3 ml/min from the duodenum through the small intestine to the ileocecal junction. Over a 2-3 min period, CPT-11 or HyCAMP™ was intravenously administered via the femoral vein at 30 mg/kg or 60 mg/kg. After the drug administration, a 5-min perfusion period was allowed to enable an equilibrium period. Blood samples were drawn (0.4 ml) at 0, 7.5, 15, 30, 60, 120, 180 and 240 min through a cannula introduced into the femoral artery. Perfusates were also collected at 0, 15, 30, 60, 120, 180 and 240 min from the ileal outflow. Bile samples were be collected at 0, 15, 30, 60, 120, 180 and 240 min from a cannula introduced into the common bile duct. Serum were immediately separated by centrifugation at 10,000 $g_{av}$ for 2 min at 4° C. and stored at −80° C. until assay. After completion of the blood, bile and perfusate collection, rats were sacrificed and tissues (liver, spleen, kidneys and intestines) removed and immediately stored at −70° C.

Analytical Methods for the Detection and Quantitation of the Total (Lactone and Carboxylate Forms) of CPT-11, SN-38 and SN-38G.

HPLC System and Running Conditions

Chromatographic separations were achieved by the use of a TSK gel ODS-80TS column (150×4.6 mm I.D.), and a mobile phase gradient. Mobile phase A and B are 0.075 M ammonium acetate buffer (pH6.4) and acetonitrile, respectively. Gradient elution were employed according to the following linear program of mobile phase B: time zero, 15%; 6 min, 30%; 9 min, 55%; 13 min, 55% and 15 min, 15%; where the flow rate was 1.1 ml/min, with a total run time of 20 min, and column temperature was maintained at 40° C. while the autosampler at 4° C. The fluorescence detector was set at an excitation wavelength of 355 nm and emission wavelength 515 nm.

Sample Preparation and HPLC Analysis

Serum, Intestinal Fluid and Bile

A HPLC system equipped with a fluorescence detector was used to determine CPT-11, SN-38 and SN-38G. Briefly, 50-100 μl of aliquots in polypropylene tubes were added to 100 ul of acetonitrile containing 0.2 μg/ml camptothecin as the internal standard. The tubes were vortex-mixed for 5 seconds and centrifuged at 8000 rpm for 2 min at −10° C. A portion of the supernatant (100 μl) was transferred to a fresh tube and 100 μl of phosphoric acid (pH 3.0) was added. The solution was briefly vortex-mixed and left at room temperature for 1 h to convert CPT-11, SN-38 and SN-38G to their lactone form each. A 20 μl aliquot was injected onto the above mentioned column.

Tissue Samples

For the analysis of tissue levels, tissue samples were homogenised in 15-fold volume (W/V) of cold methanol (−20° C.) and then centrifuged at 3000 rpm for 2 min at 4° C. The supernatant (100 μl) was transferred into a fresh tube, to which 70 μl of the mobile phase buffer will be added. The solution was briefly vortex-mixed and a 50 μl aliquot injected into the column.

Pharmacokinetic Analysis

CPT-11, SN-38, SN-38G and APC

The area under the serum concentration-time curves (AUC) of total CPT-11, SN-38 and SN-38G was calculated by the trapezoidal rule. The apparent biliary and intestinal clearance of CPT-11, SN-38, SN-38G and APC was calculated by dividing the overall amount of the drugs excreted into the bile or exsorbed into the perfusate during the 4 h by AUC from 0 h to 4 h, respectively. The unpaired t test were used to assess the pharmacokinetic parameters. A probability level of $p<0.05$ was considered significant.

Experimental Groups, Dosages and Frequency of Administration

Six Treatment Groups (n=6) Received the Following Drug Combinations and Stated Dosages. A Single Intravenous Injection of Each Formulation and Dosage is Cited Below;

Group 1: Irinotecan (30)

Group 2: HyCAMP™ (26.6/30): (formulation comprising HA and irinotecan)

Group 3: Hyaluronan (26.6) administered 15 minutes prior to irinotecan (30)

Group 4: Irinotecan (60)

Group 5: HyCAMP™ (26.6/60): (formulation comprising HA and irinotecan)

Group 6: Hyaluronan (26.6)

The dose administered was calculated using the following formulas:

$$\text{VOLUME INJECTED (mL)} = \text{mass of syringe before injection (g)} - \text{mass of syringe after injection (g)}$$

$$\text{MASS INJECTED (mg)} = \text{concentration of drug}/HA \text{ in injection solution (mg/mL)} \times \text{volume injected (mL)}$$

$$\text{DOSE ADMINISTERED (mg/kg)} = \frac{\text{mass injected (mg)} \times 1000}{\text{rat mass (g)}}$$

Serum Concentration after Intravenous Dosing with 30 Mg/Kg Irinotecan

Prior to HPLC analysis all extracted samples underwent acidification. All results presented, therefore, represent the lactone form of CPT-11, SN-38 and SN-38G.

Biliary Excretion Profiles, Irinotecan (30)

Following dosing of rats with irinotecan (30), HyCAMP™ (26.6/30) or HA (26.6) 15 minutes before irinotecan (30), perfusates were collected at defined time points from the ileal outflow and also from a cannula introduced into the common bile duct were analysed for CPT-11, SN-38, SN-38G and APC.

Biliary Excretion of CPT-11

Figure 5A:
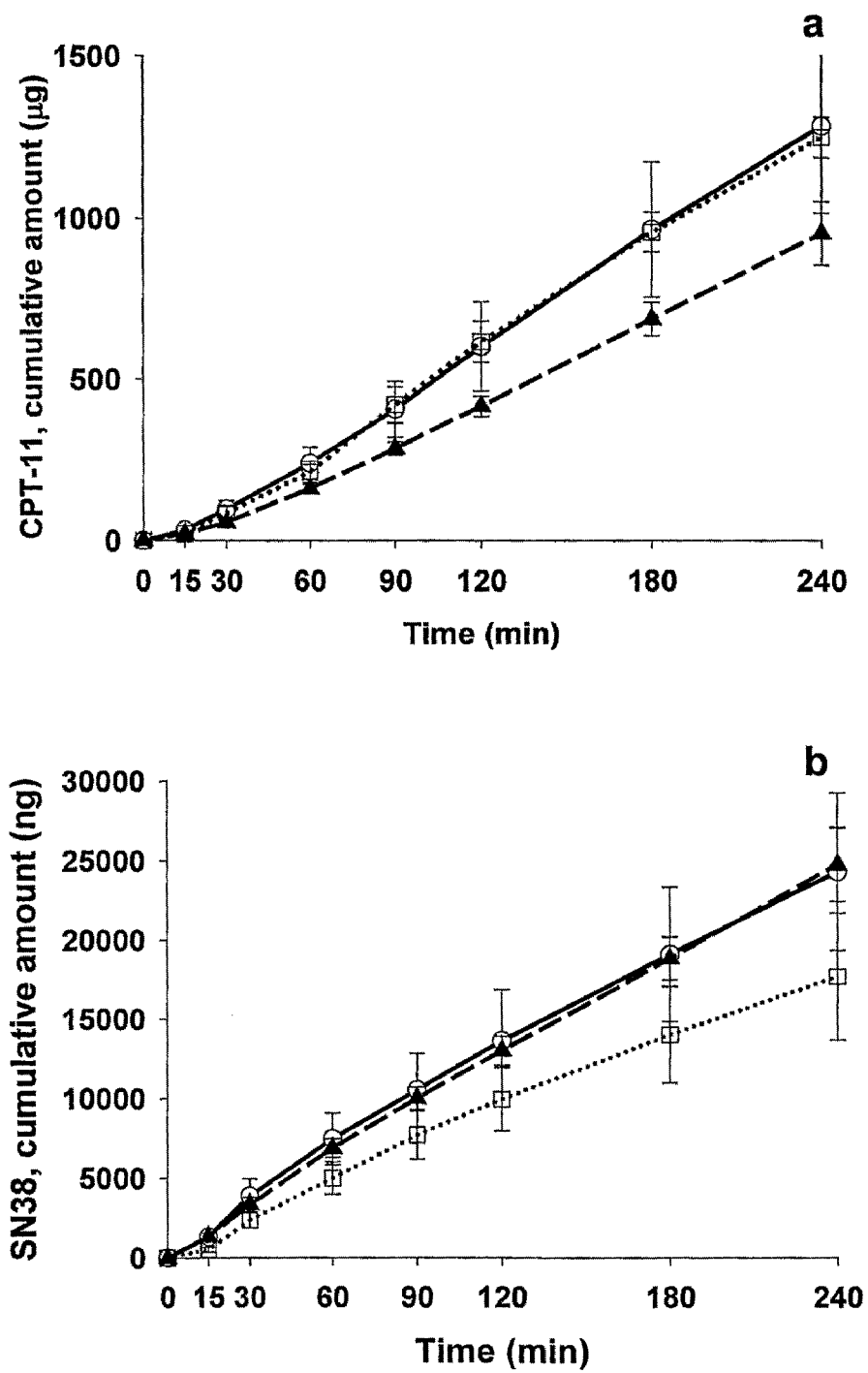
FIG. 5 is a graphical representation demonstrating the cumulative biliary excretion of CPT-11 (a), SN-38 (b), SN-38G (c), and APC (d) following a single intravenous injection of irinotecan (30: open circles), HyCAMP™ (26.6/30: filled triangles and HA (26.6) 15 minutes prior to irinotecan (30: open squares). Each value represents the average±SEM, where n=6 unless otherwise stated. (a) p=<0.05 compared with irinotecan group.

FIG. 5a shows the cumulative biliary excretion rates of CPT-1. There was a trend towards less CPT-11 being excreted in rats receiving HyCAMP™ but these differences were not significant (FIG. 5a). Biliary excretion of CPT-11 in rats dosed with HA then irinotecan was comparable to that observed in the CPT-11 treated group (FIG. 5a). The difference between the HyCAMP™ and HA+irinotecan group was statistically significant ($p=<0.05$) between 90- and 240-minutes where the formulation HyCAMP™ resulted in a lower cumulative biliary excretion of CPT-11.

Biliary Excretion of SN-38

Figure 5B:
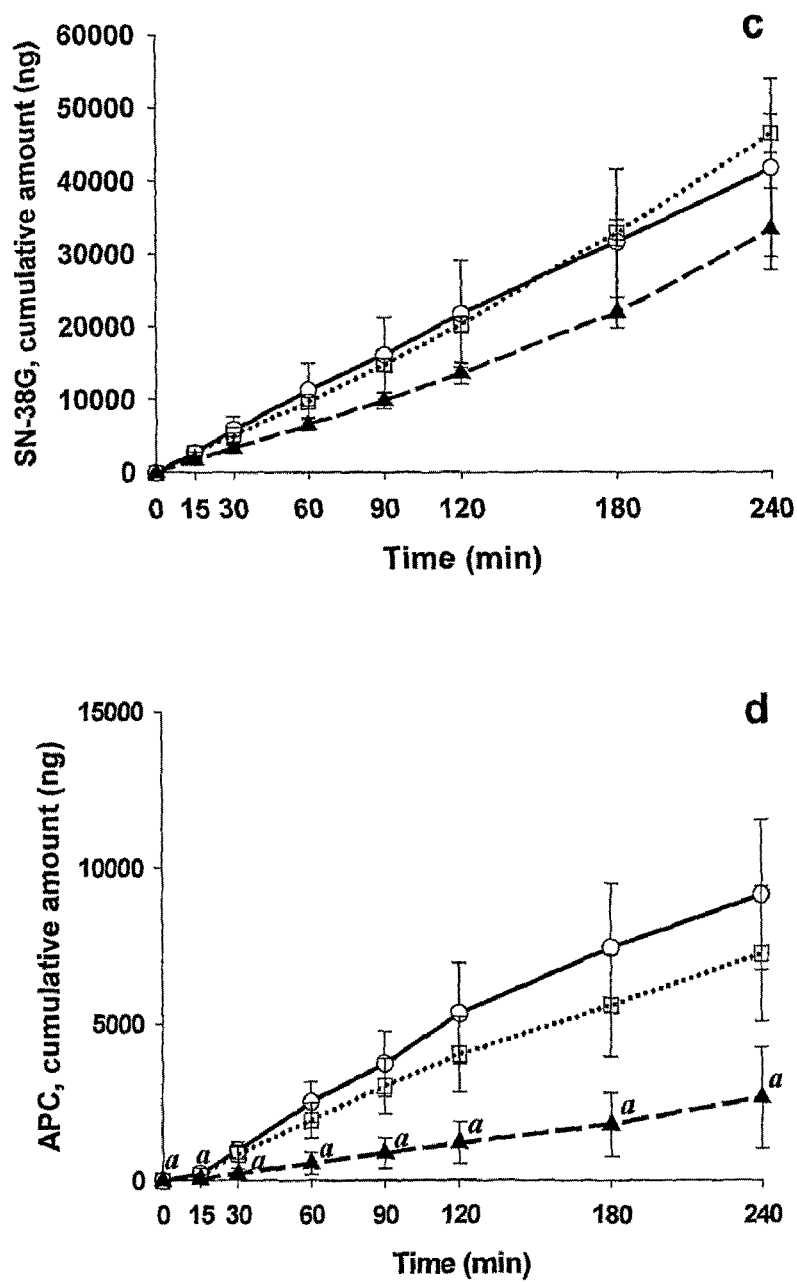

Similar biliary excretion profiles in both HyCAMP™ and irinotecan only treatment groups for SN-38 were observed (FIG. 5b). Where rats were dosed with HA prior to CPT-11, after 15 minutes post dose the amount of SN-38 was approximately 2.5-fold less when compared with the other treatment groups (FIG. 5b: 1300 ng CPT-11 group cf 522 HA+CPT-11 group; $p=<0.05$). The lower cumulative biliary excretion of SN-38 in this group was a consistent trend but was not significant in all subsequent time points.

Biliary Excretion of SN-38G

When comparing the biliary excretion of SN-38G, there was a trend for the HyCAMP™ treated rats to contain less inactive metabolite to that observed in the rats receiving irinotecan alone (FIG. 5c). These differences were not considered significant. Biliary excretion of SN-38G in rats dosed with HA prior to irinotecan was comparable to the CPT-11 treatment group (FIG. 5c). Interestingly, the difference between the HyCAMP™ and HA administered before CPT-11 11 treatment groups was significant between 30- and 240 minutes post dosing where the HyCAMP™ group contained less SN-38G in the bile (FIG. 5c).

Biliary Excretion of APC

The administration of HyCAMP™ significantly reduced the biliary excretion of APC (approximately 5-fold less) to that observed in rats dosed with CPT-11 alone (FIG. 5d). This correlates with the low serum levels of APC observed in this treatment group. At all time points these results were significant ($p=<0.05$). This was a similar trend in rats dosed with HA prior to CPT-11 where a trend towards less biliary excretion of APC was observed but was not considered significant when compared with the irinotecan treated rats (FIG. 5d). The difference between biliary excretion of APC in HyCAMP™ and HA administered before CPT-11 treatment groups was significant at 30 and 60 minutes post dosing.

Biliary Excretion Profiles, Irinotecan (60)

Biliary Excretion of CPT-11

Figure 6A:
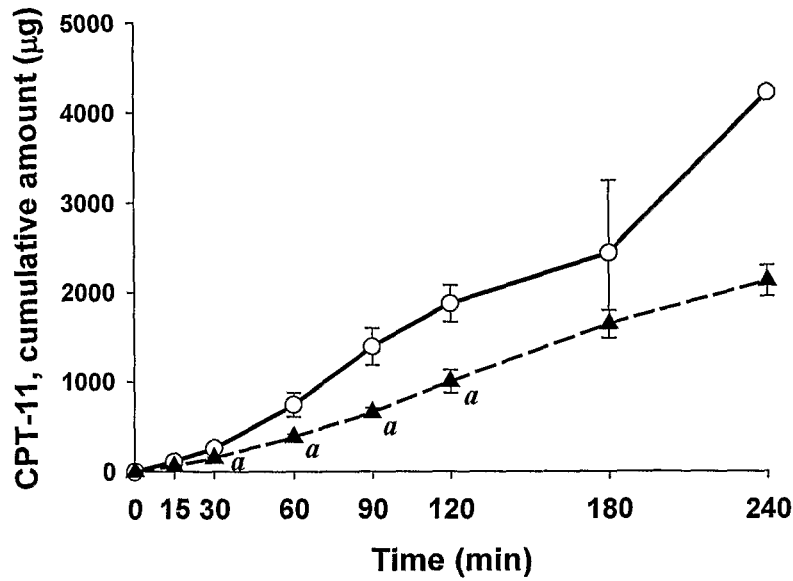
FIG. 6 is a graphical representation demonstrating the cumulative biliary excretion of CPT-11 (a), SN-38 (b), SN-38G (c), and APC (d) following a single intravenous injection of irinotecan (60: open circles), HyCAMP™ (26.6/60: filled triangles). Each value represents the average±SEM (a): p=<0.05 compared with irinotecan group.
Figure 6A:
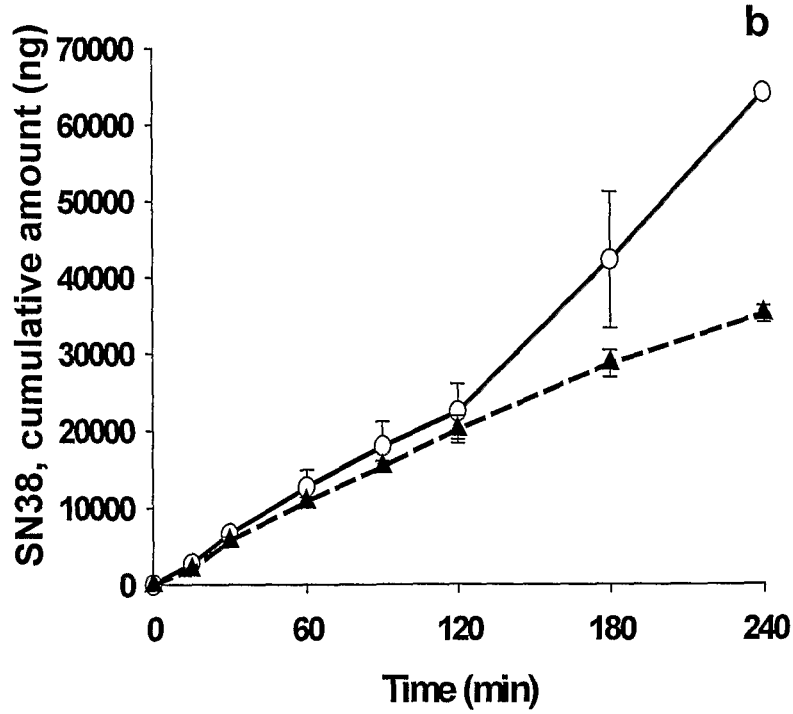

The parent compound, CPT-11 represented the largest proportion of injected material to be excreted via the bile in both irinotecan and HyCAMP™ treated animals. In rats dosed with HyCAMP™ the cumulative biliary excretion was approximately half of that observed in animals dosed with irinotecan (FIG. 6a; 1388 μg CPT-11 cf 653 μg HyCAMP™ at 90 minute time point: $p=<0.05$). The difference between the treatment groups was significant between 30- and 180 minutes.

Biliary Excretion of SN-38

Figure 6B:
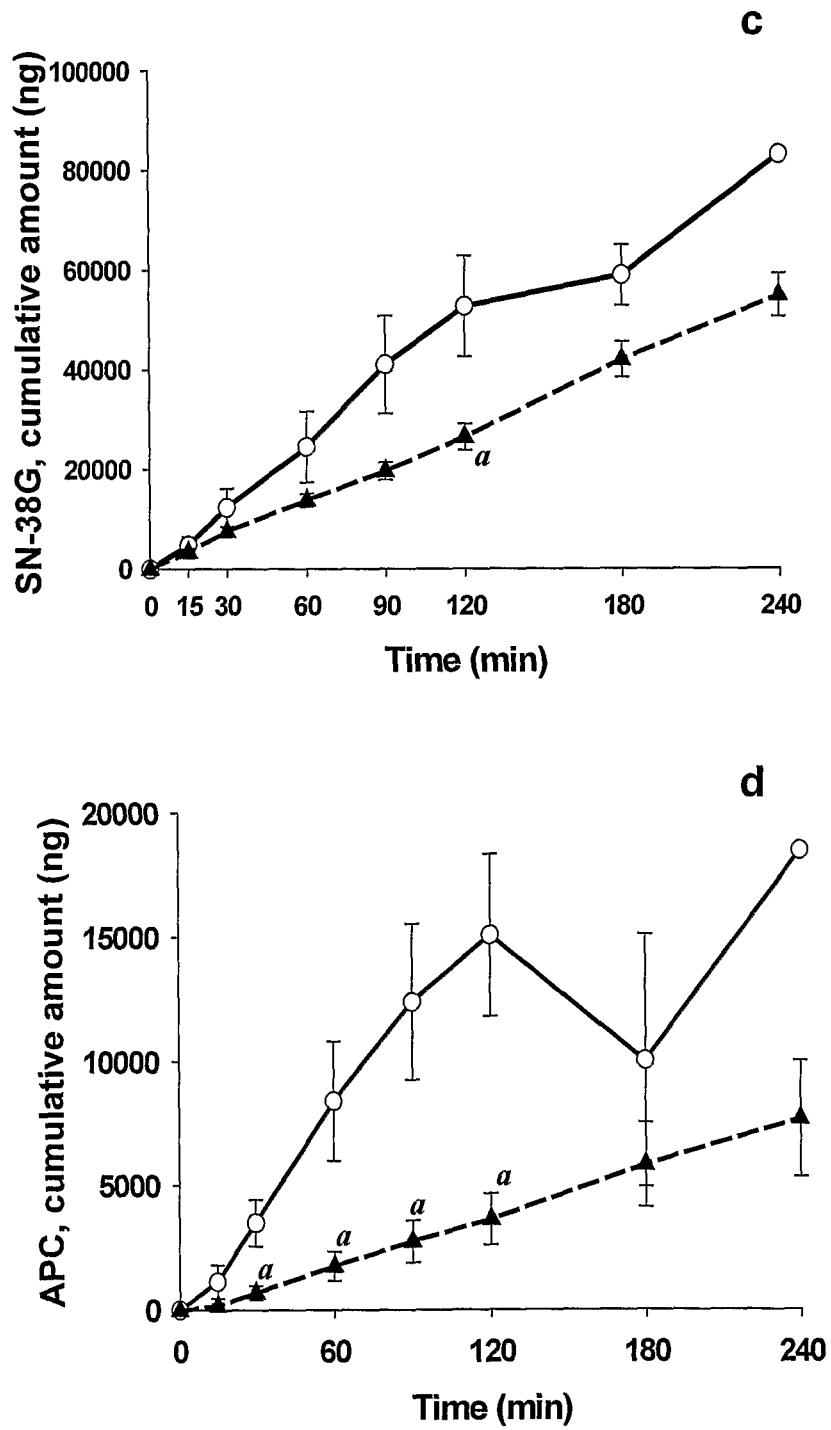

Biliary excretion of the active metabolite, SN38 was comparable irrespective if rats were dosed with HyCAMP™ or irinotecan. (FIG. 6b). The value at the last time point represents only one rat therefore comparative comment between SN38 levels at 240 minute with the HyCAMP™ values is not possible.

Biliary Excretion of SN-38G

The biliary excretion of the inactive metabolite, SN-38G was affected when irinotecan was administered as HyCAMP™ (FIG. 6c). Although only significant at 120 minute time point where approximately 2-fold less SN-38G was excreted, the overall trend in rats injected with HyCAMP™ was less SN-38G being excreted via the biliary route.

Biliary Excretion of APC

As was observed in the 30 mg/kg dosing experiments, the most pronounced effect of HyCAMP was on the biliary excretion of the inactive metabolite APC (FIG. 6d), where approximately 5- to 2-fold less APC was observed in the HyCAMP rats when compared with those receiving irinotecan alone. The difference between the treatment groups was significant between 30- and 120 minutes ($p=<0.05$). This profile correlates with the low serum levels of APC observed in this treatment group.

Intestinal Exsorption, Irinotecan (30)

Intestinal Exsorption of CPT-11 and Metabolites

The intestinal cumulative exsorption represents the amount of CPT-11 and its metabolites that enters the intestinal lumen via exsorption from the blood via the intestinal membrane. It is within this mode of secretion that HyCAMP™ (26.6/30) has its most pronounced effect not only on CPT-11 but also with SN-38, SN-38G and APC. These figures are presented in FIGS. 7 a, b, c and d respectively.

Intestinal Exsorption of CPT-11

Figure 7A:
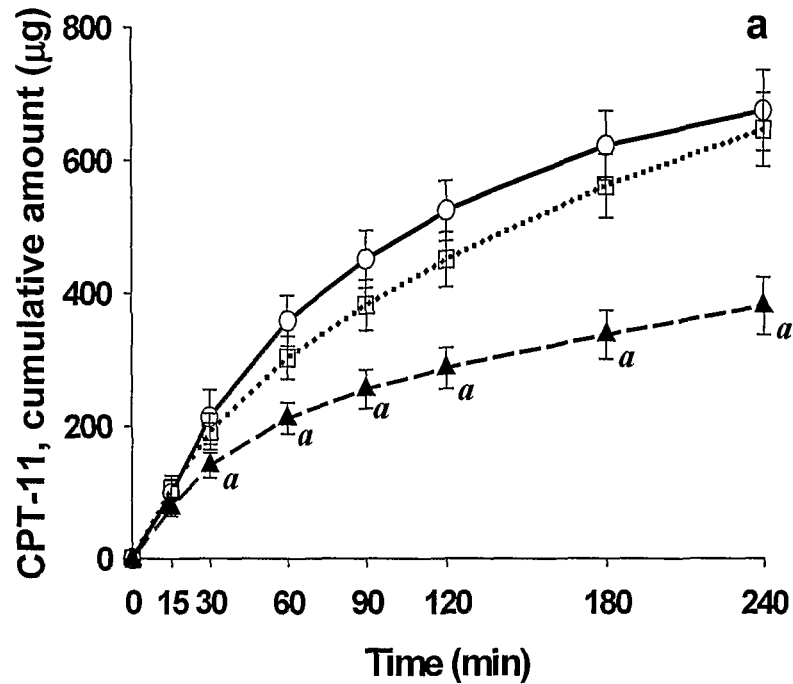
FIG. 7 is a graphical representation demonstrating the cumulative intestinal exsorption of CPT-11 (a), SN-38 (b), SN-38G (c), and APC (d) following a single intravenous injection of irinotecan (30: open circles), HyCAMP™ (26.6/30: filled triangles and HA (26.6) 15 minutes prior to irinotecan (30: open squares). Each value represents the average±SEM, where n=6 unless otherwise stated. (a) & (b) p=<0.05 compared with irinotecan group; (c) p=<0.05 compared with HA 15 mins before irinotecan.
Figure 7A:
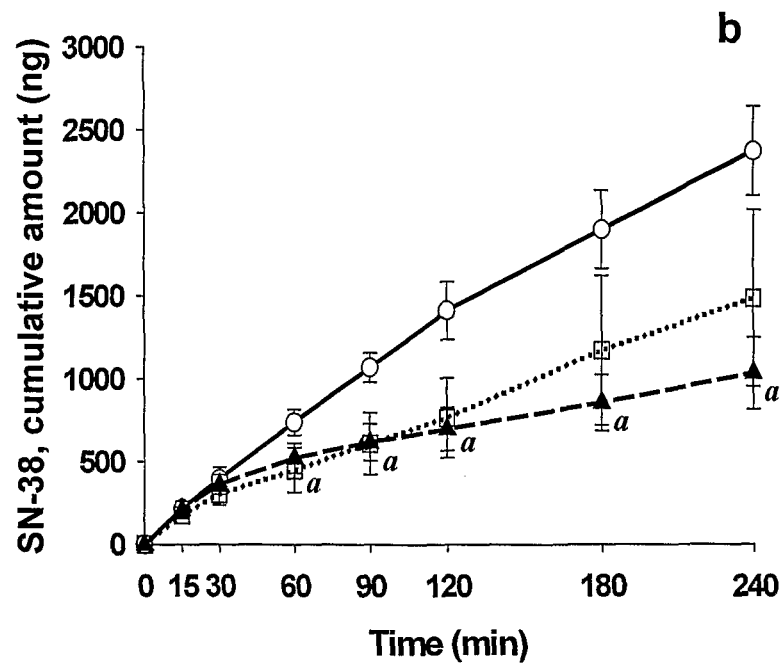

The amount of CPT-11 entering the intestinal lumen in rats receiving HyCAMP™ was nearly 2-fold less to that observed in the CPT-11 dosed animals (FIG. 7a: 120 min 525 μg CPT-11 cf 287 μg HyCAMP™). With the exception of the first two time points all remaining points were significant. CPT-11 represented the largest proportion of all metabolites quantitated in the intestinal lumen. In order for HA to exert this effect on the intestinal exsorption of CPT-11 it has to be administered in the form of HyCAMP™. This statement is substantiated by the data derived from rats that were dosed with HA prior to irinotecan where a similar profile to the intestinal secretion of CPT-11 was observed with rats receiving irinotecan alone (FIG. 7a). The difference between CPT- 11 intestinal secretion in HyCAMP™ and HA+CPT-11 was significant from 60 minutes until experimental end-point (FIG. 7a).

Intestinal Exsorption of SN-38

Figure 7B:
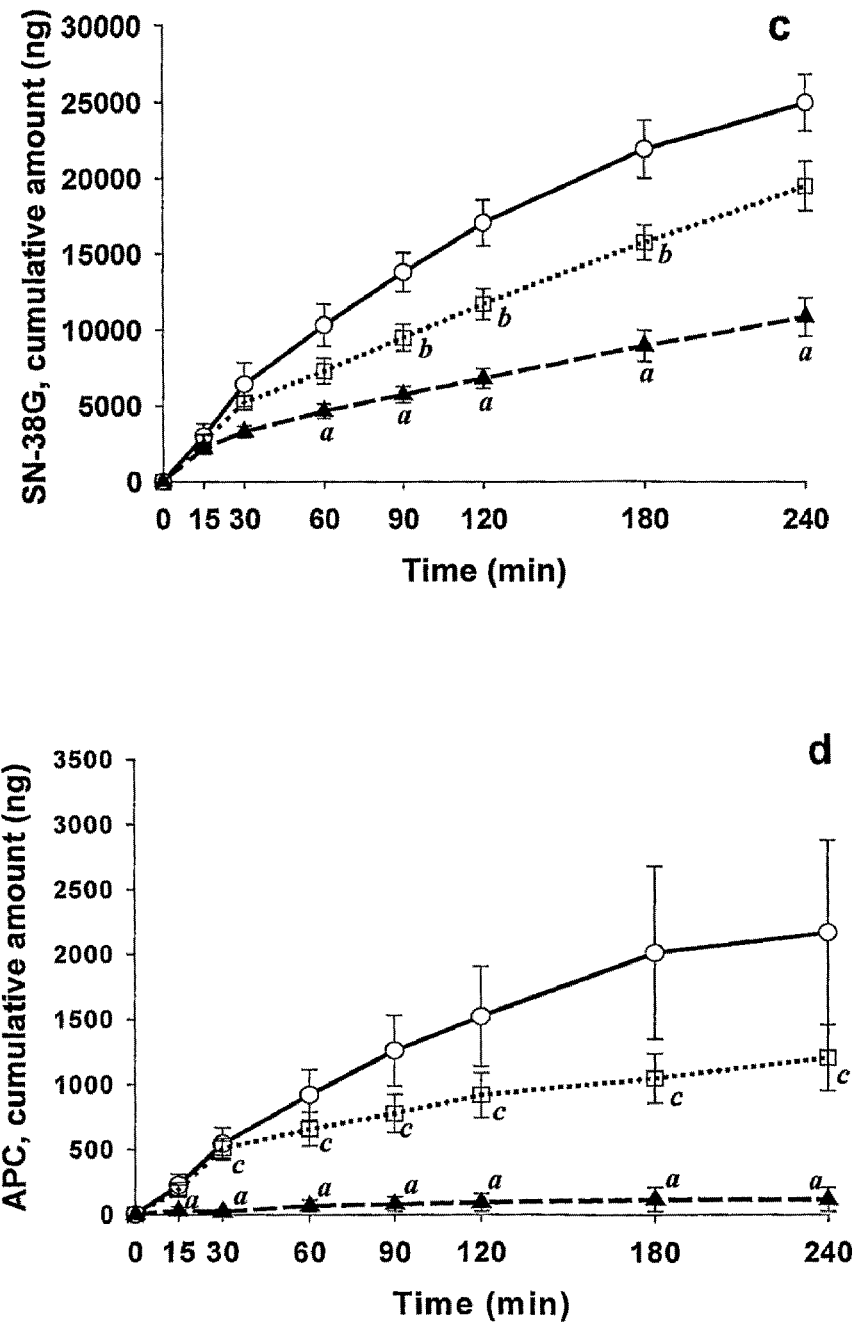

When CPT-11 was administered in the form of HyCAMP™ approximately 2-fold less of the active metabolite, SN-38 was collected in the ileal perfusate when compared with rats dosed with irinotecan (FIG. 7b: 120 min; 1411 ng/min CPT-11 cf 696 ng/min HyCAMP™: p=<0.05). The differences between the two treatment groups were significant between 60- and 240 min of the experiment. This was a similar trend in rats that were dosed with HA prior to receiving irinotecan, however the differences between this groups and the irinotecan treatment groups were not significant (FIG. 7b). The intestinal exsorption data for SN-38 from both HyCAMP™ and HA+CPT-11 treated rats were considered comparable.

Intestinal Exsorption of SN-38G

The amount of the inactive metabolite SN-38G characterised in the intestinal lumen from rats dosed with irinotecan was significantly different to that observed in rats receiving HyCAMP™ (FIG. 7c). Specifically, the amount of SN-38G found in the HyCAMP™ treated rats was 2- to almost 3-fold less when compared with the irinotecan group (FIG. 7c: 180 min; 22 µg irinotecan group cf 9 µg HyCAMP™: p=<0.05). The difference between the treatment groups was significant between 60- to 240 min of the experiment. Intestinal exsorption of SN-38G was still affected in rats that were dosed with HA prior to irinotecan (FIG. 7c). The difference between rats receiving this method of administration to those injected with irinotecan alone was significant from 90 minutes until experimental end-point (FIG. 7c: 180 min; 22 µg irinotecan group cf 15 µg HA+CPT-11: p=<0.05). The greatest degree in modulation of SN-38G intestinal exsorption was observed in the HyCAMP™ group which was significantly less at all time points when compared with rats dosed with HA prior to irinotecan.

Intestinal Exsorption of APC

As was observed in the serum, and biliary excretion profiles, HyCAMP™ exerted its most pronounced effect on the intestinal exsorption of APC, where the fold difference between the two treatment groups was approximately 14- to 27-fold less APC in rats receiving HyCAMP™ (see FIG. 7d: 1500 ng irinotecan gp cf 92 ng HyCAMP™ group). The difference between these two groups was significant at all experimental time points. Again, where HA was administered prior to irinotecan there was a trend towards less APC accumulating in the intestinal lumen but was not significant Intestinal Exsorption, Irinotecan (60)

Intestinal Exsorption of CPT-11

CPT-11 represented that largest proportion of injected material which entered the intestinal lumen via exsorption from the blood via the intestinal membrane (FIG. 8a). The amount of CPT-11 entering the intestinal lumen in this manner was comparable between treatment groups.

Intestinal Exsorption of SN-38

At the initial time points of 15 and 30 minutes there was approximately 2-fold greater the amount of SN-38 entering the intestinal lumen in rats receiving HyCAMP compared with rats receiving irinotecan alone (FIG. 8b). This was a consistent trend until 180 minutes post dose but the difference between the two groups was not significant. This is particularly interesting when one considers the elevated levels of SN-38 in blood circulation in rats dosed with HyCAMP™, which was found to significantly higher when compared with the irinotecan treated rats.

Intestinal Exsorption of SN-38G

In the case of the inactive metabolite, SN-38G similar values were found in the intestinal lumen when comparing both treatment groups, although at the later time points (180 minutes) less SN-38G was observed in rats receiving HyCAMP™ (FIG. 8c). These values were not significant.

Intestinal Exsorption of APC

Consistent with previous observations the intestinal secretion of APC in rats receiving HyCAMP™ was significantly lower (approximately 3- to 5-fold less) at all subsequent time points 15 minutes post injection (FIG. 8d).

Discussion of Data

This study describes the effects of hyaluronan on the pharmacokinetics of CPT-11, SN-38, SN-38G and APC. In addition to these parameters, the rates at which these compounds are excreted via the biliary route and exsorbed in to the intestinal lumen from the blood stream have also been evaluated. This study was undertaken to provide possible insights into the means by which hyaluronan reduces the gastrointestinal tract toxicity profile of irinotecan. Hyaluronan/irinotecan formulations reduce the gastrointestinal tract toxicity when compared with rats receiving the same dosage of irinotecan alone. Histopathological examination clearly demonstrated less severe lesions in the small and large intestine. Specifically, regions of the ileum and caecum in rats were less affected when treated with formulations of the invention than those rats receiving irinotecan alone. In addition to the preclinical observations, reduction in GI-tract toxicity was also observed in patients in a recently completed Phase I clinical trial.

Both CPT-11 and SN-38 have an α-hydroxy-δ-lactone ring, which can undergo reversible and pH-dependent hydrolysis and lactonization reactions of each compound in aqueous solution. The closed lactone form predominates under acidic conditions, and the open carboxylate form predominates under alkaline conditions. The inter-conversion of these two forms in both CPT-11 and SN-38 has been studied, where it has been shown at pH7.6 and 5.6 that the percentage of camptothecin present in the lactone- and carboxylate form is 11.7- and 90.8% respectively. In addition, the percentage of lactone and carboxylate forms of CPT-11 and SN-38 at pH7.4 and 6 was shown to be 10- and 90% respectively[52]. Therefore at the prevailing pH in blood (~7.4) the equilibrium would favour hydrolysis to open the lactone ring and yield the carboxylate form.

We have conducted in vitro studies examining the effects of different molecular weights of HA on the following enzymes involved in the biotransformation of CPT-11;

1. Carboxylesterase
2. beta-glucuronidase

Tissue homogenates of the liver and the GI-tract were used as the source of each enzyme. These studies clearly demonstrated that HA did not affect the activity of carboxylesterase but <2 kDa HA fragments inhibited the activity of beta-glucuronidase in both hepatic and GI-tract extracts at physiologically relevant concentrations. After hepatic activation of CPT-11, the presence of excess HA fragments (<2 kDa) could inhibit the deconjugation of SN-38G back to SN-38, resulting in less SN-38 being excreted into the GI tract via the biliary route. In addition to this mechanism, inhibition of beta-glucuronidase in the lumen of the GI tract would prevent the generation of SN-38 from SN-38G.

Hyaluronan of all molecular weights tested did not modulate carboxyesterase activity (neither an inhibitory nor stimulatory effect was observed). These findings are important to remember when considering the results of this study in light of the lowered serum levels of the inactive metabolite APC.

Specifically, hyaluronan has modulated and/or inhibited the oxidative metabolism of CPT-11 through the cytochrome P450 pathway that has resulted in less formation of the inactive metabolite of CPT-11, APC.

In formulations containing a higher dose of irinotecan (60), HyCAMP™ (26.6/60) treatment caused a similar trend that was more noted with respect to serum SN-38 levels and the formation of APC. Despite similar levels of CPT-11 and SN-38G when compared to rats treated with irinotecan alone, the hyaluronan/irinotecan treated rats displayed significantly elevated levels of SN-38 that correlated with significantly less APC. This result reinforces that observed at the lower dose and indicates that administration of the irinotecan/hyaluronan formulation has perturbed the cytochrome P450 oxidative pathway in such a manner that CPT-11 is shunted into the carboxylesterase pathway resulting in more SN-38 being produced.

Compared with rats dosed only with irinotecan (30), rats dosed with the formulation of hyaluronan/irinotecan (26.6/30) displayed some subtle differences at earlier time points in relation to the serum-time course experiments. Specifically, less CPT-11 was observed after the equilibration (5 min) period following the injection that correlated with a transient increase in the levels of SN-38. Although subsequent time points were not significant, there was a trend for lower CPT-11 and higher SN-38 levels in the serum when comparing this data with rats receiving irinotecan alone. Beyond the bioactivation of CPT-11, HA caused a more obvious effect on the levels of SN-38G formed by conjugation of SN-38 to a glucuronide moiety, the detoxification step catalysed by the uridine diphosphate glucuronosyltransferases (UGT). The difference between hyaluronan/irinotecan and irinotecan only treatment groups was significant up to 30 minutes post dose. This effect on a reduced formation of SN-38G is only observed in rats receiving hyaluronan/irinotecan formulations. Interestingly, if we examine the serum time course profile for SN-38G in rats that were dosed with HA (26.6) 15 minutes prior to receiving irinotecan the level of SN-38G increases initially then remains in plateau up to 120 minutes post dose whereas rats dosed with irinotecan have a similar initial increase that drops down to levels comparable to that in the animals treated with hyaluronan/irinotecan formulations in which the hyaluronan and irinotecan are dosed together. This represents inhibition of hepatic beta-glucuronidase where the HA administered 15 minutes prior to irinotecan and has caused saturation kinetics of the enzymes involved in the catabolism of HA, particularly beta-glucuronidase. Conversely, hyaluronan/irinotecan dosed rats do not display this trend which may reflect that HA in the form of a combined formulation has interfered with the glucuronide conjugation reaction of SN-38 to SN-38G catalysed by UGTs.

At the higher dose of hyaluronan/irinotecan (26.6/60), the amount of CPT-11 and SN-38G being excreted in to the gut was approximately half that observed in the rats dosed with irinotecan alone. These are important observations where this route of elimination is responsible for causation of GI-tract toxicity by the following means;
1. SN-38 excreted via the bile into the gut induces GI-tract impairment
2. De-conjugation of glucuronide moiety from SN-38G to yield SN-38 (after biliary excretion of SN-38G) by virtue of beta-glucuronidase activity from resident intestinal microflora
3. Intestinal carboxlyesterase activity converts CPT-11 to SN-38[41].

When considering this pathway of excretion, the formulations of the invention have lowered the amount of CPT-11 and SN-38 and SN-38G entering the GI-tract. It follows, therefore, that in doing so one would expect less generation of SN-38 from both carboxylesterase activity and de-conjugation of SN-38G to SN-38 from beta-glucuronidase activity from resident microflora in the intestinal lumen.

Cyclosporin A is a known inhibitor of both P-gp and cMOAT, and causes a reduction in the excretion of CPT-11 and SN-38 in the bile after dosing with irinotecan. A similar reduction in the excretion of CPT-11 and SN-38 in the bile is observed after dosing with hyaluronan/irinotecan formulations and it is believed that hyaluronans modulate the activity of cMOAT and/or P-gp in the biliary membrane. This is supported by the observation that in hyaluronan/irinotecan (26.6/60) treated rats, the serum SN-38 levels were much higher when compared with the irinotecan dosed animals, yet biliary excretion in the hyaluronan/irinotecan animals for CPT-11 and SN-38G were reduced and the level of SN-38 excreted via this route was comparable to the animals receiving irinotecan alone. As the serum CPT-11 levels were relatively comparable, the increase serum SN-38 levels observed may be due to decreased biliary excretion.

The pharmacokinetic interference observed in these experiments potentially indicate that HA has inhibited the hepatic CYP3A4 pathway involved in CPT-11 metabolism, preferentially shunting the parent drug into SN-38.

Hyaluronan reduces the amount of CPT-11, SN-38 and SN-38G being exsorbed in to the lumen of the GI-tract. This is highlighted when comparing serum levels of CPT-11, SN-38 and SN-38G with their intestinal exsorption profiles. Where serum levels of CPT-11 are essentially comparable between treatment groups and serum SN-38 was moderately increased, hyaluronan/irinotecan formulations reduced the amount of the parent drug and the toxic metabolite entering the gut via this pathway by approximately half. This mechanism of reduced transport is only affected when CPT-11 is administered in the form of a formulation of the present invention. Low levels of SN-38G observed in the hyaluronan/irinotecan treatment group partly explain the lower levels of this inactive conjugate entering the GI-tract lumen, yet rats receiving HA prior to irinotecan displayed a trend towards more SN-38G in the serum when compared with the irinotecan treated rats. In this context this group of rats still display significantly less SN-38G entering the gut lumen from blood circulation and indicate that HA is affecting this transport mechanism. The inactive metabolite APC was affected in a similar manner but probably reflects the low levels found in the serum to begin with.

At the higher dose of hyaluronan/irinotecan (26.6/60), intestinal exsorption of CPT-11 and its metabolites were essentially non remarkable with the exception of APC. The most obvious altered serum metabolite in the hyaluronan/irinotecan group was SN-38 which was significantly increased, yet intestinal exsorption of SN-38 was comparable between treatment groups.

Tissue distribution of CPT-11 and its metabolites could only be compared in the treatment groups receiving 30 mg/kg irinotecan due to the toxic related deaths observed in rats receiving irinotecan (60) where only one rat survived until experimental end-point. In contrast, rats receiving hyaluronan/irinotecan (26.6/60) all survived and highlights that this formulation is not as acutely toxic when the drug is administered by itself. Irinotecan loading in the spleen was significantly lower in rats receiving hyaluronan/irinotecan or HA 15 minutes prior to irinotecan. Interestingly, SN-38 could not be detected in the spleen in rats receiving irinotecan alone despite displaying the larger quantities of CPT-11. In this context, we have previously demonstrated that rats chronically exposed to hyaluronan/irinotecan (26.6/60) display significantly smaller spleens at experimental end-point when compared with rats receiving irinotecan alone.

CPT-11 loading in all remaining organs was comparable and therefore indicates that hyaluronan is not exerting a marked effect in the biodistribution of the drug to the liver, kidney, intestine and lungs and is therefore not a potential mechanism by which HA exerts a protective effect over the GI-tract induced toxicity following irinotecan treatment.

The quantities of SN-38 found in the spleen and lung were all significantly greater where rats had been dosed with hyaluronan/irinotecan. SN-38 could not be detected in the spleen or lung after dosing with irinotecan alone.

More importantly is the distribution of CPT-11 and metabolites in the intestine which are relatively comparable across all treatment groups, highlighting that the mechanisms by which hyaluronan/irinotecan exerts its protective effect over irinotecan induced GI tract toxicity is in the principle route of elimination via the bile and also in intestinal exsorption.

Example 7

Determining the Effect of the Molecular Weight and Concentration of Hyaluronan on the Activity of Endogenous Beta-Glucuronidase in Tumor Cells In Vitro Test and Control Articles
Hyaluronan:
  Batch number: HA10509 (Biological therapies; Modal MW 860 kDa as determined by the Institute of Drug Technology using intrinsic viscosity measurements).
  Batch number: 150103E/3/240/S (CPN Ltd. Modal MW 10 kDa)
  Hyaluronan <2 kDa (generated in HA Laboratory by hyaluronidase digestion)
Determining the Effect of HA Concentration and Molecular Weight on Endogenous Tumour Cell Beta-Glucuronidase In Vitro
Preparation of Sample Stocks of the tumor cell lysates (0.8 mg protein/ml) were prepared from the original cell lysates. The hyaluronan stock of 10 mg/ml (10 kDa & 860 kDa) was diluted with potassium phosphate buffer to achieve 8 mg/ml, 3.2 mg/ml, 1.6 mg/ml, 0.4 mg/ml, 0.2 mg/ml, 0.04 mg/ml, 0.02 mg/ml and 0.0008 mg/ml of hyaluronan. The 25 mg/ml of <2 kDa HA was diluted further with potassium phosphate buffer to achieve 8 mg/ml, 3.2 mg/ml, 1.6 mg/ml, 0.4 mg/ml, 0.2 mg/ml, 0.04 mg/ml, 0.02 mg/ml and 0.0008 mg/ml of hyaluronan. The assay samples were prepared by aliquoting 125 µl of the different dilutions of hyaluronan to an Eppendorf tube containing 125 µl of 0.8 mg protein/ml cell lysates of the following cell lines; HCT-116, LIM-1215, LIM-2099, SK-CO1, SW-1222, HT-29, SW-620, MSTO-211H, MDA-MB-468 and MDA-MB-435. The samples were thoroughly mixed by repeated invert mixing (~20 times) followed by an overnight incubation at 37° C. On completion of the incubation, the samples were thoroughly mixed by repeated invert mixing (~20 times) after which the beta-glucuronidase was quantified using the 96-well-plate method.

Beta-Glucuronidase Assay: 96-Well-Plate Method

The assay was performed in the wells of a black clear-bottom 96-well-plate where 50 µL of the tumour cell lysates (20 µg protein) were added to the wells and 50 µL of 75 mM of potassium phosphate buffer was used as the control blanking well. This addition was followed by the addition of 50 µL of 500 µM of 4-Methylumbelliferyl-β-D-Glucuronide (4-MUBG) substrate which was added to each test well and the blank well. The plates were incubated at 37° C. for exactly 1 hour. On completion of the incubation, 50 µL of stop buffer was added and the plate was read at 350 nm excitation and 450 nm emission on a Fluostar Optima plate reader.

Figure 9:
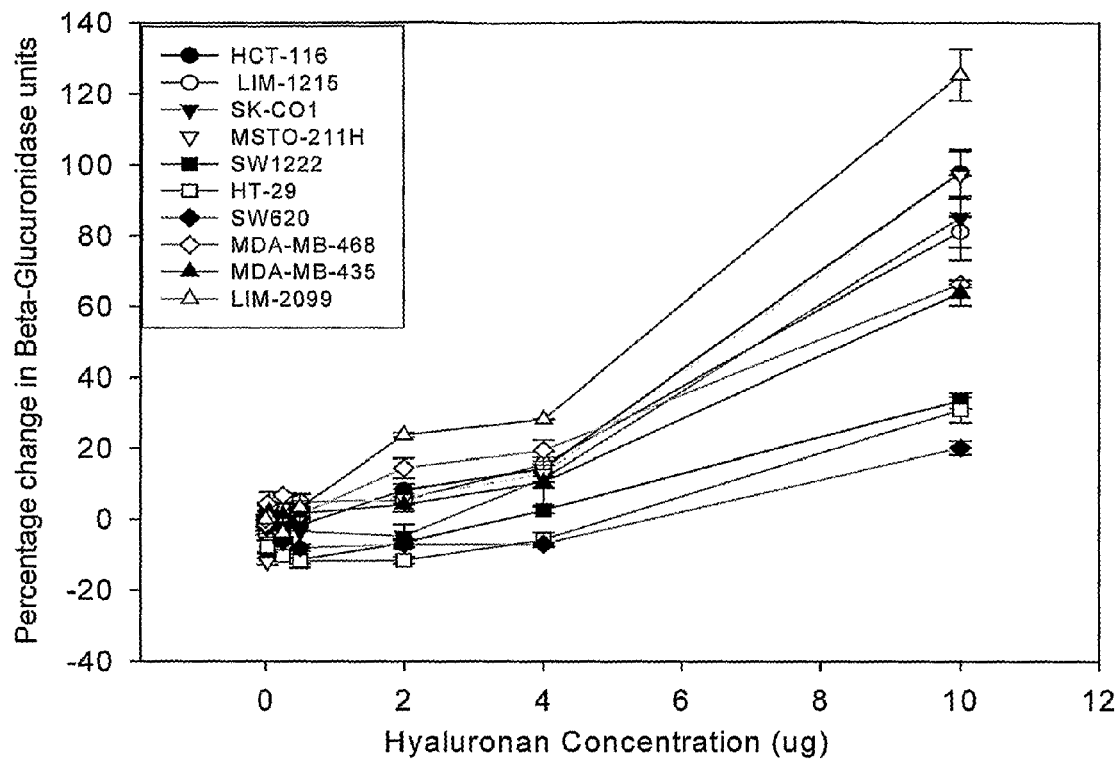
FIG. 9 is a graphical representation showing the effect of 860 kDa HA on the activity of tumour cell endogenous beta-glucuronidase

Determining the Effect of Hyaluronan Molecular Weight and Concentration on Endogenous Tumour Beta-Glucuronidase Activity Evaluation of 860 kDa Hyaluronan To determine the effect of differing the HA concentration and MW on the activity of beta-glucuronidase, 20 µg of cell lysate protein and 500 µM of substrate were co-incubated with 0-10 µg of HA/µg protein. As seen in FIG. 9 and Table 16, there was a distinct relationship between HA concentration and the stimulatory effect of beta-glucuronidase. In addition, there appeared to be a direct relationship between CD44 expression and the fold increase that HA exerted on the tumour cell beta-glucuronidase. Samples containing ≥2 µg of HA/µg protein demonstrated significantly more beta-glucuronidase activity when compared to the samples that did not contain HA. At 4 µg the increase in the beta-glucuronidase activity ranged from 0 to 28%. At 10 µg the increase in the beta-glucuronidase activity ranged from 20 to 125%, where there was a high correlation with CD44 expression.

TABLE 16

Raw data used to generate FIG. 9

| | Cell Line | | | | | | | | | |
|---|---|---|---|---|---|---|---|---|---|---|
| | SW-620* | HT-29* | SW1222* | MDA-MB-435# | MDA-MB-468# | LIM-1215* | SK-CO1* | MSTO-211H@ | HCT-116* | LIM-2099* |
| Cancer Type | Colon | Colon | Colon | Breast | Breast | Colon | Colon | Mesothelioma | Colon | Colon |
| CD44 Expression | 6% | 30% | 23% | 90% | 50% | 97% | 80% | 80% | 66% | 100% |
| Conc. of 860 kDa HA (µg/µg tumour cell protein) | Percentage change in beta-glucuronidase activity when compared to samples not containing hyaluronan (Mean ± SEM) where n = 6 | | | | | | | | | |
| 0 | 0 ± 0 | 0 ± 0 | 0 ± 0 | 0 ± 0 | 0 ± 0 | 0 ± 0 | 0 ± 0 | 0 ± 0 | 0 ± 0 | 0 ± 0 |
| 0.025 | −2 ± 2 | −8 ± 6 | −4 ± 3 | 1 ± 1 | 4 ± 1 | 3 ± 2 | −5 ± 4 | −12 ± 9 | 1 ± 4 | — |
| 0.05 | −2 ± 2 | −5 ± 4 | −2 ± 0 | 2 ± 0 | 4 ± 1 | 3 ± 4 | −11 ± 1 | −5 ± 2 | −6 ± 5 | 1 ± 1 |
| 0.25 | −6 ± 3 | −10 ± 8 | −3 ± 1 | 1 ± 1 | 7 ± 1 | 1 ± 1 | −2 ± 3 | 3 ± 2 | 0 ± 3 | −4 ± 1 |
| 0.5 | −8 ± 7 | −12 ± 10 | −11 ± 12 | 2 ± 3 | 1 ± 1 | 5 ± 2 | −3 ± 3 | 4 ± 3 | −2 ± 2 | 3 ± 0 |
| 2 | −7 ± 6 | −11 ± 9 | −7 ± 61 | 4 ± 0 | 14 ± 3 | 5 ± 3 | −5 ± 3 | 6 ± 1 | 8 ± 2 | 24 ± 1 |

TABLE 16-continued

Raw data used to generate FIG. 9

| | Cell Line | | | | | | | | | |
|---|---|---|---|---|---|---|---|---|---|---|
| | SW-620* | HT-29* | SW1222* | MDA-MB-435# | MDA-MB-468# | LIM-1215* | SK-CO1* | MSTO-211H@ | HCT-116* | LIM-2099* |
| 4 | −7 ± 6 | −6 ± 6 | 3 ± 1 | 11 ± 2 | 19 ± 3 | 1 ± 2 | 12 ± 7 | 13 ± 2 | 14 ± 1 | 28 ± 0 |
| 10 | 20 ± 2 | 31 ± 4 | 33 ± 2 | 64 ± 4 | 66 ± 1 | 81 ± 4 | 85 ± 12 | 97 ± 7 | 98 ± 7 | 125 ± 7 |

It is possible to model the observed stimulatory concentrations of HA to what could occur in the clinical setting and therefore determine if this phenomenon could occur in vivo. The tumour cell lysates used in these experiments were generated by $26.7 \times 10^6$ tumour cells resulting in 3.6 mg tumour cell protein/ml of lysate. This equates to one tumour cell containing 0.135 ng protein/cell. Therefore if ≥2 μg of HA/per μg tumour cell protein resulted in the stimulation of endogenous beta-glucuronidase activity, then this would be ≥2 μg/7407 cells or ≥270 pg HA/cell.

To establish the biodistrubution of a bolus injection of 850 k Da hyaluronan, nude mice bearing human breast cancer xenografts were intravenously injected with 15.9±1.2 mg/kg of 825 kD [$^3$H] HA. Mice (n=5/time point) were killed at 15 min, 30 min, 60 min, 2 h, 4 h, 8 h, 24 h, 48 h and 72 h after intravenous administration. All body organs and fluids were removed, weighed and [$^3$H] radioactivity quanitated using β-scintillation counting. All tissues were analysed for the presence of HA metabolites, where the end-products of [$^3$H] water and [$^3$H]acetate were identified after 8 hours; no intermediate breakdown products of HA were detected. The below table only reports the uptake of HA before the commencement of significant metabolism of the 825 kDa HA. As seen in the below table, the highest percentage of the injected dose that accumulated in the tumour was 2.58%. Therefore if a human received 2 g of HA (assuming a 2 m$^2$ patient receiving 1 g HA/m$^2$, this is the highest dose of HA administered in the HyCAMP™ Phase 1 and 11 clinical trials) then approximately 51.6 mg of HA would accumulate per gram of tumour, equating to 51.6 pg of HA/cell (making the assumption that 1 g of tumour equates to 10$^9$ cells).

Evaluation of 10 kDa Hyaluronan

Figure 10:
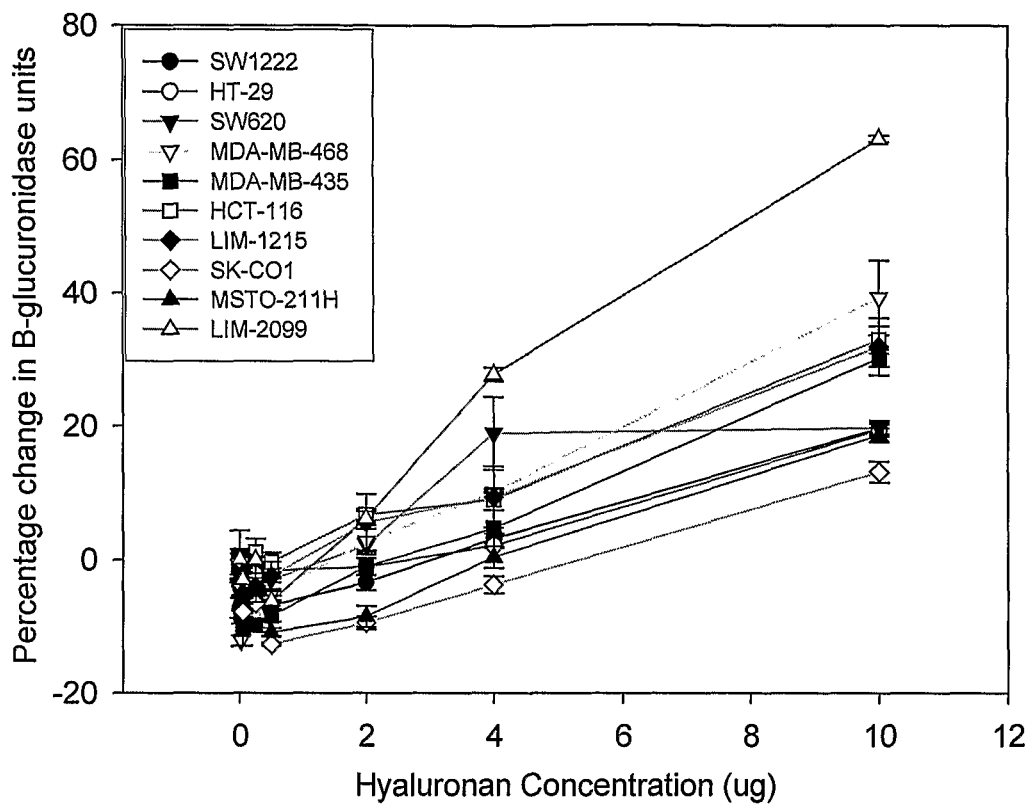
FIG. 10 is a graphical representation showing the effect of 10 kDa HA on the activity of tumour cell endogenous beta-glucuronidase

To determine the effect of differing the concentration and MW of HA on the activity of tumour cell beta-glucuronidase, one microgram of tumour cell protein and 500 μM of substrate were co-incubated with 0-10 μg of HA with a modal MW of 10 kDa, a molecular weight equivalent to the Hyal-2 digestion product that is located in cytoplasmic endosomes on route to the lysosome and in the lysosome before Hyal-1 digestion. As seen in FIG. 10 and Table 17, at >2 μg of HA there was significantly more beta-glucuronidase activity when compared to the samples which did not contain HA. At 4 μg the increase in the beta-glucuronidase activity ranged from 0 to 28%. At 10 μg the increase in the beta-glucuronidase activity ranged from 13 to 63%. In the case of the 10 kDa HA there did not appear to be a correlation between CD44 expression and the fold increase in beta-glucuronidase activity.

It is possible to model the observed stimulatory concentrations of HA to what could occur in the clinical setting and therefore determine if this phenomenon could occur in vivo. The tumour cell lysates used in these experiments were generated by $26.7 \times 10^6$ tumour cells resulting in 3.6 mg tumour cell protein/ml of lysate. This equates to one tumour cell containing 0.135 ng protein/cell. Therefore if ≥2 μg of HA/per μg tumour cell protein resulted in the stimulation of endogenous beta-glucuronidase activity, then this would be ≥2 μg/7407 cells or ≥270 pg HA/cell. The intravenous administration of 2 g of HA (assuming a 2 m$^2$ patient receiving 1 g HA/m$^2$, this is the highest dose of HA administered in the HyCAMP™ Phase 1 and 11 clinical trials) would theoretically result in approximately 51.6 mg of HA per gram of tumour, equating to 51.6 pg of HA/cell (making the assumption that 1 g of tumour equates to 10$^9$ cells). Chromatographical analysis of the tumour homogenate after injection with 825 kDa [$^3$H]HA did not detect any 10 kDa HA as any intermediate degradation products of HA are rapidly processed via beta-glucuronidase to monosaccharides. As 10 kDa can be a substrate for beta-glucuronidase it is possible that in response to increased substrate within the tumoural environment the beta-glucuronidase would still respond in a similar manner in vivo resulting in an up-regulation of enzyme activity.

TABLE 17

Raw data used to generate FIG. 10

| | Cell Line | | | | | | | | | |
|---|---|---|---|---|---|---|---|---|---|---|
| | SW-620* | HT-29* | SW1222* | MDA-MB-435# | MDA-MB-468# | LIM-1215* | SK-CO1* | MSTO-211H@ | HCT-116* | LIM-2099* |
| Cancer Type | Colon | Colon | Colon | Breast | Breast | Colon | Colon | Mesothelioma | Colon | Colon |
| CD44** Expression | 6% | 30% | 23% | 90% | 50% | 97% | 80% | 80% | 66% | 100% |
| Conc. of 860 kDa HA (μg/μg tumour cell protein) | Percentage change in beta-glucuronidase activity when compared to samples not containing hyaluronan (Mean ± SEM) where n = 6 | | | | | | | | | |
| 0 | 0 ± 0 | 0 ± 0 | 0 ± 0 | 0 ± 0 | 0 ± 0 | 0 ± 0 | 0 ± 0 | 0 ± 0 | 0 ± 0 | 0 ± 0 |
| 0.025 | −5 ± 1 | −5 ± 1 | −5 ± 0 | −9 ± 1 | −12 ± 1 | 0 ± 0 | −4 ± 2 | −2 ± 1 | 0 ± 0 | — |
| 0.05 | −7 ± 0 | −3 ± 2 | −6 ± 0 | −11 ± 2 | −9 ± 0 | −4 ± 2 | −8 ± 1 | −5 ± 1 | 0 ± 1 | −3 ± 0 |
| 0.25 | −6 ± 1 | −2 ± 1 | −5 ± 2 | −10 ± 1 | −3 ± 3 | −4 ± 2 | −7 ± 0 | −5 ± 2 | 1 ± 2 | 0 ± 1 |

TABLE 17-continued

Raw data used to generate FIG. 10

| | Cell Line | | | | | | | | | |
|---|---|---|---|---|---|---|---|---|---|---|
| | SW-620* | HT-29* | SW1222* | MDA-MB-435[#] | MDA-MB-468[#] | LIM-1215* | SK-CO1* | MSTO-211H[@] | HCT-116* | LIM-2099* |
| 0.5 | −3 ± 0 | −2 ± 0 | −7 ± 2 | −8 ± 3 | −5 ± 2 | −3 ± 2 | −13 ± 0 | −11 ± 1 | 0 ± 1 | −6 ± 0 |
| 2 | 2 ± 1 | −1 ± 1 | −3 ± 1 | −1 ± 1 | 3 ± 2 | 6 ± 4 | −9 ± 1 | −9 ± 2 | 7 ± 1 | 6 ± 1 |
| 4 | 19 ± 5 | 2 ± 0 | 3 ± 1 | 5 ± 3 | 10 ± 0 | 9 ± 5 | −4 ± 3 | 0 ± 2 | 9 ± 2 | 28 ± 1 |
| 10 | 20 ± 1 | 19 ± 1 | 20 ± 1 | 30 ± 1 | 39 ± 6 | 32 ± 4 | 13 ± 2 | 19 ± 1 | 33 ± 2 | 63 ± 0 |

Evaluation of <2 kDa Hyaluronan

Figure 11:
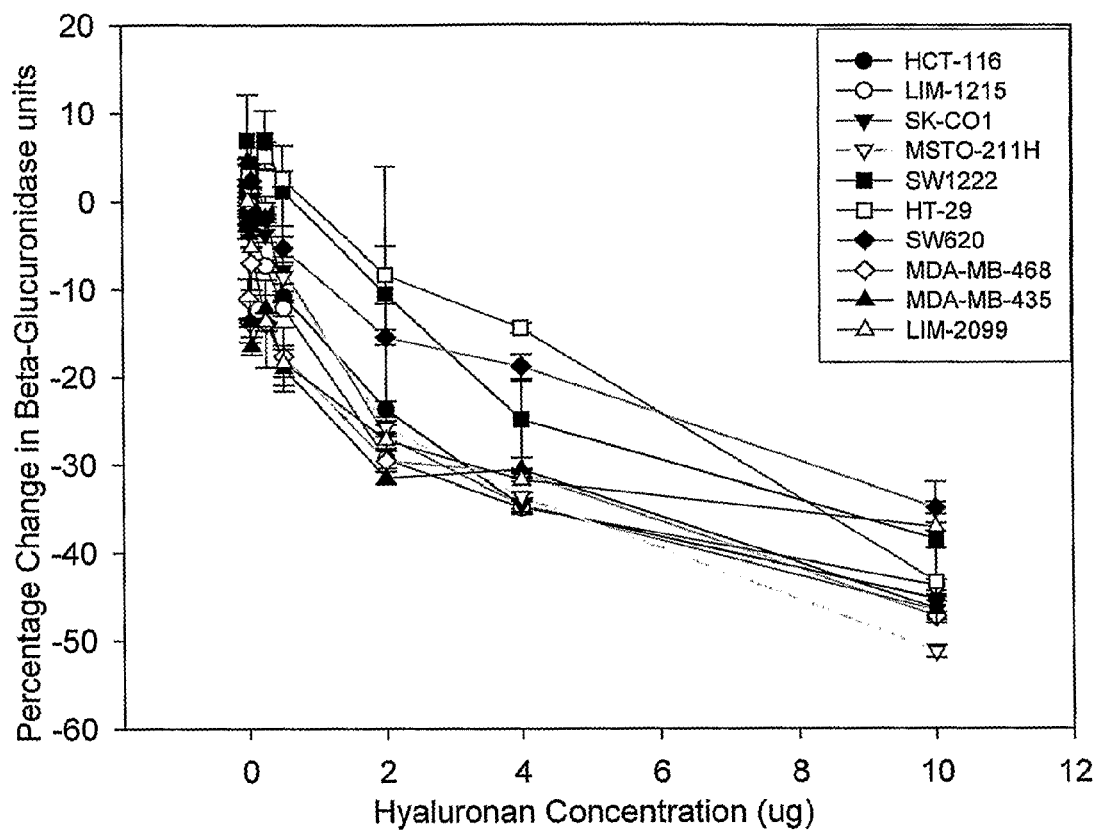
FIG. 11 is a graphical representation showing the effect of <2 kDa HA on the activity of tumour cell endogenous beta-glucuronidase

To determine the effect of different hyaluronan concentrations and molecular weight on the activity of beta-glucuronidase, one microgram of tumour cell protein and 500 μM of substrate were co-incubated with 0-10 μg of hyaluronan with a modal MW of <2 kDa. As seen in FIG. 11 and Table 18, at HA concentrations as low as 2 μg there was significant inhibition of the tumour cell beta-glucuronidase when compared to samples that did not contain HA. As the concentration of HA increased up to 10 μg of HA the degree of inhibition increased, where the beta-glucuronidase activity decreased by up to 47%.

Chromatographical analysis of the tumour homogenate after injection with 825 kDa [$^3$H]HA (demonstrated that no small fragments of HA <2 kDa) were detected in the tumour homogenates, therefore if these observations are translatable to the clinical situation, then there would be no HA-mediated inhibition of the intra-tumoural beta-glucuronidase.

colorectal adenocarcinoma. Patients were required to have metastatic disease that was either refractory to or had progressed within 6 months of first line 5-FU (and/or capecitabine) treatment. Previous oxaliplatin was permitted but at the time of initiation of this phase I study, oxaliplatin-based therapy was not readily available as a first line treatment regimen for the management of metastatic CRC. Other eligibility criteria were age 18-75, ≥1 measurable lesion (≥1 cm on spiral CT or MRI), ECOG performance status (PS) of 0 or 1, estimated survival of ≥12 weeks, adequate bone marrow function (neutrophil count ≥1.5×10$^9$/L, platelets ≥100×10$^9$/L), adequate liver function (bilirubin ≤1.25× upper limit of normal, ALT ≤5× upper limit of normal) and adequate renal function (creatinine of ≤0.2 mmol/L). Major exclusion criteria were active inflammatory bowel disease, ≥grade 2 chronic diarrhea, bulky disease (>50% hepatic involvement, >25% lung involvement, or abdominal mass ≥10 cm), cerebral metastases, Gilbert's syndrome, previous exposure to irinotecan, any prior radiotherapy to the pelvis or to >30% of bone marrow, currently active second malignancy or other serious co-morbid disease. All patients provided written informed consent prior to enrolment and the study was approved by the ethics committee of the participating institution.

TABLE 18

Figure 8:
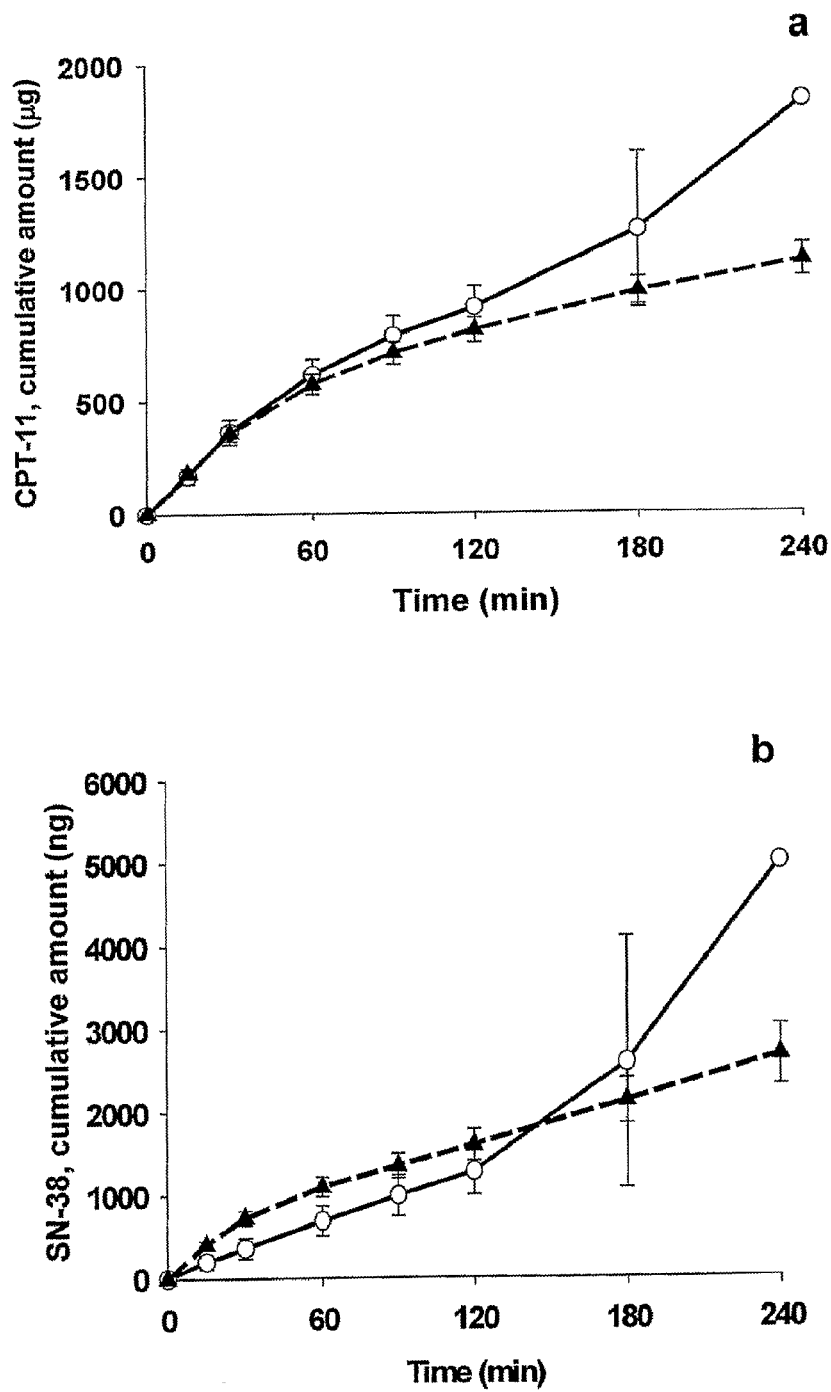
FIG. 8 is a graphical representation demonstrating cumulative intestinal exsorption of CPT-11 (a), SN-38 (b), SN-38G (c), and APC (d) following a single intravenous injection of irinotecan (60: open circles) and HyCAMP™ (26.6/60: filled triangles). Each value represents the average±SEM (a): p=<0.05 compared with irinotecan group.
Figure 8:
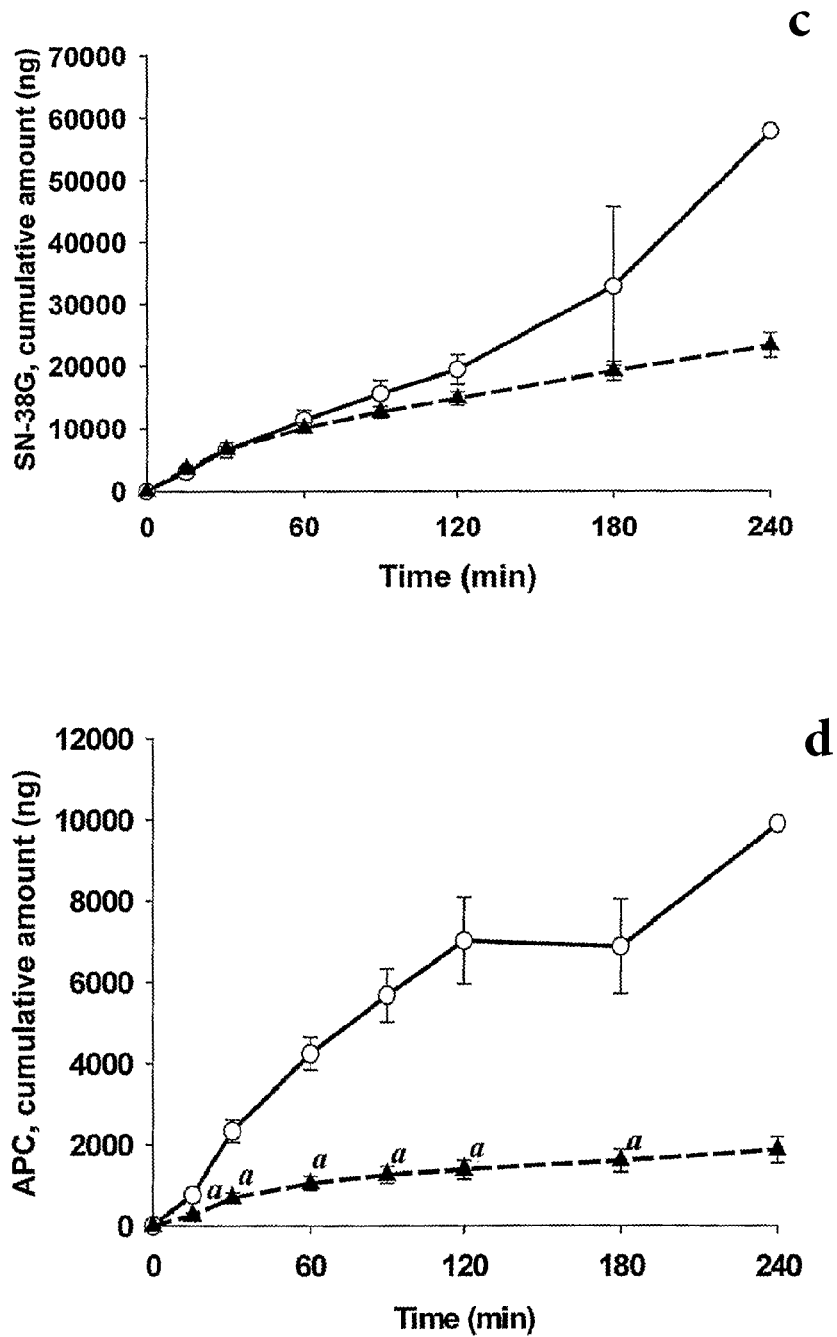

Raw data used to generate FIG. 8

| | Cell Line | | | | | | | | | |
|---|---|---|---|---|---|---|---|---|---|---|
| | SW-620* | HT-29* | SW1222* | MDA-MB-435[#] | MDA-MB-468[#] | LIM-1215* | SK-CO1* | MSTO-211H[@] | HCT-116* | LIM-2099* |
| Cancer Type | Colon | Colon | Colon | Breast | Breast | Colon | Colon | Mesothelioma | Colon | Colon |
| CD44** | 6% | 30% | 23% | 90% | 50% | 97% | 80% | 80% | 66% | 100% |
| Expression Conc. of 860 kDa HA (μg/μg tumour cell protein) | Percentage change in beta-glucuronidase activity when compared to samples not containing hyaluronan (Mean ± SEM) where n = 6 | | | | | | | | | |
| 0 | 0 ± 0 | 0 ± 0 | 0 ± 0 | 0 ± 0 | 0 ± 0 | 0 ± 0 | 0 ± 0 | 0 ± 0 | 0 ± 0 | 0 ± 0 |
| 0.001 | −3 ± 2 | −3 ± 1 | 7 ± 5 | 5 ± 0 | −11 ± 2 | −2 ± 1 | 2 ± 1 | −1 ± 1 | 1 ± 1 | — |
| 0.025 | −1 ± 2 | 3 ± 1 | 3 ± 2 | −14 ± 2 | −14 ± 0 | −3 ± 0 | 0 ± 1 | −1 ± 0 | 3 ± 2 | — |
| 0.05 | 2 ± 1 | 3 ± 1 | 0 ± 4 | −16 ± 1 | −7 ± 3 | −2 ± 1 | −2 ± 1 | −1 ± 0 | 4 ± 2 | −5 ± 0 |
| 0.25 | −2 ± 0 | 5 ± 2 | 7 ± 3 | −12 ± 2 | −14 ± 5 | −7 ± 1 | −4 ± 1 | −1 ± 1 | −1 ± 0 | −14 ± 1 |
| 0.5 | −5 ± 3 | 3 ± 1 | 1 ± 5 | −19 ± 3 | −18 ± 3 | −12 ± 1 | −8 ± 2 | −9 ± 2 | −11 ± 1 | −18 ± 2 |
| 2 | −15 ± 1 | −8 ± 3 | −11 ± 14 | −31 ± 1 | −30 ± 1 | −29 ± 1 | −27 ± 1 | −26 ± 1 | −24 ± 1 | −27 ± 0 |
| 4 | −19 ± 1 | −14 ± 1 | −25 ± 4 | −31 ± 0 | −31 ± 0 | −35 ± 1 | −35 ± 1 | −34 ± 0 | −35 ± 0 | −32 ± 0 |
| 10 | −35 ± 1 | −43 ± 1 | −39 ± 7 | −46 ± 2 | −47 ± 0 | −44 ± 1 | −47 ± 1 | −51 ± 1 | −45 ± 0 | −37 ± 0 |

Example 8

Phase 1 Clinical Report Results for HyCAMP™

Materials and Methods

Patient Selection

All patients entered into this study had advanced or metastatic CRC with present or past histological documentation of Study Design The formulation of HA and irinotecan (HyCAMP™) was administered intravenously over 90 minutes every 3 weeks to a maximum of 6 cycles. The dose of HA was fixed at 1000 mg/m² and the initial dose of irinotecan was 300 mg/m² [HyCAMP(1000/300)]. All patients received a pre-medication of a 5-HT3 inhibitor and dexamethasone. If no significant treatment related toxicity was seen at this initial dose then the dose of irinotecan was to be escalated to 350 mg/m² for subsequent cycles [HyCAMP(1000/350)]. No dose modification for HA was planned.

Toxicities were graded according to the National Cancer Institute Common Toxicity Criteria (NCICTC), version 1. Patients who experienced any grade III or IV toxicities (other than alopecia and thrombo-embolic events) received a 25% dose reduction of their subsequent cycles of irinotecan (but not HA). A dose delay of up to 21 days till resolution of the toxicities to grade I or less was permitted. Patients who developed grade III or IV thrombo-embolic events were taken off study. All patients received education regarding the potential for treatment related diarrhea and the appropriate use of loperamide, which was routinely dispensed at the time of the first cycle of HyCAMP™. Prophylactic use of granulocyte-colony stimulating factors or erythropoietin was not permitted.

Baseline Efficacy and Safety Evaluation

Before treatment, the clinical status of each patient was assessed by medical history, physical examination, complete blood count, serum CEA and chemistry panel. A baseline CT scan of chest, abdomen and pelvis was performed within 4 weeks prior to the first cycle of treatment. During treatment, patients were assessed with a physical examination, complete blood count, blood chemistry and toxicity grading on day 1 of every cycle. In addition a day 10 complete blood count was scheduled for the first 2 cycles. Following every 2 cycles, radiological imaging was repeated to determine disease status. RECIST criteria were used for assessment of response using previously published definitions of complete response (CR), partial response (PR), stable disease (SD) and progressive disease (PD).

Pharmacokinetics

In the first cycle, on the day of drug administration, blood samples for quantitation of irinotecan and its metabolites SN-38 and SN-38G were drawn at 0, 30, 60, 90 min (during infusion) and at 5, 10, 15, 20, 30, 60 min and 2, 3, 4, 6, 24, 47, 72 and 96 h after the cessation of the infusion of the drug. Blood was collected in heparinized tubes and plasma was separated from blood cells by centrifugation (1200 g for 10 minutes) and frozen at minus 20° C. then stored at −80° C. until analysed. The concentrations of analytes in thawed plasma were determined using reversed phase HPLC. Concentrations were calculated by comparison to standard curves created using 1/x weighted linear regression fitted to plots of concentration versus response where response equalled the ratio of peak area of analyte to internal standard.

Sample extraction: Prior to CPT-11 and SN-38 quantitation samples were extracted by adding 400 µl of ice cold 1:1 acetonitrile:methanol containing 18 ng of internal standard (Camptothecin, Sigma, USA) to 200 µl of patient plasma. The extraction mix was cleared by centrifugation at 13,5000 rpm for 5 min in a Biofuge 13 (Beckman, USA). The supernatant was dried and reconstituted in 200 µl of mobile phase before application to the HPLC.

HPLC Quantitation of CPT-11 and SN-38: Separation was achieved using a SGE SS Warkosil C18 column (5 µm, 150× 4.6 mm i.d) which was protected by an Alltech C18 (5 µm, 7.5×4.6 mm i.d) guard column. The column temperature was maintained at 30° C. The mobile phase was 0.025M $KH_2PO_4$: Acetonitrile (75:25 v/v) adjusted to pH 2.5 with $H_3PO_4$ and the flow rate was set to 1 ml/min. The samples were cooled at 4° C. and injected into the column with a 30 µl injection volume. HPLC assays used were validated for specificity, sensitivity, linearity and sample and stock stability over the appropriate periods of storage/use. The within-day and between-day accuracy and precision was less than ±15%, or ±20% at the limit of quantitation. The potential for chromatographic interference from other co-administered agents including hyaluronic acid (HA) and a range of antiemetics and antihistamines was also assessed prior to analysis.

Quantitation of SN-38G: The SN-38G was estimated by quantitating the increase in SN-38 levels after hydrolysis of SN-38G by beta-glucuronidase. In brief, 200 µl aliquots of the plasma sample were incubated with 1000 units of beta-glucuronidase (Type B10, 10,400 units/mg; Sigma, USA) at 37° C. for 2 h. At the completion of the enzymic digestion samples were extracted and chromatographed as described above. SN-38G levels were expressed as ng/ml SN-38 based on a 100% pure reference standard of SN-38.

Results

Patient Characteristics

Twelve patients were enrolled into the study between July 2003 and September 2004. All patients were evaluable for response and toxicity. Nine males and 3 females were enrolled with a median age of 63 years (range 39 to 73). All patients had received prior 5-FU chemotherapy and 3 had also received oxaliplatin. Patient characteristics at study entry are shown in Table 1. The median number of cycles received was 5 (range 1-6).

Pharmacokinetics

When compared to historical data, the formulation of HyCAMP appeared to alter the pharmacokinetics of both irinotecan (CPT-11) and SN38 (Table 19). The mean half life (t½) of CPT-11 when formulated with HA was approximately 18 h compared to irinotecan alone which has been observed to be approximately 12 h. These data indicate that due to the unaltered $C_{max}$ and clearance figures, the formulation of HA are altering the metabolism or pharmacodynamics of irinotecan. This scientific assumption is confirmed when comparing the $C_{max}$ and Area Under the Curve for the potent metabolite, SN-38. These collective SN-38 pharmacokinetic data suggests that the HA is modifying the metabolic activation and potentially pharmacodynamics of irinotecan. The key enzymes in such a metabolic cascade would be carboxylesterase, UDP glucuronosyltransferase and beta-glucuronidase.

Figure 12:
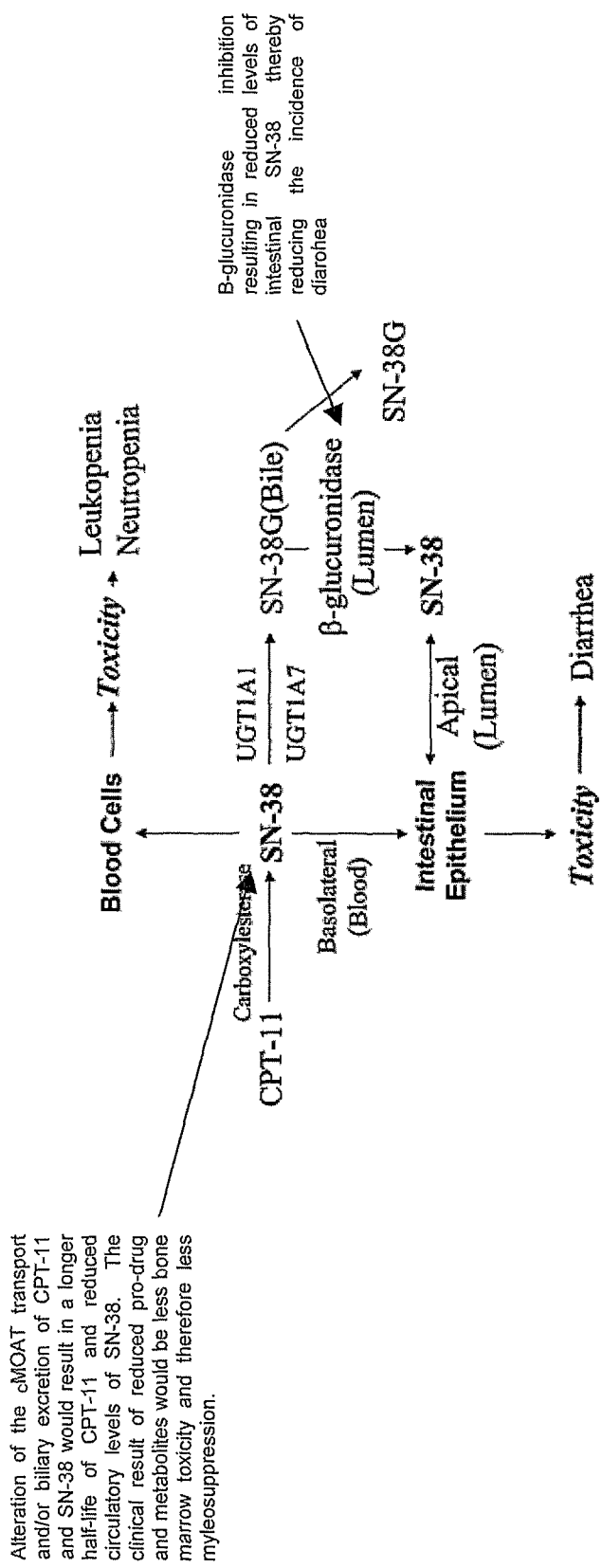
FIG. 12 is a diagram showing the metabolic pathways of CPT-11.
Figure 13:
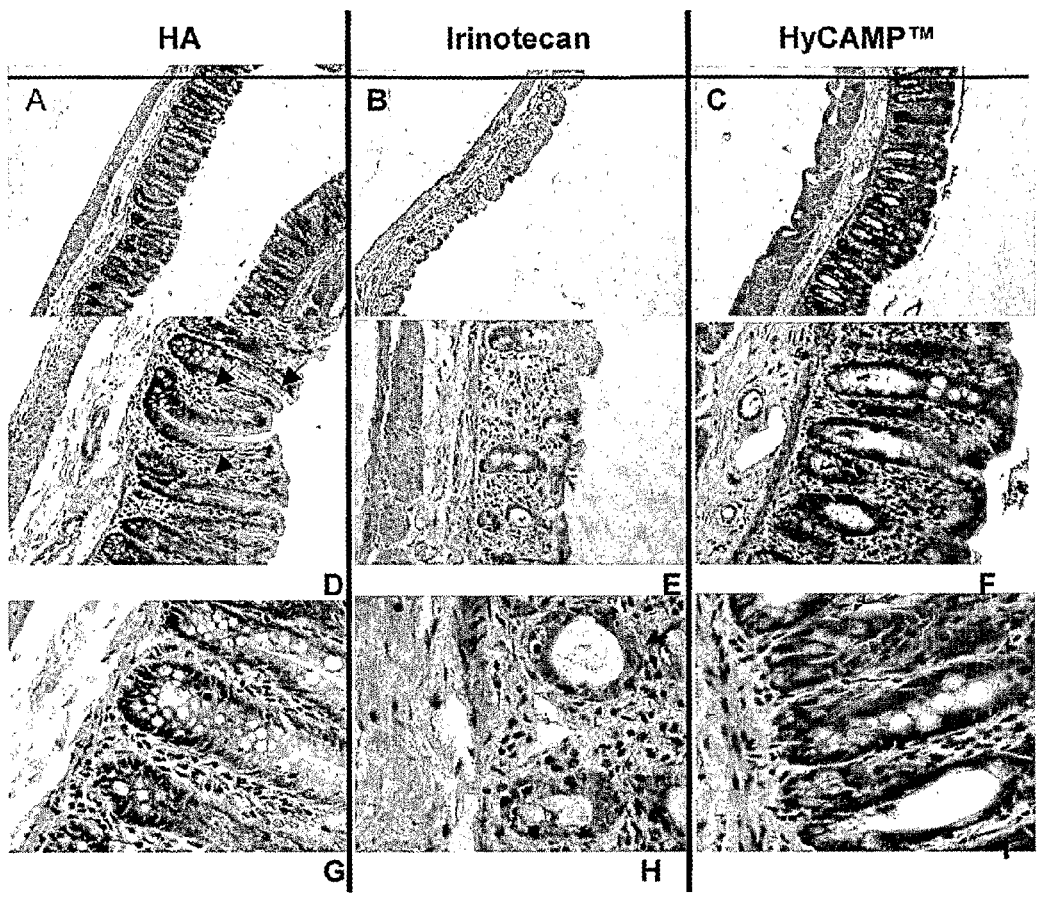
FIG. 13 are photographical representations showing changes to caecum morphology from rats chronically exposed to Irinotecan and HyCAMP™. Rats received daily injection of irinotecan (60.0) or HyCAMP™ (26.6/60.0). At experimental endpoint portions of the gastrointestinal tract were processed. Panel A, D and G: micrographs from rats receiving hyaluronan; panels B, E and H: micrographs from rats receiving irinotecan and; panels C, F and I: micrographs from rats receiving HyCAMP™. Note general morphological changes in mucosal crypts between irinotecan and HyCAMP™ (panel B and C respectively). HyCAMP™ treated caecum is similar to that observed in control (panel A).

If this observed effect was the result of reduced carboxylesterase activity, the $C_{max}$ level of CPT-11 would be higher than expected as the enzyme would not be able to convert the CPT-11 to SN-38 as efficiently which would manifest as reduced SN-38 but elevated levels of circulatory CPT-11. If the UDP glucuronosyltransferase was the target enzyme then the pharmacokinetic effect would be altered levels of SN-38G but this was not observed. The observed results could be as a consequence of the following metabolic pathway alteration (FIG. 12)

TABLE 19

Plasma Pharmacokinetic Parameters of Irinotecan and its Metabolites SN-38 and SN38G after the infusion of Hyaluronan and Irinotecan formulated as HyCAMP

| Dose of CPT-11 (mg/m$^2$) | BSA[1] (m$^2$) | Duration of infusion (hr) | Dose of CPT-11 (mg) | (mg/h) | CPT-11 C$_{max}$ (ng/ml) | AUC$_{total}$ (μg · hr/ml) | t$_{1/2}$ (hr) | Clearance (L/h) | (L/h/m$^2$) |
|---|---|---|---|---|---|---|---|---|---|
| 300 (n = 5) | 1.8 ± 0.2 | 1.6 ± 0.2 | 522 ± 63 | 329 ± 64 | 3956 ± 796 | 24.7 ± 5.8 | 18.1 ± 2 | 22.8 ± 9.8 | 12.5 ± 4.4 |
| 350 (n = 5) | 1.9 ± 0.1 | 1.8 ± 0.3 | 666 ± 42 | 382 ± 44 | 4360 ± 1332 | 28.3 ± 8.5 | 18.7 ± 4.6 | 25.5 ± 8.6 | 13.3 ± 3.8 |
| Historical Comparator Publications | | | | | | | | | |
| 350[3] | 1.86 | 1.5 | Not specified | | 3392 ± 874 | 23.0 ± 7.3 | 12.2 ± 1.6 | Not specified | 12.1 ± 3.8 |
| 350[4] | 1.86 | 1.5 | Not specified | | Not specified | 20.5 ± 7.1 | Not specified | Not specified | Not specified |

| Dose of CPT-11 (mg/m$^2$) | CPT-11 Vol. Dist. (L)[2] | SN-38 C$_{max}$ (ng/ml) | AUC$_{total}$ (μg · hr/mL) | t$_{1/2}$ (hr) | SN38-G C$_{max}$ (ng/ml) | AUC$_{total}$ (μg · hr/ml) | t$_{1/2}$ (hr) |
|---|---|---|---|---|---|---|---|
| 300 (n = 5) | 614 ± 329 | 23.6 ± 8 | 0.3 ± 0.1 | 19.6 ± 3.5 | 61.8 ± 20.6 | 1.0 ± 0.3 | 15.8 ± 2.2 |
| 350 (n = 5) | 668 ± 197 | 30.1 ± 16.5 | 0.4 ± 0.2 | 24.7 ± 15.8 | 96.6 ± 57.4 | 1.6 ± 0.6 | 19.2 ± 4.3 |
| Historical Comparator Publications | | | | | | | |
| 350[3] | Not specified | 56 ± 28 | 0.71 ± 0.42 | 21.0 ± 8.2 | 168 ± 69 | 2.3 ± 1.2 | 17.2 ± 3.6 |
| 350[4] | Not specified | Not specified | 0.64 ± 0.34 | Not specified | Not specified | 4.5 ± 4.7 | Not specified |

[1]BSA (body surface area) used for dose calculation, was capped at a maximum of 2.0 m$^2$.
[2]Vol. Dist. (L) = [Clearance (L/hr) * t$_{1/2}$ (hr)]/0.693.
The model independent calculation of parameters used 2 or 3 terminal elimination points selected visually for best fit from the log-linear elimination profiles.
All figures represent the mean ± one standard deviation Toxicity Grade III liver dysfunction, considered to be due to progressive disease, was observed in the first patient enrolled at the HyCAMP(1000/300) dose level after the first cycle of treatment. A further 4 patients were treated at this level with no dose limiting toxicity, and they received HyCAMP(1000/350) for the second and subsequent cycles. Seven patients commenced treatment at the HyCAMP(1000/350) dose level. Dose reduction took place for two patients: a 50% reduction in irinotecan dose at cycle 2 because of grade IV febrile neutropenia at cycle 1; and a 25% reduction in irinotecan dose at cycle 5 because of grade III lethargy at cycle 4. One patient required a treatment delay (but no dose modification) at cycles 2 and 6 because of neutropenia during cycles 1 and 5 (grades III and II, respectively).

Treatment related grade III and IV toxicity according to scheduled visits is summarized in Table 3. The single episode of grade III diarrhea occurred during cycle 5 in a patient who had not had significant diarrhea prior to this. This patient would have required a dose reduction at cycle 6 however this did not take place because the patient was removed from the study for progressive disease at the end of cycle 5. Other grade III/grade IV toxicities that are not shown in Table 3 included liver dysfunction, considered related to progressive disease, and hyperglycemia, considered related to steroid premedication. There were a total of 9 episodes of NCICTC grade III/IV toxicities. Of these, 3 were felt to be study drug related. They were 1 grade III diarrhea, 1 grade IV neutropenia and 1 grade III neutropenia. The episode of grade III neutropenia was documented on day 10 and the neutrophil count had recovered by the date the next cycle was due, so this did not impact on treatment. There were no toxic deaths associated with treatment.

Tumor Response and Survival

All 12 patients were evaluable for response. Response data are summarised in Table 20. Partial responses were seen in two patients, for an overall response rate of 17%. Five patients had stable disease and 5 progressive disease as their best response. The median time to progression was 6 months and median overall survival was 16 months.

Although the sample population was small, analysis of the CEA levels proved interesting where in patients 6 and 9 the CEA levels decreased substantially while computed tomography assessment indicated progressive disease. Follow-up on these "non-responding" patients has revealed that these patients were still alive 623 and 629 days after commencement of treatment, which falls within the expected survival for responders assessed by CEA.

TABLE 20

Tumour response and survival

| Toxicity | % Observed (n = 12) | % Expected Mean (Range) |
|---|---|---|
| Grade 3-4 Diarrhoea | 8 | 28 (19-41)[1-7] |
| Grade 3-4 Vomiting | 0 | 18 (11-30)[1-6] |

TABLE 20-continued

| Tumour response and survival | | |
|---|---|---|
| Grade 3-4 Neutropenia | 17 | 30 (14-47)[1-7] |
| Febrile Neutropenia | 8 | 5 (2-7)[1-3,6] |
| Dose Reduction | 24 | 41[1] |

| Efficacy | % Observed (n = 12) | % Expected Mean (Range)[2,4,5] |
|---|---|---|
| Response Rate (CR & PR) | 16 | 16 (5-22) |
| Stable disease | 42 | 34 (28-38) |
| Progressive Disease | 42 | 51 (42-67) |

| Survival | % Observed (n = 12) | % Expected Mean (Range)[1-3,5] |
|---|---|---|
| Median Survival (Months) | 16.6 | 9.6 (7-10.8)[1-4] |
| Median time to progression (Months) | 6.2 | 4.0 (3-4.5)[1,2,4,5] |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

European Patent No. 0 138 572
European Patent No. 0 216 453
European Patent No. 0 341 745
Sands et al. *Protocols for Gene Transfer in Neuroscience* 263-274, 1996
Takasuna et al. *Cancer Res* 56:3752-3757, 1996
U.S. Pat. No. 4,522,811
U.S. Pat. No. 4,851,521
U.S. Pat. No. 4,965,353
U.S. Pat. No. 5,202,431,
U.S. Pat. No. 5,852,002
U.S. Pat. No. 6,027,741
U.S. Pat. No. 6,069,135
U.S. Pat. No. 6,552,184
U.S. Pat. No. 6,579,978
U.S. Pat. No. 6,620,927
U.S. Pat. No. 6,831,172
WO 00/41730
WO 02/05852
Wolfe & Sands *Protocols for Gene Transfer in Neuroscience,* 1996

The invention claimed is:

1. A method of reducing gastrointestinal toxicity and/or myelosuppression in a subject having cancer and to be treated with a therapeutic agent, comprising intravenous administration to the subject a formulation comprising a combination of:
 (i) hyaluronan of average molecular weight of between 350 Daltons and 2 kDaltons,
 (ii) hyaluronan of average molecular weight between 750 kDaltons and 1000 kDaltons, and
 (iii) the therapeutic agent, selected from the group consisting of daunorubicin, daunomycin, dactinomycin, doxorubicin, epirubicin, idarubicin, esorubicin, mafosfamide, ifosfamide, cytosine arabinoside, mitomycin C, actinomycin D, mithramycin, prednisone, tamoxifen, procarbazine, mitoxantrone, amsacrine, chlorambucil, 6-mercaptopurine, 6-thioguanine, cytarabine, 5-azacytidine, deoxycoformycin, 5-fluorouracil, 5-fluorodeoxyuridine, methotrexate, colchicine, taxol, vincristine, vinblastine, etoposide, trimetrexate, irinotecan, topotecan, gemcitabine, teniposide, and diethylstilbestrol; and wherein the administration of said formulation reduces gastrointestinal toxicity and/or myelosuppression relative to administration of the therapeutic agent alone.

2. The method according to claim 1, wherein the therapeutic agent is irinotecan.

3. The method according to claim 1, wherein the therapeutic agent is gemcitabine.

4. The method according to claim 1, wherein the therapeutic agent is doxorubicin.

5. The method according to claim 1 wherein said formulation comprises a combination of:
 (i) hyaluronan of average molecular weight between 350 Daltons and 2 kDaltons,
 (ii) hyaluronan of average molecular weight of about 860 kDaltons, and
 (iii) said therapeutic agent.

6. The method according to claim 5, wherein the therapeutic agent is irinotecan.

7. The method according to claim 5, wherein the therapeutic agent is gemcitabine.

8. The method according to claim 5, wherein the therapeutic agent is doxorubicin.

* * * * *